(12) United States Patent
Nyan

(10) Patent No.: US 11,306,367 B1
(45) Date of Patent: Apr. 19, 2022

(54) METHODS FOR RAPID DETECTION AND IDENTIFICATION OF VIRAL NUCLEIC ACIDS

(71) Applicant: Dougbeh-Chris Nyan, Germantown, MD (US)

(72) Inventor: Dougbeh-Chris Nyan, Germantown, MD (US)

( * ) Notice: Subject to any disclaimer, the term of this patent is extended or adjusted under 35 U.S.C. 154(b) by 274 days.

(21) Appl. No.: 14/821,865

(22) Filed: Aug. 10, 2015

Related U.S. Application Data

(63) Continuation of application No. 14/671,859, filed on Mar. 27, 2015, now abandoned.

(60) Provisional application No. 61/979,446, filed on Apr. 14, 2014.

(51) Int. Cl.
*C12Q 1/70* (2006.01)

(52) U.S. Cl.
CPC ............ *C12Q 1/707* (2013.01); *C12Q 1/701* (2013.01); *C12Q 1/703* (2013.01); *C12Q 1/706* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2012/0202190 A1* | 8/2012 | Ching | ............ | C12Q 1/706 435/5 |
| 2017/0044631 A1* | 2/2017 | Nyan | ............ | C12Q 1/703 |

OTHER PUBLICATIONS

Lee et al. (The Canadian Journal of Veterinary Research, 2011).*
Kelly A. Curtis et al., Sequenc-Specific Detection Method for Reverse Transcription, Loop-Mediated Isothermal Amplification of HIV-1, Journal of Medical Virology 81:966-972 (2009).

* cited by examiner

*Primary Examiner* — Agnieszka Boesen
(74) *Attorney, Agent, or Firm* — Daniel S. Polley, P.A.

(57) ABSTRACT

Disclosed herein are methods of detecting viral nucleic acids in a sample that include contacting the sample with one or more sets of loop-mediated isothermal amplification (LAMP) primers specific for a viral nucleic acid of interest (such as hepatitis B virus, hepatitis C virus, hepatitis E virus, human immunodeficiency virus, West Nile virus, or Dengue virus nucleic acids) under conditions sufficient to produce an amplification product and detecting the amplification product(s). In some examples, the amplification product is detected by gel electrophoresis, while in other examples, the amplification product is detected by detecting signal from a label included in one or more of the LAMP primers. Primers and kits for use for detection of viral nucleic acids by LAMP are also disclosed herein.

19 Claims, 26 Drawing Sheets

Specification includes a Sequence Listing.

FIG. 1

```
121 aatctcctcg aggactgggg accctgcacc gaacatggag aacatcacat caggattcct
                                                         ----HBU-F3----
181 aggacccctg ctcgtgttac aggcggggtt tttcttgttg acaagaatcc tcacaatacc
    -------->  ----F2 of HBU-FIP-------->   <-------HBU-LF-------
241 gcagagtcta gactcgtggt ggacttctct caatttctta ggggatcac ccgtgtgtct
    <---F1c of HBU-FIP------          --------R1c of HBU-RIP------>
301 tggccaaaat tcgcagtccc caacctccaa tcactcacca acctcctgtc ctccaatttg
    -HBU-LR----------->     <----R2 of HBU-RIP----
361 tcctggttat cgctggatgt gtctgcggcg ttttatcata ttcctcttca tcctgctgct
                                                  <----HBU-R3----
421 atgcctcatc ttcttattgg ttcttctgga ttatcaggt atgttgcccg tttgtcctct
```

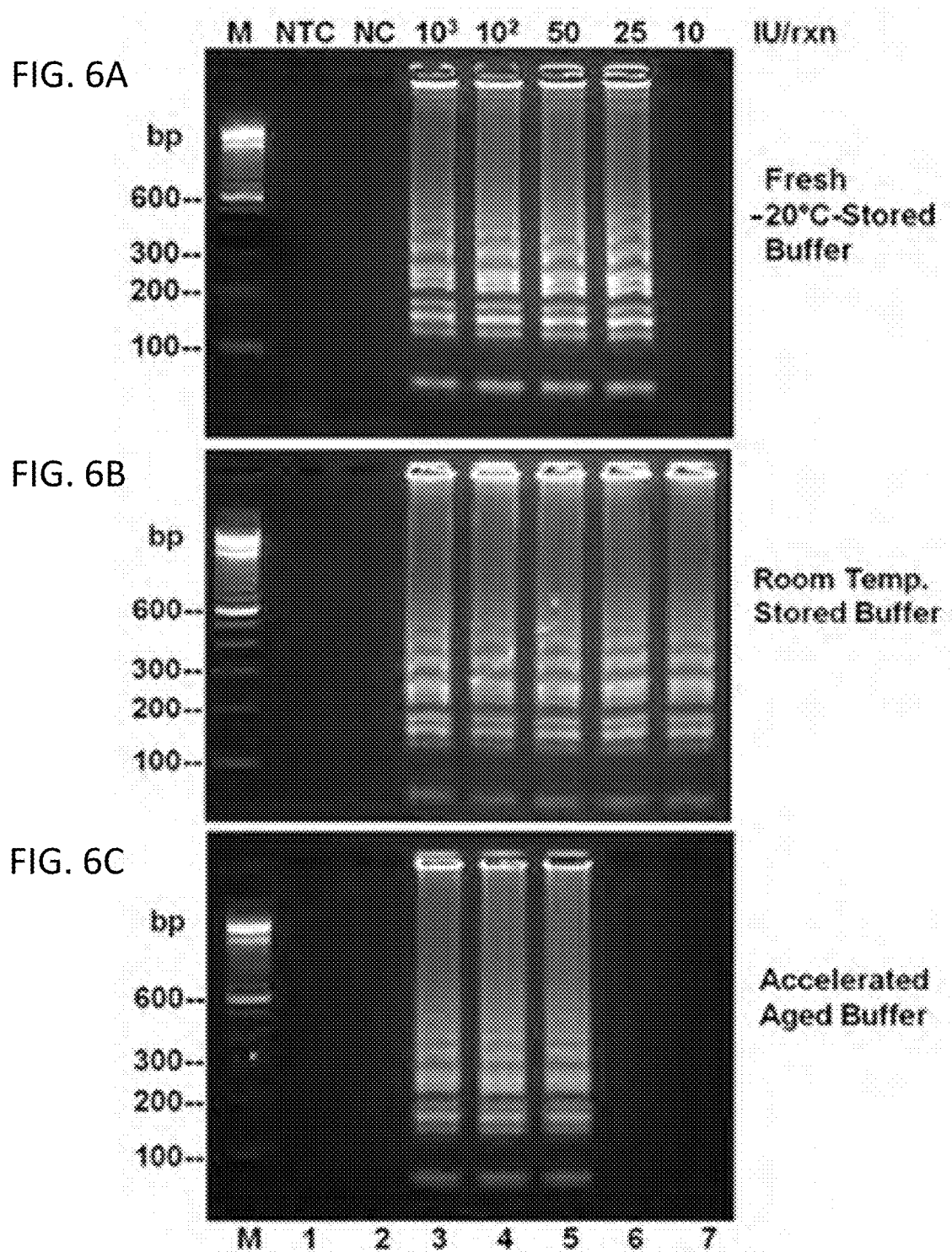

FIG. 7A

```
  1 ttcacgcaga aagcgtctag ccatggcgtt agtatgagtg ttgtacagcc tccaggaccc
 61 ccctcccgg gagagccata gtggtcttcg gaaccggtga gtacaccgga atcgccggga
121 tgaccgggtc ctttcttgga ttaacccgct caatgcccgg aaatttgggc gtgccccgc
181 aagactgcta gccgagtagt gttgggtcgc gaaggcctt gcggtactgc ctgatagggt
241 gcttgcgagt gccccggag gtctcgtaga ccgtgcacca tgagcacgaa tcctaaacct
301 caaagaaaaa ccaaacgtaa caccaaccgc cgcccaatgg acgttaagtt cccgggtggt
361 ggccagatcg ttggcggagt ttacttgttg ccgcgcaggg gccccagatt gggtgtgcgc
```

FIG. 7B

```
  1 gccagccccc tgatggggc gacactccac catgaatcac tccctgtga ggaactactg
 61 tcttcacgca gaaagcgtct agccatggcg ttagtatgag tgtcgtgcag cctccaggac
121 ccccctccc gggagagcca tagtggtctg cggaaccggt gagtacaccg gaattgccag
181 gacgaccggg tcctttcttg gataaacccg ctcaatgcct ggagatttgg gcgtgccccc
241 gcaagactgc tagccgagta tgttgggtc gcgaaggcc ttgtggtact gcctgatagg
301 gtgcttgcga gtgccccggg aggtctcgta gaccgtgcac catgagcacg aatcctaaac
361 ctcaaagaaa aaccaaacgt aacaccaacc gtcgcccaca ggacgtcaag ttcccgggtg
```

FIG. 7C

```
  1 acccgcccct aatagggcg acactccgcc atgaaccact ccctgtgag gaactactgt
 61 cttcacgcag aaagcgtcta gccatggcgt tagtatgagt gtcgtacagc ctccaggccc
121 cccctcccg ggagagccat agtggtctgc ggaaccggtg agtacaccgg aattgccggg
181 aagactggt cctttcttgg ataaacccac tctatgcccg gtcatttggg cgtgccccg
241 caagactgct agccgagtag cgttgggttg cgaaaggcct tgtggtactg cctgataggg
301 tgcttgcgag tgccccggga ggtctcgtag accgtgcacc atgagcacaa atcctaaacc
361 tcaaagaaaa accaaaagaa acaccaaccg tcgcccacaa gacgttaagt tccgggcgg
```

FIG. 7D

```
  1 acctgcctct tacgaggcga cactccacca tggatcactc ccctgtgagg aacttctgtc
 61 ttcacgcgga aagcgcctag ccatggcgtt agtacgagtg tcgtgcagcc tccaggaccc
121 ccctcccgg gagagccata gtggtctgcg gaaccggtga gtacaccgga atcgctgggg
181 tgaccgggtc ctttcttgga gcaacccgct caatacccag aaatttgggc gtgccccgc
241 gagatcacta gccgagtagt gttgggtcgc gaaggcctt gtggtactgc ctgatagggt
301 gcttgcgagt gccccggag gtctcgtaga ccgtgcaaca tgagcacact tcctaaacct
361 caaagaaaaa ccaaaagaaa caccatccgt cgcccacagg acgtcaagtt cccgggtggc
```

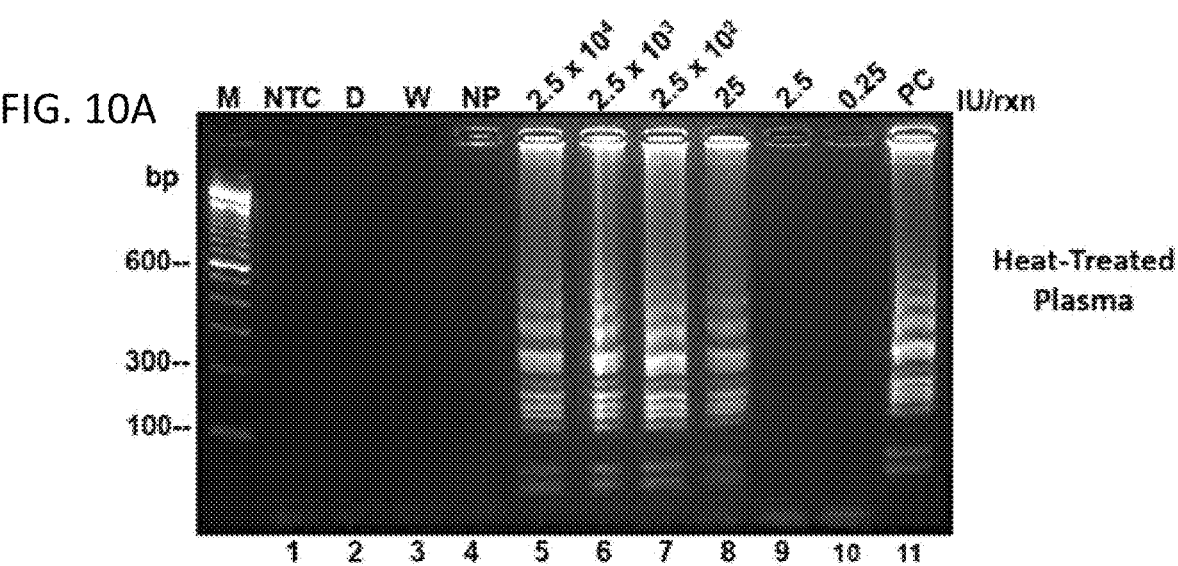
FIG. 10A
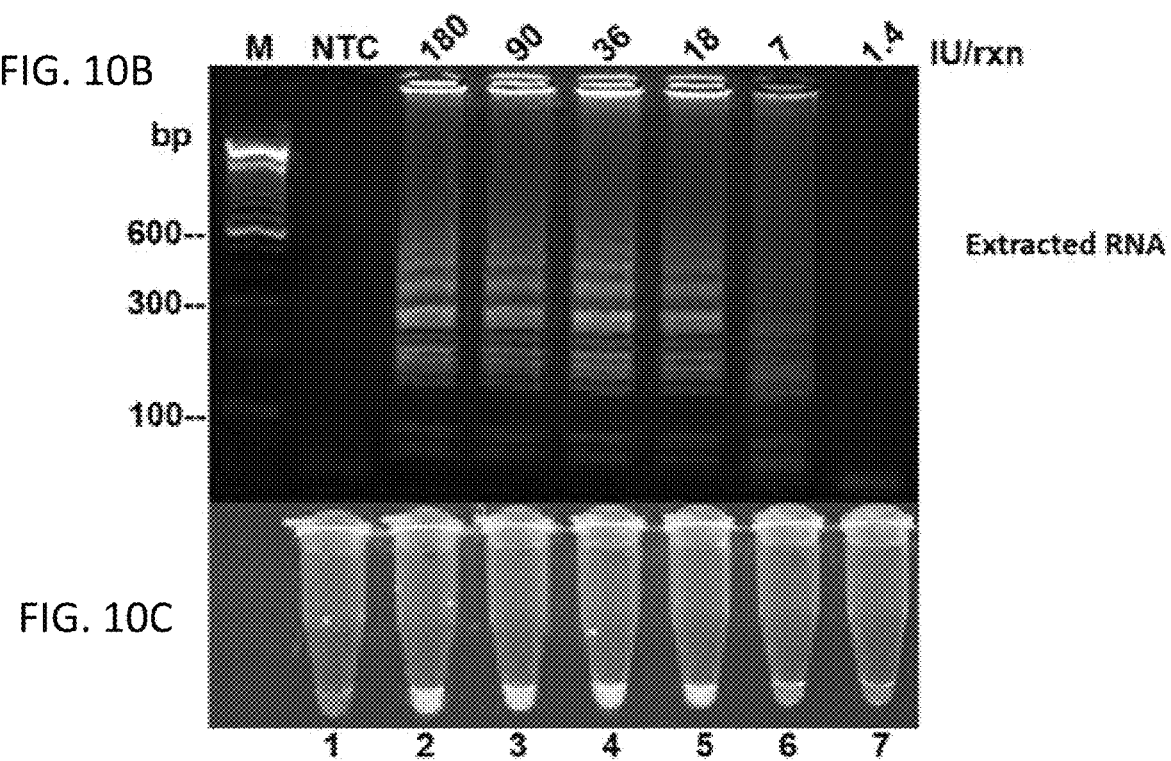
FIG. 10B
FIG. 10C

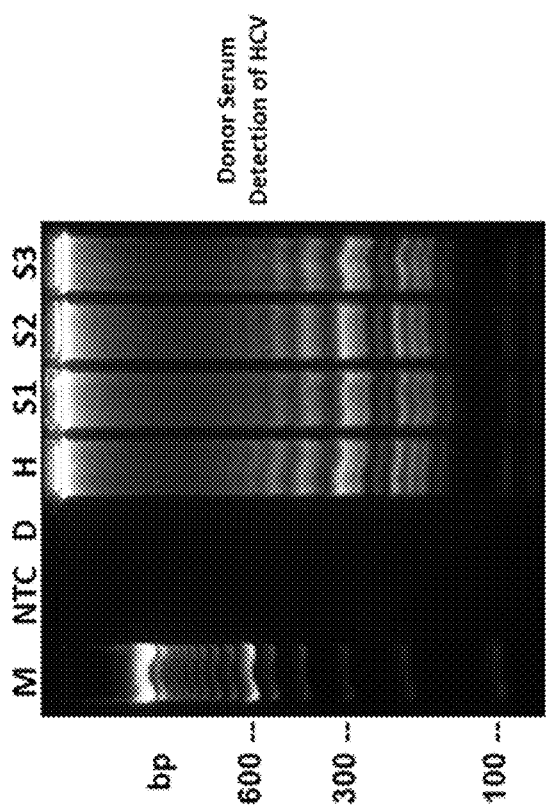
FIG. 11C
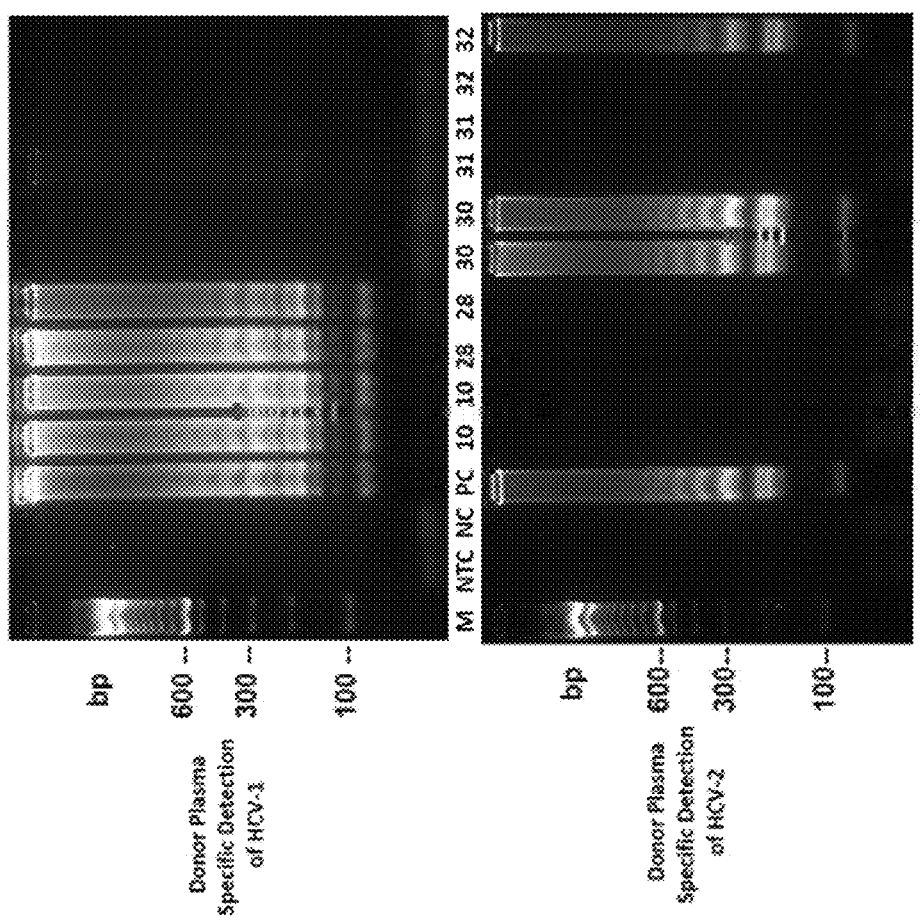
FIG. 11A
FIG. 11B

SEQUENCE LISTING

<160> NUMBER OF SEQ ID NOS: 81

<210> SEQ ID NO 1
<211> LENGTH: 20
<212> TYPE: DNA
<213> ORGANISM: Artificial Sequence
<220> FEATURE:
<223> OTHER INFORMATION: Synthetic primer: HBU-F3

<400> SEQUENCE: 1
tcctcacaat accgcagagt                                            20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer: HBU-R3

<400> SEQUENCE: 2
gcagcaggat gaagaggaat                                            20

<210> SEQ ID NO 3
<211> LENGTH: 46
<212> TYPE: DNA
<213> ORGANISM: Artificial Sequence
<220> FEATURE:
<223> OTHER INFORMATION: Synthetic primer: HBU-FIP

<400> SEQUENCE: 3
gttggggact gcgaattttg gcttttttaga ctcgtggtgg acttct              46

<210> SEQ ID NO 4
<211> LENGTH: 44
<212> TYPE: DNA
<213> ORGANISM: Artificial Sequence
<220> FEATURE:
<223> OTHER INFORMATION: Synthetic primer: HBU-RIP

<400> SEQUENCE: 4
tcactcacca acctcctgtc cttttttaaaa cgccgcagac acat                44

<210> SEQ ID NO 5
<211> LENGTH: 23
<212> TYPE: DNA
<213> ORGANISM: Artificial Sequence
<220> FEATURE:
<223> OTHER INFORMATION: Synthetic primer: HBU-LF

<400> SEQUENCE: 5
ggtgatcccc ctagaaaatt gag                                        23

<210> SEQ ID NO 6
<211> LENGTH: 22
<212> TYPE: DNA
<213> ORGANISM: Artificial Sequence
<220> FEATURE:
<223> OTHER INFORMATION: Synthetic primer: HBU-LR

<400> SEQUENCE: 6
aatttgtcct ggttatcgct gg                                         22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic primer: HCVU-F3

<400> SEQUENCE: 7
gagtgttgta cagcctccag ga                                                  22

<210> SEQ ID NO 8
<211> LENGTH: 18
<212> TYPE: DNA
<213> ORGANISM: Artificial Sequence
<220> FEATURE:
<223> OTHER INFORMATION: Synthetic primer: HCVU-R3

<400> SEQUENCE: 8
attgggcggc ggttggtg                                                       18

<210> SEQ ID NO 9
<211> LENGTH: 44
<212> TYPE: DNA
<213> ORGANISM: Artificial Sequence
<220> FEATURE:
<223> OTHER INFORMATION: Synthetic primer: HCVU-FIP

<400> SEQUENCE: 9
ctcggctagc agtcttgcgg ttttgatgac cgggtccttt cttg                          44

<210> SEQ ID NO 10
<211> LENGTH: 44
<212> TYPE: DNA
<213> ORGANISM: Artificial Sequence
<220> FEATURE:
<223> OTHER INFORMATION: Synthetic primer: HCVU-RIP

<400> SEQUENCE: 10
tagtgttggg tcgcgaaagg cttttcacgg tctacgagac ctcc                          44

<210> SEQ ID NO 11
<211> LENGTH: 20
<212> TYPE: DNA
<213> ORGANISM: Artificial Sequence
<220> FEATURE:
<223> OTHER INFORMATION: Synthetic primer: HCVU-LF

<400> SEQUENCE: 11
gggcattgag cgggttaatc                                                     20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer: HCVU-LR

<400> SEQUENCE: 12
ttgcggtact gcctgatagg                                                     20

<210> SEQ ID NO 13
<211> LENGTH: 18
<212> TYPE: DNA
<213> ORGANISM: Artificial Sequence
<220> FEATURE:
<223> OTHER INFORMATION: Synthetic primer: HCU-F3

<400> SEQUENCE: 13
cgggagagcc atagtggt                                                       18
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic primer: HCU-F3a

<400> SEQUENCE: 14
ggcgacactc caccatagat                                                   20

<210> SEQ ID NO 15
<211> LENGTH: 19
<212> TYPE: DNA
<213> ORGANISM: Artificial Sequence
<220> FEATURE:
<223> OTHER INFORMATION: Synthetic primer: HCU-R3

<400> SEQUENCE: 15
cacggtctac gagacctcc                                                    19

<210> SEQ ID NO 16
<211> LENGTH: 44
<212> TYPE: DNA
<213> ORGANISM: Artificial Sequence
<220> FEATURE:
<223> OTHER INFORMATION: Synthetic primer: HCU-FIP

<400> SEQUENCE: 16
ggcattgagc gggttgatcc aattttttgcg gaaccggtga gtac                       44

<210> SEQ ID NO 17
<211> LENGTH: 44
<212> TYPE: DNA
<213> ORGANISM: Artificial Sequence
<220> FEATURE:
<223> OTHER INFORMATION: Synthetic primer: HCU-RIP

<400> SEQUENCE: 17
cgcgagactg ctagccgagt ttttaccccta tcaggcagta ccac                       44

<210> SEQ ID NO 18
<211> LENGTH: 18
<212> TYPE: DNA
<213> ORGANISM: Artificial Sequence
<220> FEATURE:
<223> OTHER INFORMATION: Synthetic primer: HCU-LF

<400> SEQUENCE: 18
tcgtcctggc aattccgg                                                     18

<210> SEQ ID NO 19
<211> LENGTH: 18
<212> TYPE: DNA
<213> ORGANISM: Artificial Sequence
<220> FEATURE:
<223> OTHER INFORMATION: Synthetic primer: HCU-LR

<400> SEQUENCE: 19
gtgttgggtc gcgaaagg                                                     18

<210> SEQ ID NO 20
<211> LENGTH: 20
<212> TYPE: DNA
<213> ORGANISM: Artificial Sequence
<220> FEATURE:
<223> OTHER INFORMATION: Synthetic primer: HCV1-F3
```

<400> SEQUENCE: 20
ggcgacactc caccatgaat                                        20

<210> SEQ ID NO 21
<211> LENGTH: 22
<212> TYPE: DNA
<213> ORGANISM: Artificial Sequence
<220> FEATURE:
<223> OTHER INFORMATION: Synthetic primer: HCV1-R3

<400> SEQUENCE: 21
ctatcaggca gtaccacaag gc                                     22

<210> SEQ ID NO 22
<211> LENGTH: 43
<212> TYPE: DNA
<213> ORGANISM: Artificial Sequence
<220> FEATURE:
<223> OTHER INFORMATION: Synthetic primer: HCV1-FIP

<400> SEQUENCE: 22
cactatggct ctcccgggag ttttcgtcta gccatggcgt tag               43

<210> SEQ ID NO 23
<211> LENGTH: 44
<212> TYPE: DNA
<213> ORGANISM: Artificial Sequence
<220> FEATURE:
<223> OTHER INFORMATION: Synthetic primer: HCV1-RIP

<400> SEQUENCE: 23
ggaaccggtg agtacaccgg ttttcccaaa tctccaggca ttga              44

<210> SEQ ID NO 24
<211> LENGTH: 19
<212> TYPE: DNA
<213> ORGANISM: Artificial Sequence
<220> FEATURE:
<223> OTHER INFORMATION: Synthetic primer: HCV1-LF

<400> SEQUENCE: 24
aggctgcacg acactcata                                         19

<210> SEQ ID NO 25
<211> LENGTH: 19
<212> TYPE: DNA
<213> ORGANISM: Artificial Sequence
<220> FEATURE:
<223> OTHER INFORMATION: Synthetic primer: HCV1-LR

<400> SEQUENCE: 25
gaccgggtcc tttcttgga                                         19

<210> SEQ ID NO 26
<211> LENGTH: 19
<212> TYPE: DNA
<213> ORGANISM: Artificial Sequence
<220> FEATURE:
<223> OTHER INFORMATION: Synthetic primer: HCV2-F3

<400> SEQUENCE: 26
cgcagaaagc gtctagcca                                         19

<210> SEQ ID NO 27

<210> SEQ ID NO 27
<211> LENGTH: 21
<212> TYPE: DNA
<213> ORGANISM: Artificial Sequence
<220> FEATURE:
<223> OTHER INFORMATION: Synthetic primer: HCV2-R3

<400> SEQUENCE: 27
cgtactcgca agcaccctat c                                            21

<210> SEQ ID NO 28
<211> LENGTH: 45
<212> TYPE: DNA
<213> ORGANISM: Artificial Sequence
<220> FEATURE:
<223> OTHER INFORMATION: Synthetic primer: HCV2-FIP

<400> SEQUENCE: 28
atgaccgggc atagagtggg tttttgtggt ctgcggaacc ggtga                  45

<210> SEQ ID NO 29
<211> LENGTH: 45
<212> TYPE: DNA
<213> ORGANISM: Artificial Sequence
<220> FEATURE:
<223> OTHER INFORMATION: Synthetic primer: HCV2-RIP

<400> SEQUENCE: 29
gcccccgcaa gactgctagc ttttctcgca agcaccctat caggc                  45

<210> SEQ ID NO 30
<211> LENGTH: 20
<212> TYPE: DNA
<213> ORGANISM: Artificial Sequence
<220> FEATURE:
<223> OTHER INFORMATION: Synthetic primer: HCV2-LF

<400> SEQUENCE: 30
aaaggaccca gtcttcccgg                                              20

<210> SEQ ID NO 31
<211> LENGTH: 21
<212> TYPE: DNA
<213> ORGANISM: Artificial Sequence
<220> FEATURE:
<223> OTHER INFORMATION: Synthetic primer: HCV2-LR

<400> SEQUENCE: 31
agcgttgggt tgcgaaaggc c                                            21

<210> SEQ ID NO 32
<211> LENGTH: 20
<212> TYPE: DNA
<213> ORGANISM: Artificial Sequence
<220> FEATURE:
<223> OTHER INFORMATION: Synthetic primer: HCV3-F3

<400> SEQUENCE: 32
cccagaaatt tgggcgtgcc                                              20

<210> SEQ ID NO 33
<211> LENGTH: 19
<212> TYPE: DNA
<213> ORGANISM: Artificial Sequence
<220> FEATURE:
<223> OTHER INFORMATION: Synthetic primer: HCV3-R3

<400> SEQUENCE: 33
ggaacttgac gtcctgtgg                                          19

<210> SEQ ID NO 34
<211> LENGTH: 44
<212> TYPE: DNA
<213> ORGANISM: Artificial Sequence
<220> FEATURE:
<223> OTHER INFORMATION: Synthetic primer: HCV3-FIP

<400> SEQUENCE: 34
gcaagcaccc tatcaggcag tattttcgcg agatcactag ccga              44

<210> SEQ ID NO 35
<211> LENGTH: 43
<212> TYPE: DNA
<213> ORGANISM: Artificial Sequence
<220> FEATURE:
<223> OTHER INFORMATION: Synthetic primer: HCV3-RIP

<400> SEQUENCE: 35
ggaggtctcg tagaccgtgc attttgcgac ggatggtgtt tct               43

<210> SEQ ID NO 36
<211> LENGTH: 19
<212> TYPE: DNA
<213> ORGANISM: Artificial Sequence
<220> FEATURE:
<223> OTHER INFORMATION: Synthetic primer: HCV3-LF

<400> SEQUENCE: 36
ctttcgcgac ccaacacta                                          19

<210> SEQ ID NO 37
<211> LENGTH: 25
<212> TYPE: DNA
<213> ORGANISM: Artificial Sequence
<220> FEATURE:
<223> OTHER INFORMATION: Synthetic primer: HCV3-LR

<400> SEQUENCE: 37
catgagcaca cttcctaaac ctcaa                                   25

<210> SEQ ID NO 38
<211> LENGTH: 22
<212> TYPE: DNA
<213> ORGANISM: Artificial Sequence
<220> FEATURE:
<223> OTHER INFORMATION: Synthetic primer: HIV1-F3

<400> SEQUENCE: 38
acacagtggg gggacatcaa gc                                      22

<210> SEQ ID NO 39
<211> LENGTH: 23
<212> TYPE: DNA
<213> ORGANISM: Artificial Sequence
<220> FEATURE:
<223> OTHER INFORMATION: Synthetic primer: HIV1-R3

<400> SEQUENCE: 39
gtcatccatg ctatttgttc ctg                                     23

<210> SEQ ID NO 40
<211> LENGTH: 24
<212> TYPE: DNA

```
<213> ORGANISM: Artificial Sequence
<220> FEATURE:
<223> OTHER INFORMATION: Synthetic primer: HIV1-R3A

<400> SEQUENCE: 40
tccatgctat ttgttcctga aggg                                              24

<210> SEQ ID NO 41
<211> LENGTH: 24
<212> TYPE: DNA
<213> ORGANISM: Artificial Sequence
<220> FEATURE:
<223> OTHER INFORMATION: Synthetic primer: HIV1-R3B

<400> SEQUENCE: 41
cctgaagggt actagtagtt cctg                                              24

<210> SEQ ID NO 42
<211> LENGTH: 44
<212> TYPE: DNA
<213> ORGANISM: Artificial Sequence
<220> FEATURE:
<223> OTHER INFORMATION: Synthetic primer: HIV1-FIP

<400> SEQUENCE: 42
gatgcaatct atcccattct gttttgccat gcaaatgtta aaag                        44

<210> SEQ ID NO 43
<211> LENGTH: 49
<212> TYPE: DNA
<213> ORGANISM: Artificial Sequence
<220> FEATURE:
<223> OTHER INFORMATION: Synthetic primer: HIV1-FIPA

<400> SEQUENCE: 43
gatgcaatct atcccattct gttttgccat gcaaatgtta aaagagacc                   49

<210> SEQ ID NO 44
<211> LENGTH: 47
<212> TYPE: DNA
<213> ORGANISM: Artificial Sequence
<220> FEATURE:
<223> OTHER INFORMATION: Synthetic primer: HIV1-RIP

<400> SEQUENCE: 44
agtgcatgca gggcctattg cactttgtt cctgctatgt cacttcc                      47

<210> SEQ ID NO 45
<211> LENGTH: 47
<212> TYPE: DNA
<213> ORGANISM: Artificial Sequence
<220> FEATURE:
<223> OTHER INFORMATION: Synthetic primer: HIV1-RIP2

<400> SEQUENCE: 45
agtccatgga gggcctattg cactttgtt cctgctatgt cacttcc                      47

<210> SEQ ID NO 46
<211> LENGTH: 21
<212> TYPE: DNA
<213> ORGANISM: Artificial Sequence
<220> FEATURE:
<223> OTHER INFORMATION: Synthetic primer: HIV1-LF

<400> SEQUENCE: 46
tcagcttcct cattgatggt c                                                 21
```

<210> SEQ ID NO 47
<211> LENGTH: 21
<212> TYPE: DNA
<213> ORGANISM: Artificial Sequence
<220> FEATURE:
<223> OTHER INFORMATION: Synthetic primer: HIV1-LF2

<400> SEQUENCE: 47
cagcttcctc attgatggtc t                                         21

<210> SEQ ID NO 48
<211> LENGTH: 21
<212> TYPE: DNA
<213> ORGANISM: Artificial Sequence
<220> FEATURE:
<223> OTHER INFORMATION: Synthetic primer: HIV1-LR

<400> SEQUENCE: 48
caggccagat gagagaacca a                                         21

<210> SEQ ID NO 49
<211> LENGTH: 20
<212> TYPE: DNA
<213> ORGANISM: Artificial Sequence
<220> FEATURE:
<223> OTHER INFORMATION: Synthetic primer: HEV-F3a

<400> SEQUENCE: 49
cggtggtttc tggggtgaca                                           20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer: HEV-R3

<400> SEQUENCE: 50
gagatagcag tcaacggcgc                                           20

<210> SEQ ID NO 51
<211> LENGTH: 46
<212> TYPE: DNA
<213> ORGANISM: Artificial Sequence
<220> FEATURE:
<223> OTHER INFORMATION: Synthetic primer: HEV-FIP

<400> SEQUENCE: 51
agggcgagct ccagccccgg ttttgccctt cgccctcccc tatatt              46

<210> SEQ ID NO 52
<211> LENGTH: 44
<212> TYPE: DNA
<213> ORGANISM: Artificial Sequence
<220> FEATURE:
<223> OTHER INFORMATION: Synthetic primer: HEV-RIP

<400> SEQUENCE: 52
ccagtcccag cgcccctccg ttttagctgg ggcagatcga cgac                44

<210> SEQ ID NO 53
<211> LENGTH: 20
<212> TYPE: DNA
<213> ORGANISM: Artificial Sequence
<220> FEATURE:

<223> OTHER INFORMATION: Synthetic primer: HEV-LF

<400> SEQUENCE: 53
tgtgaaacga catcggcggc                                          20

<210> SEQ ID NO 54
<211> LENGTH: 20
<212> TYPE: DNA
<213> ORGANISM: Artificial Sequence
<220> FEATURE:
<223> OTHER INFORMATION: Synthetic primer: HEV-LR

<400> SEQUENCE: 54
cgtcgatctg ccccagctgg                                          20

<210> SEQ ID NO 55
<211> LENGTH: 20
<212> TYPE: DNA
<213> ORGANISM: Artificial Sequence
<220> FEATURE:
<223> OTHER INFORMATION: Synthetic primer: WF3

<400> SEQUENCE: 55
ggggccaata cgatttgtgt                                          20

<210> SEQ ID NO 56
<211> LENGTH: 25
<212> TYPE: DNA
<213> ORGANISM: Artificial Sequence
<220> FEATURE:
<223> OTHER INFORMATION: Synthetic primer: WF3a

<400> SEQUENCE: 56
cgatttgtgt tggctctctt ggcgt                                    25

<210> SEQ ID NO 57
<211> LENGTH: 20
<212> TYPE: DNA
<213> ORGANISM: Artificial Sequence
<220> FEATURE:
<223> OTHER INFORMATION: Synthetic primer: WR3

<400> SEQUENCE: 57
aggccaatca tgactgcaat                                          20

<210> SEQ ID NO 58
<211> LENGTH: 46
<212> TYPE: DNA
<213> ORGANISM: Artificial Sequence
<220> FEATURE:
<223> OTHER INFORMATION: Synthetic primer: WFIP

<400> SEQUENCE: 58
ctctccatcg atccagcact gcttttcttg gcgttcttca ggttca             46

<210> SEQ ID NO 59
<211> LENGTH: 45
<212> TYPE: DNA
<213> ORGANISM: Artificial Sequence
<220> FEATURE:
<223> OTHER INFORMATION: Synthetic primer: WRIP

<400> SEQUENCE: 59
actagggacc ttgaccagtg cttttttccg gtctttcctc ctctt              45

```
<210> SEQ ID NO 60
<211> LENGTH: 19
<212> TYPE: DNA
<213> ORGANISM: Artificial Sequence
<220> FEATURE:
<223> OTHER INFORMATION: Synthetic primer: WLF

<400> SEQUENCE: 60
cgggtcggag caattgctg                                                    19

<210> SEQ ID NO 61
<211> LENGTH: 21
<212> TYPE: DNA
<213> ORGANISM: Artificial Sequence
<220> FEATURE:
<223> OTHER INFORMATION: Synthetic primer: WLR

<400> SEQUENCE: 61
tcaatcggcg gagctcaaaa c                                                 21

<210> SEQ ID NO 62
<211> LENGTH: 19
<212> TYPE: DNA
<213> ORGANISM: Artificial Sequence
<220> FEATURE:
<223> OTHER INFORMATION: Synthetic primer: DVF3

<400> SEQUENCE: 62
agcttcatcg tggggatgt                                                    19

<210> SEQ ID NO 63
<211> LENGTH: 20
<212> TYPE: DNA
<213> ORGANISM: Artificial Sequence
<220> FEATURE:
<223> OTHER INFORMATION: Synthetic primer: DVR3

<400> SEQUENCE: 63
ctctcccagc gtcaatatgc                                                   20

<210> SEQ ID NO 64
<211> LENGTH: 44
<212> TYPE: DNA
<213> ORGANISM: Artificial Sequence
<220> FEATURE:
<223> OTHER INFORMATION: Synthetic primer: DVFIP

<400> SEQUENCE: 64 ggagggtct cctctaacca cttttttggct gcaacccatg gaag                        44

<210> SEQ ID NO 65
<211> LENGTH: 45
<212> TYPE: DNA
<213> ORGANISM: Artificial Sequence
<220> FEATURE:
<223> OTHER INFORMATION: Synthetic primer: DVRIP

<400> SEQUENCE: 65
caaaacataa cgcagcagcg ggttttgggg gtctcctcta acctc                       45

<210> SEQ ID NO 66
<211> LENGTH: 19
<212> TYPE: DNA
<213> ORGANISM: Artificial Sequence
<220> FEATURE:
<223> OTHER INFORMATION: Synthetic primer: DVLF
```

-continued

```
<400> SEQUENCE: 66
tgctaccccc tgcgtacag                                              19

<210> SEQ ID NO 67
<211> LENGTH: 19
<212> TYPE: DNA
<213> ORGANISM: Artificial Sequence
<220> FEATURE:
<223> OTHER INFORMATION: Synthetic primer: DVLR

<400> SEQUENCE: 67
caacaccagg ggaagctgt                                              19

<210> SEQ ID NO 68
<211> LENGTH: 19
<212> TYPE: DNA
<213> ORGANISM: Artificial Sequence
<220> FEATURE:
<223> OTHER INFORMATION: Synthetic primer: DF3

<400> SEQUENCE: 68
atggaagctg tacgcatgg                                              19

<210> SEQ ID NO 69
<211> LENGTH: 19
<212> TYPE: DNA
<213> ORGANISM: Artificial Sequence
<220> FEATURE:
<223> OTHER INFORMATION: Synthetic primer: DR3

<400> SEQUENCE: 69
gcgttctgtg cctggaatg                                              19

<210> SEQ ID NO 70
<211> LENGTH: 45
<212> TYPE: DNA
<213> ORGANISM: Artificial Sequence
<220> FEATURE:
<223> OTHER INFORMATION: Synthetic primer: DFIP

<400> SEQUENCE: 70
aggatacagc ttcccctggt gttttgtgg ttagaggaga ccccct                 45

<210> SEQ ID NO 71
<211> LENGTH: 45
<212> TYPE: DNA
<213> ORGANISM: Artificial Sequence
<220> FEATURE:
<223> OTHER INFORMATION: Synthetic primer: DRIP

<400> SEQUENCE: 71
agaggttaga ggagaccccc gttttagcag gatctctggt ctctc                 45

<210> SEQ ID NO 72
<211> LENGTH: 18
<212> TYPE: DNA
<213> ORGANISM: Artificial Sequence
<220> FEATURE:
<223> OTHER INFORMATION: Synthetic primer: D1F3

<400> SEQUENCE: 72
ggctgcaacc catggaag                                               18

<210> SEQ ID NO 73
<211> LENGTH: 20
```

```
<212> TYPE: DNA
<213> ORGANISM: Artificial Sequence
<220> FEATURE:
<223> OTHER INFORMATION: Synthetic primer: D1R3

<400> SEQUENCE: 73
tgcctggaat gatgctgtag                                                 20

<210> SEQ ID NO 74
<211> LENGTH: 44
<212> TYPE: DNA
<213> ORGANISM: Artificial Sequence
<220> FEATURE:
<223> OTHER INFORMATION: Synthetic primer: D1FIP

<400> SEQUENCE: 74
cgctgctgcg ttatgttttg ggttttctgt acgcatgggg tagc                      44

<210> SEQ ID NO 75
<211> LENGTH: 45
<212> TYPE: DNA
<213> ORGANISM: Artificial Sequence
<220> FEATURE:
<223> OTHER INFORMATION: Synthetic primer: D1RIP

<400> SEQUENCE: 75
agaggttaga ggagaccccc gttttagcag gatctctggt ctctc                     45

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 22
<212> TYPE: DNA
<213> ORGANISM: Artificial Sequence
<220> FEATURE:
<223> OTHER INFORMATION: Synthetic primer: HIV1-F3A
```

```
<400> SEQUENCE: 81
aacaccatgc taaacacagt gg                                                      22
```

METHODS FOR RAPID DETECTION AND IDENTIFICATION OF VIRAL NUCLEIC ACIDS

This application is a continuation of U.S. application Ser. No. 14/671,859, filed Mar. 27, 2015, which claims the benefit of and priority to U.S. Provisional Patent Application Ser. No. 61/979,446, filed Apr. 14, 2014, both of the above-identified applications are incorporated by reference in their entireties for all purposes.

REFERENCE TO SEQUENCE LISTING SUBMITTED VIA EFS-WEB

This application includes an electronically submitted sequence listing in .txt format. The .txt file contains a sequence listing entitled "2015-10-21 1464.8004_ST25.txt" created on Oct. 21, 2015 and is 15,591 bytes in size. The sequence listing contained in this .txt file is part of the specification and is hereby incorporated by reference herein in its entirety.

FIELD

This disclosure relates to methods for detecting human immunodeficiency virus, hepatitis virus, Dengue virus, and West Nile virus nucleic acids, particularly using isothermal amplification methods.

BACKGROUND

Hepatitis B virus (HBV), hepatitis C virus (HCV), and the emerging hepatitis E virus (HEV) together infect approximately 700 million people world-wide and may lead to chronic active hepatitis or hepatocellular carcinoma. Infection with human immunodeficiency virus (HIV) compromises the immune system, while Dengue virus (DENV) causes hemorrhagic fever and West Nile virus (WNV) can cause encephalitis and other neuroinflammatory symptoms. Infection with these viruses causes significant morbidity and mortality worldwide. Furthermore, as these viruses are transmitted primarily by blood-borne routes, the presence of infected individuals in the population raises the risk of blood or blood-products from infected donors being transfused to uninfected individuals.

SUMMARY

There is a continuing need for rapid, sensitive, and specific assays for HIV, HBV, HCV, HEV, DENV, and WNV, both for diagnosis (and clinical intervention) for infected individuals and to ensure the safety of the blood and blood-products supply. Disclosed herein are methods of detecting HIV, HBV, HCV, HEV, DENV, and/or WNV in a sample. In some embodiments, the methods include loop-mediated isothermal amplification (LAMP) or reverse transcription-LAMP (RT-LAMP) methods to detect viral nucleic acids in a sample. The disclosed methods include individual detection assays (such as singleplex assays) as well as simultaneous detection and/or discrimination of two or more viral nucleic acids (such as multiplex assays).

Disclosed herein are methods of detecting viral nucleic acids in a sample that include contacting the sample with one or more sets of LAMP primers specific for a viral nucleic acid of interest (such as HBV, HCV, HEV, HIV, WNV, and/or DENV nucleic acids) under conditions sufficient to produce an amplification product and detecting the amplification product(s). In some examples, the amplification product is detected by gel electrophoresis, while in other examples, the amplification product is detected by detecting signal from a nucleic acid stain (such as a DNA intercalating dye) or a detectable label included in one or more of the LAMP primers.

Primers for detecting viral nucleic acids by LAMP are disclosed herein. In some examples, the primers include primers for detection of HBV nucleic acids (such as SEQ ID NOs: 1-6), HCV (such as SEQ ID NOs: 13-37), HIV (such as SEQ ID NOs: 38-48 and 81), HEV (such as SEQ ID NOs: 49-54), WNV (such as SEQ ID NOs: 55-61), and DENV (such as SEQ ID NOs: 62-75) are provided. Kits including one or more sets of LAMP primers are also disclosed herein.

The foregoing and other features of the disclosure will become more apparent from the following detailed description, which proceeds with reference to the accompanying figures.

BRIEF DESCRIPTION OF THE DRAWINGS

At least some of the following figures are submitted in color.

FIG. 1 shows a partial sequence of HBV genomic sequence (SEQ ID NO: 76) and the position of the universal HBV LAMP primers.

FIG. 2A is a digital image of gel electrophoresis of reaction products.

FIG. 3A is a digital image of gel electrophoresis of reaction products showing detection to about 10 International Units (IU) of HBV DNA (~50 copies). Lane M=100 bp Marker; NTC=No Template (water) Control. FIG. 3B is a digital image of reaction tubes with the addition of GelGreen fluorescent dye, showing a fluorescent-glow with decreasing intensity from 10 to 0.1 IU/reaction. FIG. 3C is a digital image of gel eletrophoresis of reaction products with DNA extracted from Cytomegalovirus (CMV)-positive and Parvovirus (PV)-positive donor plasma specimens and subjected to HBV LAMP reaction. Lane M=100 bp DNA ladder; Lane 1=NTC (no template control); Lanes 2 and 3=CMV DNA; Lanes 4 and 5=PV DNA; Lanes 6 and 7=HBV-A DNA. FIG. 3D is a digital image of gel electrophoresis of reaction products from HBV LAMP reaction using DNA of *L. cruzi* (lanes 3 and 4), *L. major*, (lanes 5 and 6), and *L. tropica* (lanes 7 and 8) DNA. Lane 1=100 bp marker; Lane 2=NTC (no template control); Lane 3=NP (negative human plasma); Lanes 9-10=HBV-A DNA; Lanes 11-12=HBV-B DNA.

FIG. 4A is a digital image of gel electrophoresis of DNA extracted from donor plasma specimens subjected to HBV LAMP.

FIGS. 6A-C are a series of panels showing stability of mannitol acetate reaction buffer (MAB). FIG. 6A is a digital image of gel electrophoresis of HBV LAMP using fresh buffer (stored at −20° C.). FIG. 6B is a digital image of gel electrophoresis of HBV LAMP using room temperature-stored buffer. FIG. 6C is a digital image of gel electrophoresis of HBV LAMP using thermo-stressed MAB.

FIGS. 7A-D are HCV nucleic acid sequences used to design HCV primer sets. FIG. 7A is an HCV-4a nucleic acid sequence (SEQ ID NO: 77) used to design the HCV universal primer set (GenBank Accession No. Y11604). FIG. 7B is an HCV-1a nucleic acid sequence (SEQ ID NO: 78) used to design the HCV-1 primer set (GenBank Accession No. AF009606). FIG. 7C is an HCV-2a nucleic acid sequence (SEQ ID NO: 79) used to design the HCV-2 primer set (GenBank Accession No. AF333324). FIG. 7D is an HCV-3a nucleic acid sequence (SEQ ID NO: 80) used to design the HCV-3 primer set (GenBank Accession No. D17763). For each, underlined nucleic acids indicate sequences included in primers.

FIG. 8A is a digital image of gel electrophoresis of RT-LAMP reaction products using total RNA extracted from plasma standards of HCV genotypes 1, 2, and 4. Lane M=100 bp marker, Lane 1=No-Template Control (NTC); Lane 2: W=West Nile Virus ($2.85 \times 10^6$ copies/rxn); Lane 3: HCV-1a ($10^6$ IU/rxn); Lane 4: HCV-1b ($5 \times 10^5$ IU/rxn); Lane 5: HCV-2a ($5 \times 10^4$ IU/rxn); Lane 6: HCV-2a/c ($5 \times 10^5$ IU/rxn); and, Lane 7: HCV-4a (180 IU/rxn).

FIGS. 9 A-D are digital images of electrophoresis of reaction products of RT-LAMP assays with HCV genotype-specific primer sets.

FIGS. 10A-C are digital images showing detection of known amounts of HCV plasma standard or extracted RNA with HCV universal primer RT-LAMP assay. FIG. 10A shows gel electrophoresis of reaction products of serial dilutions of heat-treated HCV genotype 1a plasma standard. Lane M=100 bp marker; NTC=No-Template Control; NP=Negative Human Plasma; D=Dengue Virus RNA ($5 \times 10^6$ copies/rxn); W=West Nile virus RNA ($5 \times 10^6$ copies/reaction). FIG. 10B shows gel electrophoresis of reaction products of serial dilutions of extracted RNA of HCV genotype 1a. FIG. 10C is a digital image of reactions with addition of GelGreen dye to the final reaction tubes and visualized under UV illumination at 302 nm. Tubes correspond to the lanes in FIG. 10B.

FIGS. 11A-C shows detection of HCV in total RNA extracted from donor plasma or serum specimens with HCV LAMP primers sets. FIG. 11A shows gel electrophoresis of reaction products from donor plasma samples of unknown genotype with HCV-1 LAMP primer set. FIG. 11B shows gel electrophoresis of reaction products from the same samples as in FIG. 11A with HCV-2 LAMP primer set. FIG. 11C shows gel electrophoresis of reaction products from known HCV-4a-infected donor serum samples with universal HCV LAMP primer set. All panels: Lane M=100 bp marker; Lane NTC=No Template (water) control; Lanes NC and D=Negative Control Dengue Virus RNA ($5 \times 10^6$ copies/rxn); Panel A: Lane PC=Positive Control HCV-1a (~$10^3$ IU/rxn); Panel B: Lane PC=Positive Control HCV-2a (~$10^4$ IU/rxn); Panel C: Lane H=Positive Control HCV-4a (180 IU/rxn).

FIG. 16A shows gel electrophoresis of reaction products using HEV-3 (Kernow C-1 strain). NTC=no template control; 10-fold (3 ng) and 100-fold (1.5 ng) dilutions of HEV.

FIG. 17A shows gel electrophoresis of reaction products from a multiplex LAMP assay including both HBV universal primer set and HCV universal primer set. M: 100 bp marker; Lane 1: no template control; Lane 2: DENV; Lane 3: WNV; Lanes 4-5: HBV; Lanes 6-7: HCV. FIG. 17B shows gel electrophoresis of reaction products from a multiplex LAMP assay including HBV, HCV, and WNV primer sets. M: 100 bp marker; Lane 1: no template control; Lane 2: DENV; Lanes 3-4: HBV; Lanes 5-6: HCV; Lanes 7-8: WNV. FIG. 17C shows gel electrophoresis of reaction products from a multiplex LAMP assay including HBV, HCV, HIV, and HEV primer sets. Each reaction contained RNA from the indicated viruses. FIG. 17D shows gel electrophoresis of reaction products from a multiplex LAMP assay including HIV, HBV, HCV, HEV, DENV, and WNV primer sets. M: 100 bp marker; NTC: no template control; PV: parvovirus; CMV: cytomegalovirus.

FIG. 18A is a digital image of a multiplex LAMP assay with HBV, HCV, and HIV primer sets with HCV fluoro-oligo, detected by gel electrophoresis (top) or UV illumination (bottom). Numbers on the tubes indicate relative fluorescence units (RFU) for each sample. The HCV fluoro-oligo was SEQ ID NO: 12 labeled with TexasRed (5') and BHQ1 (3'). FIG. 18B is a digital image of a multiplex LAMP assay with HBV, HCV, HEV and HIV primer sets with HIV fluoro-oligo, detected by gel electrophoresis (top) or UV illumination (bottom). Numbers on the tubes indicate relative fluorescence units (RFU) for each sample. The HIV fluoro-oligo was SEQ ID NO: 48 labeled with 6-FAM (5') and BHQ1 (3'). FIG. 18C is a digital image of a multiplex LAMP assay with HBV, HCV, HEV, and HIV primer sets with HCV fluoro-oligo and HIV fluoro-oligo, detected by gel electrophoresis (top) or UV illumination (bottom). Numbers on the tubes indicate relative fluorescence units (RFU) for each sample. The fluoro-oligos were labeled with 6-FAM (5') and BHQ1 (3').

SEQUENCES

Figures 2A, 2B:
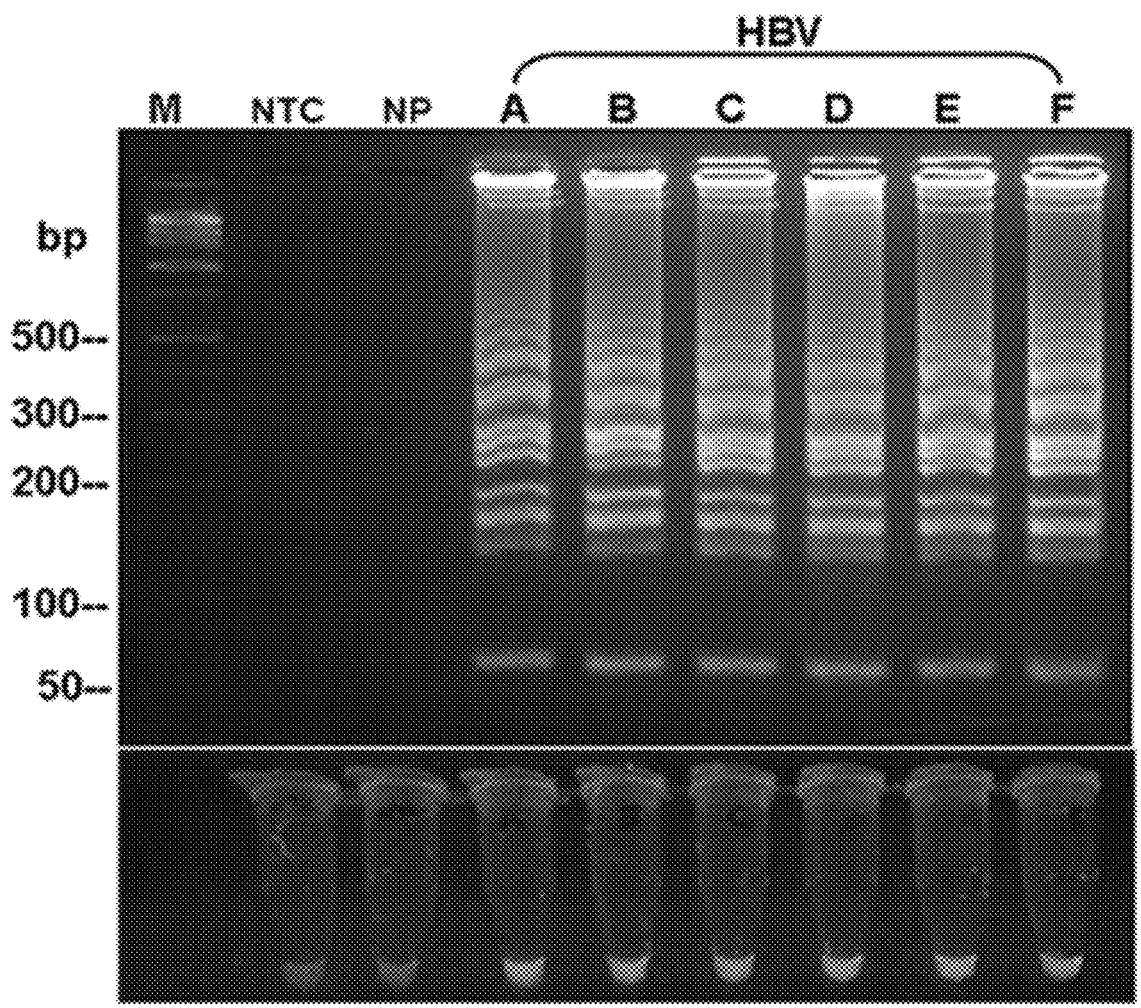
FIGS. 2A and B show detection of HBV genotypes A-F with LAMP using the HBV universal primer set.
FIG. 2B is a digital image of reaction tubes with addition of GelGreen fluorescent dye under ultraviolet (UV) light. Lane M=50 bp Marker; Lanes A-F=HBV genotypes A to F; NTC=No template (water) control; NP=Negative plasma.

Any nucleic acid and amino acid sequences listed herein are shown using standard letter abbreviations for nucleotide bases and amino acids, as defined in 37 C.F.R § 1.822. In at least some cases, only one strand of each nucleic acid sequence is shown, but the complementary strand is understood as included by any reference to the displayed strand.

SEQ ID NOs: 1-6 are nucleic acid sequences of exemplary universal HBV LAMP primers.

SEQ ID NOs: 7-12 are nucleic acid sequences of exemplary universal HCV LAMP primers.

SEQ ID NOs: 13-19 are nucleic acid sequences of alternative universal HCV LAMP primers.

SEQ ID NOs: 20-25 are nucleic acid sequences of exemplary HCV-1 LAMP primers.

SEQ ID NOs: 26-31 are nucleic acid sequences of exemplary HCV-2 LAMP primers.

SEQ ID NOs: 32-37 are nucleic acid sequences of exemplary HCV-3 LAMP primers.

SEQ ID NOs: 38-48 and 81 are nucleic acid sequences of exemplary HIV-1 LAMP primers.

SEQ ID NOs: 49-54 are nucleic acid sequences of exemplary HEV LAMP primers.

SEQ ID NOs: 55-61 are nucleic acid sequences of exemplary WNV LAMP primers.

SEQ ID NOs: 62-75 are nucleic acid sequences of exemplary DENV LAMP primers.

SEQ ID NO: 76 is the nucleic acid sequence of a partial HBV genomic sequence.

SEQ ID NOs: 77-80 are HCV nucleic acid sequences.

DETAILED DESCRIPTION

I. Abbreviations

DENV Dengue virus
HBV hepatitis B virus
HCV hepatitis C virus
HEV hepatitis E virus
HIV human immunodeficiency virus
IU international units
LAMP loop-mediated isothermal amplification
MAB mannitol acetate buffer
NCR non-coding region
RFU relative fluorescence units
RT reverse transcriptase
RT-LAMP reverse transcription-loop-mediated isothermal amplification
UV ultraviolet
WNV West Nile virus II. Terms Unless otherwise noted, technical terms are used according to conventional usage. Definitions of common terms in molecular biology may be found in *Lewin's Genes X*, ed. Krebs et al, Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with GenBank Accession Nos. mentioned herein are incorporated by reference in their entirety as were present on Apr. 14, 2014, to the extent permissible by applicable rules and/or law. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of this disclosure, the following explanations of specific terms are provided:

Amplification: Increasing the number of copies of a nucleic acid molecule, such as a gene or fragment of a gene, for example at least a portion of an HIV, HBV, HCV, DENV, or WNV nucleic acid molecule. The products of an amplification reaction are called amplification products. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include real-time PCR, quantitative real-time PCR (qPCR), reverse transcription PCR (RT-PCR), quantitative RT-PCR (qRT-PCR), loop-mediated isothermal amplification (LAMP; see Notomi et al., *Nucl. Acids Res.* 28:e63, 2000); reverse-transcriptase LAMP (RT-LAMP); strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Conditions sufficient for: Any environment that permits the desired activity, for example, that permits specific binding or hybridization between two nucleic acid molecules or that permits reverse transcription and/or amplification of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), and so on).

Contact: Placement in direct physical association; for example in solid and/or liquid form. For example, contacting can occur in vitro with one or more primers and/or probes and a biological sample (such as a sample including nucleic acids) in solution.

Dengue virus (DENV): Dengue virus (DENV) is a mosquito-borne flavivirus including four serotypes (DENV-1, DENV-2, DENV-3, and DENV-4). It is estimated that as many as 400 million individuals are infected with DENV yearly worldwide and over 100 million cases of Dengue fever occur annually. DENV infection causes Dengue fever with symptoms including high fever, severe headache, severe joint, muscle, and bone pain, and rash. DENV also cause Dengue hemorrhagic fever, characterized by a fever lasting 2-7 days, followed by persistent vomiting, severe abdominal pain, and hemorrhagic manifestations, including ascites, pleural effusions, or hemorrhagic shock. Dengue hemorrhagic fever may arise when an individual previously infected with one DENV serotype is infected with another DENV serotype and antibody-dependent enhancement occurs due to the presence of cross-reactive but non-neutralizing antibodies.

DENV nucleic acid and protein sequences are available in public databases, including GenBank. Exemplary DENV sequences include GenBank Accession Nos. NC_001477, AF180817, and U88536 (DEN-1); NC_001474 and U87411 (DEN-2); NC_001475, AY099336, and AF317645 (DEN-3); and NC_002640 and AF326825 (DEN-4), all of which are incorporated by reference as included in GenBank on Apr. 14, 2014.

Detectable label: A compound or composition that is conjugated directly or indirectly to another molecule (such as a nucleic acid molecule) to facilitate detection of that molecule. Specific, non-limiting examples of labels include fluorescent and fluorogenic moieties (e.g., fluorophores), chromogenic moieties, haptens (such as biotin, digoxigenin, and fluorescein), affinity tags, and radioactive isotopes (such as $^{31}$P, $^{33}$P, $^{35}$S, and $^{125}$I). The label can be directly detectable (e.g., optically detectable) or indirectly detectable (for example, via interaction with one or more additional molecules that are in turn detectable). Methods for labeling nucleic acids, and guidance in the choice of labels useful for various purposes, are discussed, e.g., in Sambrook and Russell, in *Molecular Cloning: A Laboratory Manual*, 3$^{rd}$ Ed., Cold Spring Harbor Laboratory Press (2001) and Ausubel et al., in *Current Protocols in Molecular Biology*, Greene Publishing Associates and Wiley-Intersciences (1987, and including updates).

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes and primers disclosed herein are known to those of skill in the art and include 4-acetamido-4'-isothiocyanatostilbene-2,2'disulfonic acid; acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 27'-dimethoxy-4'5'-dichloro-6-carboxyfluorescein (JOE), fluorescein, fluorescein isothiocyanate (F1TC), QFITC (XRITC), 6-carboxy-fluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CalRed 590, CalRed 610, CalRed615, CalRed 635, CalGreen 520, CalGold 540, and CalOrange 560 (Biosearch Technologies, Novato, Calif.). One skilled in the art can select additional fluorophores, for example those available from Molecular Probes/Life Technologies (Carlsbad, Calif.).

In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Biosearch Technologies; such as BHQ0, BHQ1, BHQ2, and BHQ3), ECLIPSE™ Dark Quencher (Epoch Biosciences), or IOWA BLACK™ (Integrated DNA Technologies). A quencher can reduce or quench the emission of a donor fluorophore.

"Donor Fluorophores" are fluorophores or luminescent molecules capable of transferring energy to an acceptor fluorophore, in some examples generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $103 \, M^{-1} \, cm^{-1}$.

Hepatitis B virus (HBV): HBV is a DNA virus with a circular genome of partially double-stranded DNA that is a member of the family Hepadnaviridae. HBV causes acute disease, characterized by liver inflammation, vomiting, and jaundice, as well as chronic infection which may lead to cirrhosis or hepatocellular carcinoma. HBV infection may be asymptomatic.

There are eight genotypes of HBV (A-H), HBV-A is most commonly found in the Americas, Africa, India, and Western Europe, HBV-B and HBV-C are most commonly found in Asia and the United States and HBV-D most commonly found in Southern Europe, India, and the United States. The HBV genotypes differ by at least 8% of their sequence across the genome (Okamoto et al., *J. Gen. Virol.* 69:2575-2583, 1988). HBV nucleic acid and protein sequences are available in public databases, including GenBank. Exemplary HBV sequences include GenBank Accession No. AB116094 (HBV genotype A), which is incorporated by reference herein as present in GenBank on Apr. 14, 2014. One of skill in the art can identify additional HBV sequences.

Hepatitis C virus (HCV): HCV is a single-stranded positive strand RNA virus that is a member of the family Flaviviridae. HCV is transmitted primarily by blood-borne routes, including intravenous drug use and transfusions. Acute HCV infection has generally mild symptoms, which frequently resolves spontaneously. About 80% of infected individuals develop chronic infection which is generally asymptomatic initially, but eventually can lead to cirrhosis or hepatocellular carcinoma.

There are at least seven genotypes of HCV (1-7), with subtypes within each genotype (indicated by lower case letters). HCV genotypes 1a and 1b are the most common worldwide. HCV responsiveness to therapy varies by genotype, with genotypes 1 and 4 being less responsive to interferon-based therapy than genotypes 2 and 3. HCV nucleic acid and protein sequences are available in public databases, including GenBank. Exemplary HCV sequences include GenBank Accession Nos. Y11604 (HCV-4), AF009606 (HCV-1), AF333324 (HCV-2), and D17763 (HCV-3), all of which are incorporated by reference herein as present in GenBank on Apr. 14, 2014. One of skill in the art can identify additional HCV sequences.

Hepatitis E virus (HEV): HEV is a non-enveloped single-stranded positive sense RNA virus that is a member of the family Hepeviridae. HEV is transmitted by the fecal-oral route. HEV causes an acute and self-limiting infection in most cases. Immunocompromised or immunosuppressed individuals, such as organ transplant recipients are at highest risk for chronic HEV infection. It is most prevalent in India, Southeast Asia, north-central Africa, and Central America.

There are four known genotypes of HEV (1-4). HEV nucleic acid and protein sequences are available in public databases, including GenBank. Exemplary HEV sequences include GenBank Accession No. HQ389543, which is incorporated by reference herein as present in GenBank on Apr. 14, 2014. One of skill in the art can identify additional HEV sequences.

Human Immunodeficiency virus (HIV): HIV is a retrovirus that causes immunosuppression in humans (HIV disease), and leads to disease states known as acquired immunodeficiency syndrome (AIDS) and AIDS related complex (ARC). "HIV disease" refers to a well-recognized constellation of signs and symptoms (including the development of opportunistic infections) in persons who are infected by an HIV virus, as determined by antibody or western blot studies or detection of HIV nucleic acids. Laboratory findings associated with this disease are a progressive decline in T cells. HIV includes HIV type 1 (HIV-1) and HIV type 2 (HIV-2). Related viruses that are used as animal models include simian immunodeficiency virus (SIV) and feline immunodeficiency virus (FIV).

HIV nucleic acid and protein sequences are available in public databases, including GenBank and the HIV Database (available on the World Wide Web at www.hiv.lanl.gov/). Exemplary reference sequences include HXB2 for HIV-1 (e.g., GenBank Accession Nos. K03455 or M38432) and MAC239 for HIV-2 (GenBank Accession No. M33262). One of skill in the art can identify additional HIV sequences.

Isolated: An "isolated" biological component (such as a nucleic acid) has been substantially separated or purified away from other biological components in which the component naturally occurs, such as other chromosomal and extrachromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Loop-mediated isothermal amplification (LAMP): A method for amplifying DNA. The method is a single-step amplification reaction utilizing a DNA polymerase with strand displacement activity (e.g., Notomi et al., *Nucl. Acids. Res.* 28:E63, 2000; Nagamine et al., *Mol. Cell. Probes* 16:223-229, 2002; Mori et al., *J. Biochem. Biophys. Methods* 59:145-157, 2004). At least four primers, which are specific for eight regions within a target nucleic acid sequence, are typically used for LAMP. The primers include a forward outer primer (F3), a reverse outer primer (R3), a forward inner primer (FIP), and a reverse inner primer (RIP). A forward loop primer (LF), and a reverse loop primer (LR) can also be included in some embodiments. The amplification reaction produces a stem-loop DNA with inverted repeats of the target nucleic acid sequence. Reverse transcriptase can be added to the reaction for amplification of RNA target sequences. This variation is referred to as RT-LAMP.

Primer: Primers are short nucleic acids, generally DNA oligonucleotides 10 nucleotides or more in length (such as 12, 15, 18, 20, or more nucleotides in length). Primers may be annealed to a complementary target DNA strand by nucleic acid hybridization to form a hybrid between the primer and the target DNA strand, and then extended along the target DNA strand by a DNA polymerase enzyme. In some examples, primer pairs can be used for amplification of a nucleic acid sequence, e.g., by the polymerase chain reaction (PCR) or other nucleic acid amplification methods known in the art.

Probe: A probe typically comprises an isolated nucleic acid (for example, at least 10 or more nucleotides in length) with an attached detectable label or reporter molecule. Typical labels include radioactive isotopes, ligands, chemiluminescent agents, fluorophores, and enzymes. Methods for labeling oligonucleotides and guidance in the choice of labels appropriate for various purposes are discussed, e.g., in Sambrook et al. (2001) and Ausubel et al. (1987).

Sample (or biological sample): A biological specimen containing DNA (for example, genomic DNA or cDNA), RNA (including mRNA), protein, or combinations thereof. Examples include, but are not limited to isolated nucleic acids, cells, cell lysates, chromosomal preparations, peripheral blood, serum, plasma, urine, saliva, tissue biopsy (such as a tumor biopsy or lymph node biopsy), surgical specimen, bone marrow, amniocentesis samples, and autopsy material. In one example, a sample includes viral nucleic acids, for example, viral DNA, viral RNA, or cDNA reverse transcribed from viral RNA. In particular examples, samples are used directly (e.g., fresh or frozen), or can be manipulated prior to use, for example, by fixation (e.g., using formalin) and/or embedding in wax (such as FFPE tissue samples).

Subject: Any multi-cellular vertebrate organism, such as human and non-human mammals (including non-human primates). In one example, a subject is known to be or is suspected of being infected with one or more viruses.

West Nile virus (WNV): A member of the Japanese encephalitis serocomplex in the genus Flavivirus, family Flaviviridae. WNV is most commonly transmitted to humans by mosquitoes, but can also be transmitted through blood transfusions, organ transplants, and from mother to baby during pregnancy, delivery, or breastfeeding. In nature, WNV cycles between mosquitoes and birds and can be transmitted to humans, horses, and other mammals through bite by an infected mosquito. Until the mid-1990s, WNV caused sporadic outbreaks of illness in Africa, the Middle East, and Western Asia. However, since 1996, WN encephalitis has been reported more frequently in Europe, the Middle East, northern and western Africa, and Russia. WNV emerged in the western hemisphere in 1999. Most people infected with WNV do not develop any symptoms. About 20% of infected individuals develop a fever with headache, body aches, joint pain, vomiting, diarrhea, or rash. Less than 1% of infected individuals develop encephalitis or meningitis, which can result in permanent neurological damage or death (about 10% of those with neurologic infection).

WNV nucleic acid and protein sequences are available in public databases, including GenBank. WNV sequences include GenBank Accession Nos.: AY278441, AF202541, AF404754, AF260967, AY660002, AF481864, AY268133, AF404757, and AY277251, all of which are incorporated by reference as included in GenBank on Apr. 14, 2014. One of skill in the art can identify additional WNV sequences.

III. Methods of Detecting Viral Nucleic Acids

Disclosed herein are methods of detecting viral nucleic acids in a sample (such as a sample from a subject infected with or suspected to be infected with a virus). The disclosed methods include LAMP or RT-LAMP assays for detection of viral nucleic acids in a sample, including one or more of HBV, HCV, HEV, HIV, WNV, and/or DENV nucleic acids. In some examples, the methods include detecting HBV in a sample and/or discriminating HBV genotypes (for example detecting and/or discriminating HBV-A, HBV-B, HBV-C, HBV-D, HBV-E, or HBV-F). In other examples, the methods include detecting HCV in a sample and/or discriminating HCV genotypes, for example detecting and/or discriminating HCV-1 (such as HCV-1a, HCV-1b, or HCV-1c), HCV2 (such as HCV-2a, HCV-2b, or HCV-2c), HCV3 (such as HCV-3a or HCV-3b), or HCV4 (such as HCV-4a). In further examples, the methods include detecting HEV (such as HEV-1 or HEV-3) in a sample. In other examples, the methods include detecting HIV in a sample (such as HIV-1). In additional examples, the methods include detecting WNV in a sample or detecting DENV in a sample (for example detecting and/or discriminating DEN-1, DEN-2, DEN-3, or DEN-4). Primers and probes for use in the disclosed methods are provided herein.

The methods described herein may be used for any purpose for which detection of viral nucleic acids, such as HBV, HCV, HEV, HIV, WNV, or DENV nucleic acids, is desirable, including diagnostic and prognostic applications, such as in laboratory and clinical settings. Appropriate samples include any conventional biological samples, including clinical samples obtained from a human or veterinary subject. Suitable samples include all biological samples useful for detection of infection in subjects, including, but not limited to, cells (such as buccal cells or peripheral blood mononuclear cells), tissues, autopsy samples, bone marrow aspirates, bodily fluids (for example, blood, serum, plasma, urine, cerebrospinal fluid, middle ear fluids, bronchoalveolar lavage, tracheal aspirates, sputum, nasopharyngeal aspirates, oropharyngeal aspirates, or saliva), oral swabs, eye swabs, cervical swabs, vaginal swabs, rectal swabs, stool, and stool suspensions. The sample can be used directly or can be processed, such as by adding solvents, preservatives, buffers, or other compounds or substances. In some examples, nucleic acids are isolated from the sample. In other examples, isolation of nucleic acids from the sample is not necessary prior to use in the methods disclosed herein and the sample (such as a plasma or serum sample) is used directly. In further examples, the sample is pre-treated with a lysis buffer, but nucleic acids are not isolated prior to use in the disclosed methods.

Samples also include isolated nucleic acids, such as DNA or RNA isolated from a biological specimen from a subject, a viral isolate, or other source of nucleic acids. Methods for extracting nucleic acids such as RNA or DNA from a sample are known to one of skill in the art; such methods will depend upon, for example, the type of sample in which the nucleic acid is found. Nucleic acids can be extracted using standard methods. For instance, rapid nucleic acid preparation can be performed using a commercially available kit (such as kits and/or instruments from Qiagen (such as QiaAmp®, DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162: 156-159, 1987).

The disclosed methods are highly sensitive and/or specific for detection of HBV, HCV, HIV, HEV, WNV, and DENV nucleic acids. In some examples, the disclosed methods can detect presence of at least 1 International Unit (IU; about 5 copies) of HBV, HCV, or HEV nucleic acids (for example at least 10, 25, 50, $10^2$, $10^3$, $10^4$, $10^5$, $10^6$, or more IU of HBV, HCV, or HEV nucleic acids) in a sample or reaction volume. In other examples, the disclosed methods can detect presence of at least 1 copy of HBV, HCV, HEV, HIV, WNV, or DENV nucleic acids (for example at least 10, 25, 50, $10^2$, $10^3$, $10^4$, $10^5$, $10^6$, or more copies) in a sample or reaction volume. In some examples, the disclosed methods can predict with a sensitivity of at least 75% and a specificity of at least 75% for presence of one or more of HBV, HCV, HEV, HIV, WNV, or DENV nucleic acids in a sample, such as a sensitivity of at least 80%, 85%, 90%, 95%, or even 100% and a specificity of at least of at least 80%, 85%, 90%, 95%, or even 100%.

In some embodiments, the methods for detecting viral nucleic acids in a sample utilize LAMP or RT-LAMP methods of amplification and detection. LAMP is a one-step isothermal amplification method that can produce amplified nucleic acids in a short period of time using a DNA polymerase with strand displacement activity (see, e.g., Notomi et al., *Nucl. Acids Res.* 28:e63, 2000). LAMP can be used for amplification of RNA targets with the addition of reverse transcriptase (RT) to the reaction without an additional heat step (referred to as RT-LAMP). The isothermal nature of LAMP and RT-LAMP allows for assay flexibility because it can be used with simple and inexpensive heating devices, which can facilitate viral detection in settings other than centralized clinical laboratories. In addition, LAMP and RT-LAMP assays are rapid, specific, and sensitive.

LAMP or RT-LAMP can also be multiplexed through the addition of multiple LAMP primer sets with different specificities in a single reaction vessel (such as a tube, well, or other container). This capability is advantageous, for example, because it allows for incorporation of internal control(s), amplification of two or more regions within the same target, or detection of two or more targets or pathogens in a single reaction. In some examples, the disclosed methods include a multiplex LAMP or RT-LAMP assay for detection and/or discrimination of one or more of HBV, HCV, HEV, HIV, WNV, and DENV in a single reaction.

The sample and LAMP primer set(s) are contacted under conditions sufficient for amplification of a viral nucleic acid, producing an amplification product. The sample is contacted with the set of LAMP primers at a concentration sufficient to support amplification of the particular viral nucleic acid for the LAMP primer set. In some examples, the amount of each primer is about 0.1 µM to about 5 µM (such as about 0.2 µM to about 2 µM, or about 0.5 µM to about 2 µM). Each primer can be included at a different concentration, and appropriate concentrations for each primer can be selected by one of skill in the art using routine methods. Exemplary primer concentrations are provided in Examples 2-5, below.

In some examples, the LAMP or RT-LAMP reaction is carried out in a mixture including a suitable buffer (such as a phosphate buffer or Tris buffer). The buffer may also include additional components, such as salts (such as KCl or NaCl, magnesium salts (e.g., $MgCl_2$ or $MgSO_4$), ammonium (e.g., $(NH_4)_2SO_4$)), detergents (e.g., TRITON®-X100), or other additives (such as betaine or dimethylsulfoxide). The buffer or reaction mixture also includes nucleotides or nucleotide analogs. In some examples, an equimolar mixture of dATP, dCTP, dGTP, and dTTP (referred to as dNTPs) is included, for example about 0.5-5 mM dNTPs (such as about 1-3 mM dNTPs). In one example, the buffer is MAB buffer, described in Section IV. In other examples, the buffer is Loopamp® reaction mix (Eiken Chemical Co., Ltd., Tochigi, Japan) or another commercially available polymerase or RT reaction buffer. One of skill in the art can select an appropriate buffer and any additives using routine methods.

A DNA polymerase with strand displacement activity is also included in the reaction mixture. Exemplary DNA polymerases include Bst DNA polymerase, Bst 2.0 DNA polymerase, Bst 2.0 WarmStart™ DNA polymerase (New England Biolabs, Ipswich, Mass.), Phi29 DNA polymerase, Bsu DNA polymerase, OmniAmp™ DNA polymerase (Lucigen, Middleton, Mich.), Taq DNA polymerase, Vent® and Deep Vent$_R$® DNA polymerases (New England Biolabs), 9° N$_m$™ DNA polymerase (New England Biolabs), Klenow fragment of DNA polymerase I, PhiPRD1 DNA polymerase, phage M2 DNA polymerase, T4 DNA polymerase, and T5 DNA polymerase. In some examples, about 1 to 20 U (such as about 1 to 15 U, about 2 to 12 U, about 10 to 20 U, about 2 to 10 U, about 5 to 10 U, or 8 U) of DNA polymerase is included in the reaction. In some examples, the polymerase has strand displacement activity and lacks 5'-3' exonuclease activity. In one non-limiting example, the DNA polymerase is Bst DNA polymerase.

In some embodiments, the target nucleic acid is DNA (such as an HBV nucleic acid). In other embodiments, the target nucleic acid is RNA (such as an HCV nucleic acid, an HEV nucleic acid, an HIV nucleic acid, a WNV nucleic acid, or a DENV nucleic acid), and a reverse transcriptase is additionally included in the LAMP assay (called an RT-LAMP assay). Exemplary reverse transcriptases include MMLV reverse transcriptase, AMV reverse transcriptase, and ThermoScript™ reverse transcriptase (Life Technologies, Grand Island, N.Y.), Thermo-X™ reverse transcriptase (Life Technologies, Grand Island, N.Y.). In some examples, about 0.1 to 50 U (such as about 0.2 to 40 U, about 0.5 to 20 U, about 1 to 10 U, about 2 to 8 U, or about 5 U) of RT is included in the reaction.

The reaction mixture, including sample, LAMP primers, buffers, nucleotides, DNA polymerase, optionally reverse transcriptase, and any other components, is incubated for a period of time and at a temperature sufficient for production of an amplification product. In some examples, the reaction conditions include incubating the reaction mixture at about 37° C. to about 80° C. (such as about 40° C. to about 70° C., about 50° C. to about 65° C., or about 60° C. to about 65° C.), for example about 40° C., about 45° C., about 50° C., about 55° C., about 60° C., about 65° C., about 70° C., about 75° C., or about 80° C. In particular examples, the reaction mixture is incubated at about 60° C., 63.5° C., or 65° C. The reaction mixture is incubated for at least about 5 minutes (such as about 10, about 15, about 20, about 30, about 40, about 50, about 60, about 70, about 80 about 90, about 100, about 110, about 120 minutes or more), for example about 10-120 minutes, about 15-90 minutes, about 20-70 minutes, or about 30-60 minutes.

Following incubation of the reaction mixture, the amplification product is detected by any suitable method. The detection methods may be quantitative, semi-quantitative, or qualitative. In some examples, accumulation of an amplification product is detected by measuring the turbidity of the reaction mixture (for example, visually or with a turbidometer). In other examples, amplification product is detected using gel electrophoresis, for example by detecting presence or amount of amplification product with agarose gel electrophoresis. The particular viral nucleic acid may be determined in some cases by the band pattern observed on gel electrophoresis (for example, HCV-1, HCV-2, and HCV-3 can be discriminated by the pattern of bands on gel electrophoresis). In some examples, amplification product is detected using a colorimetric assay, such as with an intercalating dye (for example, propidium iodide, SYBR green, GelRed, or GelGreen dyes). In other examples, amplification products are detected using a detectable label incorporated in one or more of the LAMP primers (discussed below). The detectable label may be optically detectable, for example, by eye or using a spectrophotometer or fluorimeter. In some examples, the detectable label is a fluorophore, such as those described above. In some examples, the label is detected using a fluorescence scanner (such as ESEQuant Tube Scanner, Qiagen; NanoDrop™ 3300 Fluorospectrometer, Thermo Scientific). One of skill in the art can select one or more detectable labels for use in the methods disclosed herein.

Thus, in some examples, the disclosed methods include detecting fluorescence from a detectable label incorporated in one or more LAMP primers. In some examples, the sample is identified as containing a viral nucleic acid (for example is "positive" for the virus) if an increase in fluorescence is detected compared to a control (such as a no template control sample or a known negative sample). In other examples, the amount of viral nucleic acid in a sample is determined quantitatively. For example, the amount of viral nucleic acid in a test sample can be determined by comparing the amount of fluorescence obtained in a LAMP assay with fluorescence obtained in a LAMP assay with samples containing known amounts of the viral nucleic acid of interest.

In particular embodiments, one of the LAMP primers in a set includes a detectable label, such as a fluorophore. In some examples, a LAMP primer including a detectable label may be referred to herein as a "probe." In a specific example, an LR primer (for example, SEQ ID NOs: 6, 12, 19, 25, 31, 37, 48, 54, 61, or 67) includes a fluorophore, for example attached to the 5' end or the 3' end of the primer. In another example, an LF primer (for example, SEQ ID NOs: 5, 11, 18, 24, 30, 36, 46, 47, 53, 60, or 66) includes a fluorophore, for example attached to the 5' end or the 3' end of the primer. Any fluorophore can be used; in some non-limiting examples, the fluorophore is TET, FAM, Cy3, or TexasRed. In additional examples, the labeled LAMP primer also includes an acceptor fluorophore (a quencher). In some examples, the quencher includes a BLACK HOLE quencher, for example, attached to the 5' end or the 3' end of the primer. Exemplary quenchers include BHQ1, BHQ2, or BHQ3.

A. HBV LAMP Assay

In some embodiments, the methods include contacting a sample (such as a sample including or suspected to include HBV nucleic acids) with at least one set of LAMP primers specific for an HBV nucleic acid under conditions sufficient for amplification of the HBV nucleic acid, producing an amplification product. In some examples, the LAMP primers amplify an HBV large S protein and partially overlapping polymerase region nucleic acid having at least 80% sequence identity (such as at least 85%, 90%, 95%, 98%, or more sequence identity) to SEQ ID NO: 76, or a portion thereof. In some embodiments, the set of LAMP primers amplifies an HBV genotype A nucleic acid, an HBV genotype B nucleic acid, an HBV genotype C nucleic acid, an HBV genotype D nucleic acid, an HBV genotype E nucleic acid, or an HBV genotype F nucleic acid. In some examples, the HBV genotype is determined by visualizing the pattern of bands on gel electrophoresis of the reaction products. The amplification product is detected by any suitable method, such as detection of turbidity, fluorescence (qualitatively or quantitatively), or by gel electrophoresis.

In particular examples, a sample is contacted with a set of LAMP primers for amplification of HBV nucleic acids that includes an F3 primer with at least 90% sequence identity to SEQ ID NO: 1, an R3 primer with at least 90% sequence identity to SEQ ID NO: 2, an FIP primer with at least 90% sequence identity to SEQ ID NO: 3, an RIP primer with at least 90% sequence identity to SEQ ID NO: 4, an LF primer with at least 90% sequence identity to SEQ ID NO: 5 and an LR primer with at least 90% sequence identity to SEQ ID NO: 6, or the reverse complement of any one thereof. In one example, the set of LAMP primers for HBV includes primers comprising, consisting essentially of, or consisting of the nucleic acid sequence each of SEQ ID NOs: 1-6. In some examples, the set of LAMP primers includes an LR primer with at least 90% sequence identity to SEQ ID NO: 6 or the reverse complement thereof, further including a fluorophore (for example at the 5' end of the LR primer) and/or a quencher (for example at the 3' end of the LR primer).

B. HCV LAMP Assay

In other embodiments, the methods include contacting a sample (such as a sample including or suspected to include HCV nucleic acids) with at least one set of LAMP primers specific for an HCV nucleic acid under conditions sufficient for amplification of the HCV nucleic acid, producing an amplification product. In some examples, the LAMP primers amplify a 5' non-coding region (NCR) nucleic acid having at least 80% sequence identity (such as at least 85%, 90%, 95%, 98%, or more sequence identity) to any one of SEQ ID NOs: 77-80, or a portion thereof. In some embodiments, the set of LAMP primers specifically amplifies an HCV genotype 1 nucleic acid (such as an HCV-1a, HCV-1b, and/or HCV-1c nucleic acid), an HCV genotype 2 nucleic acid (such as an HCV-2a, HCV-2b, and/or HCV-2c nucleic acid), an HCV genotype 3 nucleic acid (such as an HCV-3a and/or HCV-3b nucleic acid), or an HCV genotype 4 nucleic acid (such as an HCV-4a nucleic acid). The amplification product is detected by any suitable method, such as detection of turbidity, fluorescence (qualitatively or quantitatively), or by gel electrophoresis. In some examples, the HCV genotype is determined by visualizing the pattern of bands on gel electrophoresis of the reaction products. As described in Example 3, each of HCV-1, HCV-2, and HCV-3 can be discriminated based on the distinct pattern of bands produced by a LAMP assay using the set of primers of SEQ ID NOs: 7-12. In other examples, the HCV genotype is determined by using a set of HCV LAMP primers specific for a single HCV genotype.

In particular examples, a sample is contacted with a set of LAMP primers for amplification of HCV nucleic acids that includes an F3 primer with at least 90% sequence identity to SEQ ID NO: 7, an R3 primer with at least 90% sequence identity to SEQ ID NO: 8, an FIP primer with at least 90% sequence identity to SEQ ID NO: 9, an RIP primer with at least 90% sequence identity to SEQ ID NO: 10, an LF primer with at least 90% sequence identity to SEQ ID NO: 11 and an LR primer with at least 90% sequence identity to SEQ ID NO: 12, or the reverse complement of any one thereof. In one example, the sample is contacted with a set of LAMP primers for HCV including primers comprising, consisting essentially of, or consisting of the nucleic acid sequence each of SEQ ID NOs: 7-12. In some examples, the set of LAMP primers includes an LR primer with at least 90% sequence identity to SEQ ID NO: 12 or the reverse complement thereof, further including a fluorophore (for example at the 5' end of the LR primer) and or a quencher (for example at the 3' end of the LR primer).

In other examples, a sample is contacted with a set of LAMP primers for amplification of HCV nucleic acids that includes an F3 primer with at least 90% sequence identity to SEQ ID NO: 13 or 14, an R3 primer with at least 90% sequence identity to SEQ ID NO: 15, an FIP primer with at least 90% sequence identity to SEQ ID NO: 16, an RIP primer with at least 90% sequence identity to SEQ ID NO: 17, an LF primer with at least 90% sequence identity to SEQ ID NO: 18 and an LR primer with at least 90% sequence identity to SEQ ID NO: 19, or the reverse complement of any one thereof. In one example, the sample is contacted with a set of LAMP primers for HCV including primers comprising, consisting essentially of, or consisting of the nucleic acid sequence each of SEQ ID NOs: 13 and 15-19 or 14-19. In some examples, the set of LAMP primers includes an LR primer with at least 90% sequence identity to SEQ ID NO: 19 or the reverse complement thereof, further including a fluorophore (for example at the 5' end of the LR primer) and/or a quencher (for example at the 3' end of the LR primer).

In further examples, a sample is contacted with a set of LAMP primers for amplification of HCV-1 nucleic acids that includes an F3 primer with at least 90% sequence identity to SEQ ID NO: 20, an R3 primer with at least 90% sequence identity to SEQ ID NO: 21, an FIP primer with at least 90% sequence identity to SEQ ID NO: 22, an RIP primer with at least 90% sequence identity to SEQ ID NO: 23, an LF primer with at least 90% sequence identity to SEQ ID NO: 24, and an LR primer with at least 90% sequence identity to SEQ ID NO: 25, or the reverse complement of any one thereof. In one example, the sample is contacted with a set of LAMP primers specific for HCV-1 including primers comprising, consisting essentially of, or consisting of the nucleic acid sequence each of SEQ ID NOs: 20-25. In some examples, the set of LAMP primers includes an LR primer with at least 90% sequence identity to SEQ ID NO: 25 or the reverse complement thereof, further including a fluorophore (for example at the 5' end of the LR primer) and/or a quencher (for example at the 3' end of the LR primer).

In other examples, a sample is contacted with a set of LAMP primers for amplification of HCV-2 nucleic acids that includes an F3 primer with at least 90% sequence identity to SEQ ID NO: 26, an R3 primer with at least 90% sequence identity to SEQ ID NO: 27, an FIP primer with at least 90% sequence identity to SEQ ID NO: 28, an RIP primer with at least 90% sequence identity to SEQ ID NO: 29, an LF primer with at least 90% sequence identity to SEQ ID NO: 30 and an LR primer with at least 90% sequence identity to SEQ ID NO: 31, or the reverse complement of any one thereof. In one example, the sample is contacted with a set of LAMP primers specific for HCV-2 including primers comprising, consisting essentially of, or consisting of the nucleic acid sequence each of SEQ ID NOs: 26-31. In some examples, the set of LAMP primers includes an LR primer with at least 90% sequence identity to SEQ ID NO: 31 or the reverse complement thereof further including a fluorophore (for example at the 5' end of the LR primer) and/or a quencher (for example at the 3' end of the LR primer).

In further examples, a sample is contacted with a set of LAMP primers for amplification of HCV-3 nucleic acids that includes an F3 primer with at least 90% sequence identity to SEQ ID NO: 32, an R3 primer with at least 90% sequence identity to SEQ ID NO: 33, an FIP primer with at least 90% sequence identity to SEQ ID NO: 34, an RIP primer with at least 90% sequence identity to SEQ ID NO: 35, an LF primer with at least 90% sequence identity to SEQ ID NO: 36, and an LR primer with at least 90% sequence identity to SEQ ID NO: 37, or the reverse complement of any one thereof. In one example, the sample is contacted with a set of LAMP primers specific for HCV-3 including primers comprising, consisting essentially of, or consisting of the nucleic acid sequence each of SEQ ID NOs: 32-37. In some examples, the set of LAMP primers includes an LR primer with at least 90% sequence identity to SEQ ID NO: 37 or the reverse complement thereof, further including a fluorophore (for example at the 5' end of the LR primer) and/or a quencher (for example at the 3' end of the LR primer).

C. HIV LAMP Assay

In some embodiments, the methods include contacting a sample (such as a sample including or suspected to include HIV nucleic acids) with at least one set of LAMP primers specific for an HIV nucleic acid (such as an HIV-1 nucleic acid) under conditions sufficient for amplification of the HIV nucleic acid, producing an amplification product. In some examples, the LAMP primers amplify a p24-specific portion of an HIV gag nucleic acid having at least 80% sequence identity (such as at least 85%, 90%, 95%, 98%, or more sequence identity) to nucleotides 570-760 of GenBank Accession No. J416161 (incorporated by reference as present on Apr. 14, 2014), or a portion thereof. The amplification product is detected by any suitable method, such as detection of turbidity, fluorescence (qualitatively or quantitatively), or by gel electrophoresis.

In particular examples, a sample is contacted with a set of LAMP primers for amplification of HIV nucleic acids that includes an F3 primer with at least 90% sequence identity to SEQ ID NO: 38 or SEQ ID NO: 81, an R3 primer with at least 90% sequence identity to any one of SEQ ID NOs: 39-41, an FIP primer with at least 90% sequence identity to SEQ ID NOs: 42 or 43, an RIP primer with at least 90% sequence identity to SEQ ID NOs: 44 or 45, an LF primer with at least 90% sequence identity to SEQ ID NOs: 46 or 47, and an LR primer with at least 90% sequence identity to SEQ ID NO: 48, or the reverse complement of any one thereof. In one example, the set of LAMP primers for HIV includes primers comprising, consisting essentially of, or consisting of the nucleic acid sequence each of SEQ ID NOs: 38, 41, 42, 45, 47, and 48. In some examples, the set of LAMP primers includes an LR primer with at least 90% sequence identity to SEQ ID NO: 48 or the reverse complement thereof further including a fluorophore (for example at the 5' end of the LR primer) and/or a quencher (for example at the 3' end of the LR primer).

D. HEV LAMP Assay

In some embodiments, the methods include contacting a sample (such as a sample including or suspected to include HEV nucleic acids) with at least one set of LAMP primers specific for an HEV nucleic acid under conditions sufficient for amplification of the HEV nucleic acid, producing an amplification product. In some examples, the LAMP primers amplify an HEV capsid nucleic acid having at least 80% sequence identity (such as at least 85%, 90%, 95%, 98%, or more sequence identity) to nucleotides 5280-5490 of GenBank Accession No. AB437318 (incorporated herein by reference as present on Apr. 14, 2014), or a portion thereof.

The amplification product is detected by any suitable method, such as detection of turbidity, fluorescence (qualitatively or quantitatively), or by gel electrophoresis.

In particular examples, a sample is contacted with a set of LAMP primers for amplification of HEV nucleic acids that includes an F3 primer with at least 90% sequence identity to SEQ ID NO: 49, an R3 primer with at least 90% sequence identity to SEQ ID NO: 50, an FIP primer with at least 90% sequence identity to SEQ ID NO: 51, an RIP primer with at least 90% sequence identity to SEQ ID NO: 52, an LF primer with at least 90% sequence identity to SEQ ID NO: 53, and an LR primer with at least 90% sequence identity to SEQ ID NO: 54, or the reverse complement of any one thereof. In one example, the set of LAMP primers for HEV includes primers comprising, consisting essentially of, or consisting of the nucleic acid sequence each of SEQ ID NOs: 49-54. In some examples, the set of LAMP primers includes an LR primer with at least 90% sequence identity to SEQ ID NO: 54 or the reverse complement thereof further including a fluorophore (for example at the 5' end of the LR primer) and/or a quencher (for example at the 3' end of the LR primer).

E. WNV LAMP Assay

In some embodiments, the methods include contacting a sample (such as a sample including or suspected to include WNV nucleic acids) with at least one set of LAMP primers specific for a WNV nucleic acid under conditions sufficient for amplification of the WNV nucleic acid, producing an amplification product. In some examples, the LAMP primers amplify a WNV nucleic acid. The amplification product is detected by any suitable method, such as detection of turbidity, fluorescence (qualitatively or quantitatively), or by gel electrophoresis.

In particular examples, a sample is contacted with a set of LAMP primers for amplification of WNV nucleic acids that includes an F3 primer with at least 90% sequence identity to SEQ ID NO: 55 or 56, an R3 primer with at least 90% sequence identity to SEQ ID NO: 57, an FIP primer with at least 90% sequence identity to SEQ ID NO: 58, an RIP primer with at least 90% sequence identity to SEQ ID NO: 59, an LF primer with at least 90% sequence identity to SEQ ID NO: 60, and an LR primer with at least 90% sequence identity to SEQ ID NO: 61, or the reverse complement of any one thereof. In one example, the set of LAMP primers for WNV includes primers comprising, consisting essentially of, or consisting of the nucleic acid sequence each of SEQ ID NOs: 55 and 57-61 or 56-61. In some examples, the set of LAMP primers includes an LR primer with at least 90% sequence identity to SEQ ID NO: 61 or the reverse complement thereof, further including a fluorophore (for example at the 5' end of the LR primer) and/or a quencher (for example at the 3' end of the LR primer).

F. DENV LAMP Assay

In some embodiments, the methods include contacting a sample (such as a sample including or suspected to include DENV nucleic acids) with at least one set of LAMP primers specific for an DENV nucleic acid under conditions sufficient for amplification of the DENV nucleic acid, producing an amplification product. In some examples, the LAMP primers amplify a DENV nucleic acid. In some embodiments, the set of LAMP primers amplifies a DENV serotype 1 nucleic acid. In other embodiments, the set of LAMP primers amplifies a DENV serotype 1 nucleic acid, a DENV serotype 2 nucleic acid, a DENV serotype 3 nucleic acid, and/or a DENV serotype 4 nucleic acid. The amplification product is detected by any suitable method, such as detection of turbidity, fluorescence (qualitatively or quantitatively), or by gel electrophoresis. In some examples, the DENV serotype is determined by visualizing the pattern of bands on gel electrophoresis of the reaction products. For example, each of DENV-1, DENV-2, DENV-3, and DENV-4 can be discriminated based on the distinct pattern of bands produced by a LAMP assay In particular examples, a sample is contacted with a set of LAMP primers for amplification of DENV nucleic acids that includes an F3 primer with at least 90% sequence identity to SEQ ID NO: 62, an R3 primer with at least 90% sequence identity to SEQ ID NO: 63, an FIP primer with at least 90% sequence identity to SEQ ID NO: 64, an RIP primer with at least 90% sequence identity to SEQ ID NO: 65, an LF primer with at least 90% sequence identity to SEQ ID NO: 66 and an LR primer with at least 90% sequence identity to SEQ ID NO: 67, or the reverse complement of any one thereof. In one example, the set of LAMP primers for DENV includes primers comprising, consisting essentially of, or consisting of the nucleic acid sequence each of SEQ ID NOs: 62-67. In some examples, the set of LAMP primers includes an LR primer with at least 90% sequence identity to SEQ ID NO: 67 or the reverse complement thereof further including a fluorophore (for example at the 5' end of the LR primer) and or a quencher (for example at the 3' end of the LR primer).

In other examples, a sample is contacted with a set of LAMP primers for amplification of DENV nucleic acids that includes an F3 primer with at least 90% sequence identity to SEQ ID NO: 68, an R3 primer with at least 90% sequence identity to SEQ ID NO: 69, an FIP primer with at least 90% sequence identity to SEQ ID NO: 70, and an RIP primer with at least 90% sequence identity to SEQ ID NO: 71, and optionally, an LF primer with at least 90% sequence identity to SEQ ID NO: 66 and an LR primer with at least 90% sequence identity to SEQ ID NO: 67, or the reverse complement of any one thereof. In one example, the set of LAMP primers for DENV includes primers comprising, consisting essentially of, or consisting of the nucleic acid sequence each of SEQ ID NOs: 68-71 or 66-71. In some examples, the set of LAMP primers includes an LR primer with at least 90% sequence identity to SEQ ID NO: 67 or the reverse complement thereof, further including a fluorophore (for example at the 5' end of the LR primer) and/or a quencher (for example at the 3' end of the LR primer).

In further examples, a sample is contacted with a set of LAMP primers for amplification of DENV nucleic acids that includes an F3 primer with at least 90% sequence identity to SEQ ID NO: 72, an R3 primer with at least 90% sequence identity to SEQ ID NO: 73, an FIP primer with at least 90% sequence identity to SEQ ID NO: 74, and an RIP primer with at least 90% sequence identity to SEQ ID NO: 75, and optionally, an LF primer with at least 90% sequence identity to SEQ ID NO: 66, and an LR primer with at least 90% sequence identity to SEQ ID NO: 67, or the reverse complement of any one thereof. In one example, the set of LAMP primers for DENV includes primers comprising, consisting essentially of, or consisting of the nucleic acid sequence each of SEQ ID NOs: 72-75 or 66, 67, and 72-75. In some examples, the set of LAMP primers includes an LR primer with at least 90% sequence identity to SEQ ID NO: 67 or the reverse complement thereof further including a fluorophore (for example at the 5' end of the LR primer) and/or a quencher (for example at the 3' end of the LR primer).

G. Multiplex Assays

The LAMP and RT-LAMP methods disclosed herein can be used with a single set of LAMP primers (such as a set of LAMP primers for HBV, HCV, HIV, HEV, WNV, or DENV, for example, those described above). In other examples, the methods include multiplex LAMP or RT-LAMP reactions, which include contacting a sample with two or more sets of LAMP primers for amplification of target nucleic acids from different genotypes or serotypes of a virus (such as HCV-1, HCV-2, HCV-3, or HCV-4), or target nucleic acids from different viruses or other pathogens (such as HBV, HCV, HEV, HIV, WNV, and/or DENV).

In a particular example, a multiplex LAMP or RT-LAMP reaction includes contacting a sample with a set of HBV LAMP primers (such as SEQ ID NOs: 1-6) and a set of HCV LAMP primers (such as SEQ ID NOs: 7-12, 13 and 15-19, 14-19, 20-25, 26-31, and/or 32-37) under conditions sufficient for amplification of an HBV and/or HCV nucleic acid. In another example, a multiplex LAMP or RT-LAMP reaction includes contacting a sample with a set of HBV LAMP primers (such as SEQ ID NOs: 1-6), a set of HCV LAMP primers (such as SEQ ID NOs: 7-12, 13 and 15-19, 14-19, 20-25, 26-31, and/or 32-37), and a set of HIV LAMP primers (such as a set of LAMP primers selected from SEQ ID NOs: 38-48 and 81; for example, SEQ ID NOs: 38, 41, 42, 45, 47, and 48) under conditions sufficient for amplification of an HBV, HCV, and/or HIV nucleic acid. In yet another example, a multiplex LAMP or RT-LAMP reaction includes contacting a sample with a set of HBV LAMP primers (such as SEQ ID NOs: 1-6), a set of HCV LAMP primers (such as SEQ ID NOs: 7-12, 13 and 15-19, 14-19, 20-25, 26-31, and/or 32-37), a set of HIV LAMP primers (such as a set of LAMP primers selected from SEQ ID NOs: 38-48 and 81; for example, SEQ ID NOs: 38, 41, 42, 45, 47, and 48), and a set of HEV LAMP primers (such as SEQ ID NOs: 49-54) under conditions sufficient for amplification of an HBV, HCV, HIV, and/or HEV nucleic acid. In a still further example, a multiplex LAMP or RT-LAMP reaction includes contacting a sample with a set of HBV LAMP primers (such as SEQ ID NOs: 1-6), a set of HCV LAMP primers (such as SEQ ID NOs: 7-12, 13 and 15-19, 14-19, 20-25, 26-31, and/or 32-37), a set of HIV LAMP primers (such as a set of LAMP primers selected from SEQ ID NOs: 38-48 and 81; for example, SEQ ID NOs: 38, 41, 42, 45, 47, and 48), a set of HEV LAMP primers (such as SEQ ID NOs: 49-54), and a set of WNV LAMP primers (such as SEQ ID NOs: 55 and 57-61 or 56-61) under conditions sufficient for amplification of an HBV, HCV, HIV, HEV and/or WNV nucleic acid. In another example, a multiplex LAMP or RT-LAMP reaction includes contacting a sample with a set of HBV LAMP primers (such as SEQ ID NOs: 1-6), a set of HCV-2 LAMP primers (such as SEQ ID NOs: 7-12, 13 and 15-19, 14-19, 20-25, 26-31, and/or 32-37), a set of HIV LAMP primers (such as a set of LAMP primers selected from SEQ ID NOs: 38-48 and 81; for example, SEQ ID NOs: 38, 41, 42, 45, 47, and 48), a set of HEV LAMP primers (such as SEQ ID NOs: 49-54), a set of WNV LAMP primers (such as SEQ ID NOs: 55 and 57-61 or 56-61), and a set of DENV primers (such as a set of DENV LAMP primers selected from SEQ ID NOs: 62-75, for example SEQ ID NOs: 61-67, 69-71, or 72-75) under conditions sufficient for amplification of HBV, HCV, HIV, HEV, WNV, and/or DENV nucleic acids.

In some embodiments, the multiplex methods include contacting the sample with at least one LR primer that includes a fluorophore and optionally a quencher (referred to herein in some examples as a "fluoro-oligo"). In some examples, the multiplex set of primers includes a single fluoro-oligo, specific for one of the viral nucleic acids that can be detected by the assay. In other examples, the multiplex set of primers includes two or more fluoro-oligos, each with the same or different fluorophores and/or quenchers. In some examples, each set of LAMP primers included in the set contacted with the sample includes a fluoro-oligo, each with a different fluorophore. This enables one-tube detection of one or more viral nucleic acids present in the sample by detecting presence of fluorescence from each fluoro-oligo. An increase in fluorescence over background, non-template control, or a known negative sample reaction indicates the presence of the particular viral nucleic acid in the sample.

IV. Assay Buffer

Disclosed herein is a novel assay buffer that can be used for nucleic acid detection and/or amplification assays, including LAMP assays, PCR, and reverse transcription. The buffer can also act as a cell lysis buffer, and thus can be used directly with samples such as blood, serum, or plasma, without prior nucleic acid extraction.

In some embodiments, the buffer (referred to herein as mannitol acetate buffer, or MAB) has a pH of about 7.8 (such as about 7.7-7.9) and includes 2% D-mannitol, 0.2% Triton®-X100, 40 mM Tris-HCl, 20 mM KCl, 20 mM $(NH_4)_2SO_4$, 6 mM $MgSO_4$, 0.5 M L-proline, 10 mM Tris acetate, 1.6 mM magnesium acetate, and 15 mM potassium acetate. In some examples, the MAB also includes one or more dNTPs, such as dATP, dCTP, dGTP, and/or dTTP. In some examples, the MAB includes 2 mM each of dATP, dCTP, dGTP, and dTTP. In other examples, the MAB is as listed above, however, D-mannitol is included at 1-3, L-proline is included at 0.2-0.5 M, and/or Triton®-X100 is included at 0.1-0.3.

The MAB is highly stable at a range of temperatures and for long periods of time. For example, LAMP reactions can still be successfully performed following storage of the MAB at room temperature for extended periods of time and/or following exposure of the MAB to heating. In some examples, the MAB is stable when stored at room temperature (about 20-27° C., such as about 22-25° C.) for 1 day to at least 6 months. In particular examples, the MAB is stable at room temperature for at least 6 months, at least 12 months, at least 18 months, at least 24 months, or more. In other examples, the MAB is stable when heated to at least 60° C. for 30-60 minutes and cooled to room temperature one or more times.

In some examples, the MAB buffer is used in nucleic acid synthesis or amplification reactions, such as PCR, RT-PCR, LAMP, RT-LAMP, or reverse transcription. For example, MAB can be used in place of other commercially available reaction buffers in nucleic acid synthesis or amplification reactions. In other examples, the MAB buffer is used for cell lysis. Thus, MAB can be used in single tube reactions that include a sample containing cells (such as a blood, plasma, or serum sample), primers (such as one or more sets of LAMP primers disclosed herein), enzymes (such as DNA polymerase and in some cases reverse transcriptase), and other reagents.

The MAB buffer provides several advantages over conventional reaction and/or lysis buffers. As discussed above, MAB is extremely stable over a range of storage times and temperature exposures. In addition, without being bound by theory, it is believed that the buffer has a destabilizing effect on double-stranded nucleic acids, lowers the $T_m$ of DNA, and/or stabilizes DNA polymerase. As a result, decreased reaction times and/or temperatures can be used for reactions including MAB as compared to conventional buffers. For example, use of MAB can decrease the necessary reaction times for reverse transcription, PCR, RT-PCR, LAMP, or RT-LAMP reactions by at least 10% (such as at least 25%, 50%, 75%, or more) compared with reactions using conventional (e.g., commercially available reaction buffers).

V. Primers, Probes, and Kits

Primers and probes (such as isolated nucleic acid primers and/or probes) suitable for use in the disclosed methods are described herein. The disclosed primers and probes are suitable for detecting viral nucleic acids (such as HBV, HCV, HIV, HEV, DENV, or WNV nucleic acids) using LAMP or RT-LAMP.

In some embodiments, the disclosed primers and/or probes are between 10 and 60 nucleotides in length, such as 10, 11, 12, 13, 14, 15, 16, 17, 18, 19, 20, 21, 22, 23, 24, 25, 26, 27, 28 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length and are capable of hybridizing to, and in some examples, amplifying the disclosed nucleic acid molecules. In some examples, the primers and/or probes are at least 10, 15, 20, 25, 30, 35, 40, 45, 50, 55, or 60 nucleotides in length. In other examples, the primers and/or probes may be no more than 10, 15, 20, 25, 30, 35, 40, 45, 50, 55, or 60 nucleotides in length.

In some embodiments, the disclosed primers include LAMP primers for amplification of HBV nucleic acids, including primers with at least 90% sequence identity to any one of SEQ ID NOs: 1-6. In some examples, the disclosed HBV primers are "universal" primers, for example, are capable of amplifying nucleic acids from multiple HBV genotypes (for example, one or more of HBV-A, HBV-B, HBV-C, HBV-D, HBV-E, and/or HBV-F). In some examples, the primers have at least 95% sequence identity to any one of SEQ ID NOs: 1-6, comprise the sequence of any one of SEQ ID NOs: 1-6, or consist of the sequence of any one of SEQ ID NOs: 1-6.

In other embodiments, the primers include LAMP primers for amplification of HCV nucleic acids, including primers with at least 90% sequence identity to any one of SEQ ID NOs: 7-12 or 13-19 (e.g., HCV universal primers). In further examples, the primers include LAMP primers for amplification of specific HCV genotypes, such as primers with at least 90% sequence identity to SEQ ID NOs: 20-25 (HCV-1, such as genotypes 1a, 1b, and/or 1c), SEQ ID NOs: 26-31 (HCV-2, such as genotypes 2a, 2b, and/or 2c), or SEQ ID NOs: 32-37 (HCV-3, such as genotypes 3a and/or 3b). In some examples, the primers have at least 95% sequence identity to any one of SEQ ID NOs: 7-37, comprise the sequence of any one of SEQ ID NOs: 7-37, or consist of the sequence of any one of SEQ ID NOs: 7-37.

In additional embodiments, the disclosed primers include LAMP primers for amplification of HIV nucleic acids, including primers with at least 90% sequence identity to any one of SEQ ID NOs: 38-48 and 81. In some examples, the disclosed HIV primers are capable of amplifying nucleic acids from HIV-1. In some examples, the primers have at least 95% sequence identity to any one of SEQ ID NOs: 38-48 and 81, comprise the sequence of any one of SEQ ID NOs: 38-48 and 81, or consist of the sequence of any one of SEQ ID NOs: 38-48 and 81.

In further embodiments, the disclosed primers include LAMP primers for amplification of HEV nucleic acids, including primers with at least 90% sequence identity to any one of SEQ ID NOs: 49-54. In some examples, the primers have at least 95% sequence identity to any one of SEQ ID NOs: 49-54, comprise the sequence of any one of SEQ ID NOs: 49-54, or consist of the sequence of any one of SEQ ID NOs: 49-54.

In other embodiments, the disclosed primers include LAMP primers for amplification of WNV nucleic acids, including primers with at least 90% sequence identity to any one of SEQ ID NOs: 55-61. In some examples, the primers have at least 95% sequence identity to any one of SEQ ID NOs: 55-61, comprise the sequence of any one of SEQ ID NOs: 55-61, or consist of the sequence of any one of SEQ ID NOs: 55-61.

In still further embodiments, the disclosed primers include LAMP primers for amplification of DENV nucleic acids, including primers with at least 90% sequence identity to any one of SEQ ID NOs: 62-75. In some examples, the primers are capable of amplifying nucleic acids from one or more DENV serotypes (for example, one or more of DEN-1, DEN-2, DEN-3, and/or DEN-4), such as SEQ ID NOs: 62-75. In some examples, the primers have at least 95% sequence identity to any one of SEQ ID NOs: 62-75, comprise the sequence of any one of SEQ ID NOs: 62-75, or consist of the sequence of any one of SEQ ID NOs: 62-75. In particular examples, the primers amplify a DENV-1 nucleic acid.

In some examples, at least one of the disclosed primers includes a detectable label, such as a fluorophore. In particular examples, the LR primer (e.g., any one of SEQ ID NOs: 6, 12, 19, 25, 31, 37, 48, 54, 61, or 67) includes a fluorophore at the 5' or 3' end. In other examples, the LF primer (e.g., any one of SEQ ID NOs: 5, 11, 18, 24, 30, 36, 46, 47, 53, 60, or 66 includes a fluorophore at the 5' or 3' end. In non-limiting examples, the fluorophore can be TET, FAM, or TexasRed. In other examples, the LR or LF primer includes a fluorescence quencher at the 5' or 3' end, such as a dark quencher, which is a Black Hole Quencher (such as BHQ1) in one non-limiting example.

Also provided by the present disclosure are probes and primers that include variations to the nucleotide sequences shown in any of SEQ ID NOs: 1-75 and 81, as long as such variations permit detection and/or amplification of the target nucleic acid molecule. For example, a probe or primer can have at least 90% sequence identity such as at least 91%, 92%, 93%, 94%, 95%, 96%, 97%, 98%, or 99% identity to a nucleic acid including the sequence shown in any of SEQ ID NOs: 1-75 and 81. In such examples, the number of nucleotides does not change, but the nucleic acid sequence shown in any of SEQ ID NOs: 1-75 and 81 can vary at a few nucleotides, such as changes at 1, 2, 3, 4, or 5 nucleotides.

The present application also provides probes and primers that are slightly longer or shorter than the nucleotide sequences shown in any of SEQ ID NOs: 1-75 and 81, as long as such deletions or additions permit amplification and/or detection of the desired target nucleic acid molecule. For example, a probe or primer can include a few nucleotide deletions or additions at the 5'- or 3'-end of the probe or primers shown in any of SEQ ID NOs: 1-75 and 81, such as addition or deletion of 1, 2, 3, or 4 nucleotides from the 5'- or 3'-end, or combinations thereof (such as a deletion from one end and an addition to the other end). In such examples, the number of nucleotides changes.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In some examples, the probes and primers disclosed herein include one or more synthetic bases or alternative bases (such as inosine). In other examples, the probes and primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the probes and primers disclosed herein include a minor groove binder conjugated to the 5' or 3' end of the oligonucleotide (see, e.g., U.S. Pat. No. 6,486,308).

The nucleic acid primers and probes disclosed herein can be supplied in the form of a kit for use in the detection or amplification of one or more viral nucleic acids (such as one or more of HBV, HCV, HEV, HIV, WNV, and/or DENV). In such a kit, an appropriate amount of one or more of the nucleic acid probes and/or primers (such as one or more of SEQ ID NOs: 1-75 and 81) are provided in one or more containers or in one or more individual wells of a multiwell plate or card (such as a microfluidic card). A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid probes (for example, 1, 2, 3, 4, 5, or more probes, such as LR primers with an incorporated fluorophore and/or quencher) and/or primers (for example, 1, 2, 3, 4, 5, 6, 7, 8, 9, 10, 11, 12, 13, 14, 15, or more primers) for use in amplification and/or detection of viral nucleic acids. One or more control probes, primers, and or nucleic acids also may be supplied in the kit. An exemplary control is RNase P; however one of skill in the art can select other suitable controls.

In some examples, one or more probes and/or one or more primers (such as one or more sets of primers suitable for LAMP), may be provided in pre-measured single use amounts in individual, typically disposable, tubes, wells, or equivalent containers. In this example, the sample to be tested for the presence of the target nucleic acids can be added to the individual tube(s) or well(s) and amplification and/or detection can be carried out directly. In some examples, the containers may also contain additional reagents for amplification reactions, such as buffer (for example, the MAB buffer disclosed herein), enzymes (such as reverse transcriptase and/or DNA polymerase), dNTPs, or other reagents. In some embodiments, the container includes all of the components required for the reaction except the sample (and water, if the reagents are supplied in dried or lyophilized form). In some examples, the kits include at least one detectably labeled primer, such as a detectably labeled LR primer (e.g., SEQ ID NOs: 6, 19, 25, 31, 37, 48, 54, 61, or 67).

In particular examples, the kits include at least one set of LAMP primers for amplification and/or detection of HBV nucleic acids, for example in a single tube, well, or other container. In one example, the kit includes a set of primers including SEQ ID NOs: 1-6.

In other examples, the kits include at least one set of LAMP primers for amplification and/or detection of HCV nucleic acids (such as 1, 2, 3, 4, or 5 sets of LAMP primers). In some examples, each set of LAMP primers is in a single tube, well, or other container. In some examples, the kit includes at least one set of LAMP primers including SEQ ID NOs: 7-12, a set of LAMP primers including SEQ ID NOs: 13 and 15-19 or SEQ ID NOs: 14-19, a set of LAMP primers including SEQ ID NOs: 20-25, a set of LAMP primers including SEQ ID NOs: 26-31, and/or a set of LAMP primers including SEQ ID NOs: 32-37.

In still further examples, the kits include at least one set of LAMP primers for amplification and/or detection of HIV, for example in a single tube, well, or other container. In some examples, the kit includes a set of LAMP primers selected from SEQ ID NOs: 38-48 and 81. In one example, the kit includes a set of LAMP primers comprising or consisting of SEQ ID NOs: 38, 41, 42, 45, 47, and 48.

In additional examples, the kits include at least one set of LAMP primers for amplification and/or detection of HEV, for example in a single tube, well, or other container. In one example, the kit includes a set of LAMP primers including SEQ ID NOs: 49-54.

In further examples, the kits include at least one set of LAMP primers for amplification and/or detection of WNV, for example in a single tube, well, or other container. In some examples, the kit includes a set of LAMP primers including SEQ ID NOs: 55 and 57-61 or SEQ ID NOs: 56-61.

In still further examples, the kits include at least one set of LAMP primers for amplification and/or detection of DENV, for example in a single tube, well, or other container. In some examples, the kit includes a set of LAMP primers including SEQ ID NOs: 62-67, SEQ ID NOs: 68-71, SEQ ID NOs: 66-71, SEQ ID NOs: 72-75, or SEQ ID NOs: 66, 67, and 72-75.

In some embodiments, disclosed herein are kits for multiplex detection of two or more viral nucleic acids in a sample. Thus, in some examples, the kits include two or more sets of LAMP primers (such as 2, 3, 4, 5, 6, 7, 8, 9, 10, or more sets of LAMP primers) for detection of viral nucleic acids, in a single container (such as a single tube, well, or other container). In some examples, the kit includes in a single container two or more sets of LAMP primers (optionally with detectably labeled LR primers in each set) selected from a set of LAMP primers including SEQ ID NOs: 1-6 (HBV), a set of LAMP primers including SEQ ID NOs: 7-12 (HCV universal), a set of LAMP primers selected from SEQ ID NOs: 13-19 (HCV universal), a set of LAMP primers including SEQ ID NOs: 20-25 (HCV-1), a set of LAMP primers including SEQ ID NOs: 26-31 (HCV-2), a set of LAMP primers including SEQ ID NOs: 32-37, a set of LAMP primers selected from SEQ ID NOs: 38-48 and 81 (HIV; for example, SEQ ID NOs: 38, 41, 42, 45, 47, and 48), a set of LAMP primers including SEQ ID NOs: 49-54 (HEV), a set of LAMP primers selected from SEQ ID NOs: 55-61 (WNV), and a set of LAMP primers selected from SEQ ID NOs: 62-75 (DENV; for example, SEQ ID NOs: 62-67). The sets of LAMP primers optionally include a detectably labeled primer, such as detectably labeled LR primer. In some embodiments, the kit includes two or more detectably labeled LR primers with different labels (for example, each with a fluorophore with a different emission wavelength).

In one example, a kit includes in a single container (either in liquid or dried form) a set of LAMP primers including SEQ ID NOs: 1-6 (HBV) and a set of LAMP primers including SEQ ID NOs: 7-12 or selected from SEQ ID NOs: 13-19 (HCV). In an additional example, a kit includes in a single container (either in liquid or dried form) a set of LAMP primers including SEQ ID NOs: 1-6 (HBV), a set of LAMP primers including SEQ ID NOs: 7-12 or selected from SEQ ID NOs: 13-19 (HCV), and a set of LAMP primers selected from SEQ ID NOs: 38-48 and 81 (HIV; for example, SEQ ID NOs: 38, 41, 42, 45, 47, and 48). In another example, a kit includes in a single container (either in liquid or dried form) a set of LAMP primers including SEQ ID NOs: 1-6 (HBV), a set of LAMP primers including SEQ ID NOs: 7-12 or selected from SEQ ID NOs: 13-19 (HCV), and a set of LAMP primers selected from SEQ ID NOs: 55-61 (WNV). In a further example, a kit includes in a single container (either in liquid or dried form) a set of LAMP primers including SEQ ID NOs: 1-6 (HBV), a set of LAMP primers including SEQ ID NOs: 7-12 or selected from SEQ ID NOs: 13-19 (HCV), a set of LAMP primers including SEQ ID NOs: 49-54 (HEV), and a set of LAMP primers selected from SEQ ID NOs: 38-48 and 81 (HIV; for example, SEQ ID NOs: 38, 41, 42, 45, 47, and 48). In yet another example, a kit includes in a single container (either in liquid or dried form) a set of LAMP primers including SEQ ID NOs: 1-6 (HBV), a set of LAMP primers including SEQ ID NOs: 7-12 or selected from SEQ ID NOs: 13-19 (HCV), a set of LAMP primers selected from SEQ ID NOs: 38-48 and 81 (HIV; for example, SEQ ID NOs: 38, 41, 42, 45, 47, and 48), a set of LAMP primers including SEQ ID NOs: 49-54 (HEV), a set of LAMP primers selected from SEQ ID NOs: 55-61 (WNV), and a set of LAMP primers selected from SEQ ID NOs: 62-75 (DENV; for example, SEQ ID NOs: 62-67). In a further example, a kit includes in a single container (either in liquid or dried form) a set of LAMP primers including SEQ ID NOs: 7-12 or selected from SEQ ID NOs: 13-19 (HCV "universal"), a set of LAMP primers including SEQ ID NOs: 20-25 (HCV-1), a set of LAMP primers including SEQ ID NOs: 26-31 (HCV-2), and a set of LAMP primers including SEQ ID NOs: 32-37 (HCV-3).

The kits disclosed herein may also include one or more control probes and/or primers. In some examples, the kit includes at least one probe that is capable of hybridizing to an RNase P nucleic acid and/or one or more primers capable of amplifying an RNase P nucleic acid. One of skill in the art can identify and select primers for a suitable control nucleic acid. In additional examples, the kit may include one or more positive control samples (such as a sample including a particular viral nucleic acid) and/or one or more negative control samples (such as a sample known to be negative for a particular viral nucleic acid).

The present disclosure is illustrated by the following non-limiting Examples.

Example 1

Assay Reagents

Sets of primers were designed for LAMP assays for HBV, HCV, HEV, HIV-1, WNV, and DENY (Table 1). For each set, the LR primer included a fluorophore at the 5′ end and a quencher at the 3′ end.

TABLE 1

LAMP primer sequences

| Virus | Primer Name | Primer Sequence (5′-3′) | SEQ ID NO: |
|---|---|---|---|
| HBV Universal | HBU-F3 | TCCTCACAATACCGCAGAGT | 1 |
| | HBU-R3 | GCAGCAGGATGAAGAGGAAT | 2 |
| | HBU-FIP | GTTGGGGACTGCGAATTTTGGCT TTTTAGACTCGTGGTGGACTTCT | 3 |
| | HBU-RIP | TCACTCACCAACCTCCTGTCCTT TTTAAAACGCCGCAGACACAT | 4 |
| | HBU-LF | GGTGATCCCCCTAGAAAATTGAG | 5 |
| | HBU-LR | AATTTGTCCTGGTTATCGCTGG | 6 |

TABLE 1-continued

LAMP primer sequences

| Virus | Primer Name | Primer Sequence (5′-3′) | SEQ ID NO: |
|---|---|---|---|
| HCV Universal (set 1) | HCVU-F3 | GAGTGTTGTACAGCCTCCAGGA | 7 |
| | HCVU-R3 | ATTGGGCGGCGGTTGGTG | 8 |
| | HCVU-FIP | CTCGGCTAGCAGTCTTGCGGTTT TGATGACCGGGTCCTTTCTTG | 9 |
| | HCVU-RIP | TAGTGTTGGGTCGCGAAAGGCTT TTCACGGTCTACGAGACCTCC | 10 |
| | HCVU-LF | GGGCATTGAGCGGGTTAATC | 11 |
| | HCVU-LR | TTGCGGTACTGCCTGATAGG | 12 |
| HCV Universal (set 2) | HCU-F3 | CGGGAGAGCCATAGTGGT | 13 |
| | HCU-F3a | GGCGACACTCCACCATAGAT | 14 |
| | HCU-R3 | CACGGTCTACGAGACCTCC | 15 |
| | HCU-FIP | GGCATTGAGCGGGTTGATCCAAT TTTTGCGGAACCGGTGAGTAC | 16 |
| | HCU-RIP | CGCGAGACTGCTAGCCGAGTTTT TACCCTATCAGGCAGTACCAC | 17 |
| | HCU-LF | TCGTCCTGCCAATTCCGG | 18 |
| | HCU-LR | GTGTTGGGTCGCGAAAGG | 19 |
| HCV1 | HCV1-F3 | GGCGACACTCCACCATGAAT | 20 |
| | HCV1-R3 | CTATCAGGCAGTACCACAAGGC | 21 |
| | HCV1-FIP | CACTATGGCTCTCCCGGGAGTTT TCGTCTAGCCATGGCGTTAG | 22 |
| | HCV1-RIP | GGAACCGGTGAGTACACCGGTTT TCCCAAATCTCCAGGCATTGA | 23 |
| | HCV1-LF | AGGCTGCACGACACTCATA | 24 |
| | HCV1-LR | GACCGGGTCCTTTCTTGGA | 25 |
| HCV2 | HCV2-F3 | CGCAGAAAGCGTCTAGCCA | 26 |
| | HCV2-R3 | CGTACTCGCAAGCACCCTATC | 27 |
| | HCV2-FIP | ATGACCGGGCATAGAGTGGGTTT TTGTGGTCTGCGGAACCGGTGA | 28 |
| | HCV2-RIP | GCCCCCGCAAGACTGCTAGCTTT TCTCGCAAGCACCCTATCAGGC | 29 |
| | HCV2-LF | AAAGGACCCAGTCTTCCCGG | 30 |
| | HCV2-LR | AGCGTTGGGTTGCGAAAGGCC | 31 |
| HCV3 | HCV3-F3 | CCCAGAAATTTGGGCGTGCC | 32 |
| | HCV3-R3 | GGAACTTGACGTCCTGTGG | 33 |
| | HCV3-FIP | GCAAGCACCCTATCAGGCAGTAT TTTCGCGAGATCACTAGCCGA | 34 |
| | HCV3-RIP | GGAGGTCTCGTAGACCGTGCATT TTGCGACGGATGGTGTTTCT | 35 |
| | HCV3-LF | CTTTCGCGACCCAACACTA | 36 |
| | HCV3-LR | CATGAGCACACTTCCTAAACCTCAA | 37 |
| HIV-1 | HIV1-F3 | ACACAGTGGGGGGACATCAAGC | 38 |
| | HIV1-F3A | AACACCATGCTAAACACAGTGG | 81 |
| | HIV1-R3 | GTCATCCATGCTATTTGTTCCTG | 39 |
| | HIV1-R3A | TCCATGCTATTTGTTCCTGAAGGG | 40 |
| | HIV1-R3B | CCTGAAGGGTACTAGTAGTTCCTG | 41 |
| | HIV1-FIP | GATGCAATCTATCCCATTCTGTTT TGCCATGCAAATGTTAAAAG | 42 |
| | HIV1-FIPA | GATGCAATCTATCCCATTCTGTTT TGCCATGCAAATGTTAAAAGAGACC | 43 |
| | HIV1-RIP | AGTGCATGCAGGGCCTATTGCACT TTTGTTCCTGCTATGTCACTTCC | 44 |
| | HIV1-RIP2 | AGTCCATGGAGGGCCTATTGCACT TTTGTTCCTGCTATGTCACTTCC | 45 |
| | HIV1-LF | TCAGTTCCTCATTGATGGTC | 46 |
| | HIV1-LF2 | CAGCTTCCTCATTGATGGTCT | 47 |
| | HIV1-LR | CAGGCCAGATGAGAGAACCAA | 48 |
| HEV | HEV-F3a | CGGTGGTTTCTGGGGTGACA | 49 |
| | HEV-R3 | GAGATAGCAGTCAACGGCGC | 50 |
| | HEV-FIP | AGGGCGAGCTCCAGCCCCGGTTTT GCCCTTCGCCCTCCCTATATT | 51 |
| | HEV-RIP | CCAGTCCCAGCGCCCTCCGTTTT AGCTGGGGCAGA TCGACGAC | 52 |
| | HEV-LF | TGTGAAACGACATCGGCGGC | 53 |
| | HEV-LR | CGTCGATCTGCCCCAGCTGG | 54 |
| WNV | WF3 | GGGGCCAATACGATTTGTGT | 55 |
| | WF3a | CGATTTGTGTTGGCTCTCTTGGCGT | 56 |

TABLE 1-continued

LAMP primer sequences

| Virus | Primer Name | Primer Sequence (5'-3') | SEQ ID NO: |
|---|---|---|---|
| | WR3 | AGGCCAATCATGACTGCAAT | 57 |
| | WFIP | CTCTCCATCGATCCAGCACTGCTTT TCTTGGCGTTCTTCAGGTTCA | 58 |
| | WRIP | ACTAGGGACCTTGACCAGTGCTTTT TTCCGGTCTTTCCTCCTCTT | 59 |
| | WLF | CGGGTCGGAGCAATTGCTG | 60 |
| | WLR | TCAATCGGCGGAGCTCAAAAC | 61 |
| DENV | DVF3 | AGCTTCATCGTGGGGATGT | 62 |
| | DVR3 | CTCTCCCAGCGTCAATATGC | 63 |
| | DVFIP | GGAGGGGTCTCCTCTAACCACTTTT TGGCTGCAACCCATGGAAG | 64 |
| | DVRIP | CAAAACATAACGCAGCAGCGGGTTT TGGGGGTCTCCTCTAACCTC | 65 |
| | DVLF | TGCTACCCCATGCGTACAG | 66 |
| | DVLR | CAACACCAGGGGAAGCTGT | 67 |
| DENV (set 2) | DF3 | ATGGAAGCTGTACGCATGG | 68 |
| | DR3 | GCGTTCTGTGCCTGGAATG | 69 |
| | DFIP | AGGATACAGCTTCCCCTGGTGTTTT TGTGGTTAGAGGAGACCCCT | 70 |
| | DRIP | AGAGGTTAGAGGAGACCCCCGTTTT AGCAGGATCTCTGGTCTCTC | 71 |
| DENV-1 | D1F3 | GGCTGCAACCCATGGAAG | 72 |
| | D1R3 | TGCCTGGAATGATGCTGTAG | 73 |
| | D1FIP | CGCTGCTGCGTTATGTTTTGGGTTT TCTGTACGCATGGGGTAGC | 74 |
| | D1RIP | AGAGGTTAGAGGAGACCCCCGTTTT AGCAGGATCTCTGGTCTCTC | 75 |

A new thermostable reaction buffer, the mannitol acetate buffer (MAB; pH 7.8) was formulated and used for LAMP reactions. MAB consisted of 2% D-mannitol; 0.2% Triton®-X100; 0.5 M L-proline; 10 mM Tris acetate; 1.6 mM magnesium-acetate; 15 mM potassium acetate; 40 mM Tris-HCl; 20 mM KCl; 20 mM $(NH_4)_2SO_4$; 6 mM $MgSO_4$; and 2 mM each dNTPs.

Example 2

LAMP Assay for Detection of Hepatitis B Virus

The subject matter of this example is included in Nyan et al. (Clin. Infect. Dis. doi: 10.1093/cid/ciu210, 2014), which is incorporated herein by reference in its entirety.

Introduction

Hepatitis B virus (HBV) is a blood-borne pathogen which infects over 4 million people yearly. About 350 million people world-wide are chronically infected and are infectious carriers of the virus. Mainly transmitted through blood-borne methods, HBV-infection can lead to hepatitis, liver cirrhosis, and hepatocellular carcinoma, and often co-infects with HCV and HIV (Liang, Hepatology 49:S13-S21, 2009; Arababadi et al, Clin. Res. Hepatol. Gastroenterol. 35:554-559, 2011; Kim et al., BMC Infect. Dis. 12:160, 2012).

HBV is a circular, partially double-stranded DNA virus of 3.2 kilobases. There are 8 known genotypes (A to H) that are divergent by >8% across the entire genome and are distributed world-wide (Okamoto et al., J. Gen Virol. 69:2575-2583, 1988; Wai et al., Clin. Liver Dis. 8:321-352, 2004; Wong et al., Curr. Opin. Infect. Dis. 25:570-577, 2012). Describing epidemiology of HBV does add to the literature, but treatment remains far-fetched in the developing world due to the high cost of anti-virals. However, a tool capable of generally detecting the major HBV genotypes may help in understanding the global geographic prevalence of HBV, aid in addressing the burden that HBV infection places on health care systems, and guide public health and clinicians in designing preventive and therapeutic measures.

Infection with HBV is a global public health problem, particularly in poorer countries where health care resources are limited and inaccessible. According to the WHO, countries in regions of Asia, Africa, and South/Central America have high HBV carrier rates of over 8% (Franco et al., World J. Hepatol. 4:74-80, 2012; Ott et al., Vaccine 30:2212-2219, 2012). This problem is compounded by the lack of advanced medical and diagnostic laboratory services for donor screening or routine testing of patients.

In many developed countries, blood-donors are screened for HBV surface antigen, antibodies to the core of HBV, and HBV-DNA in order to ensure safe blood-supply and clinical diagnosis. Such tests are conventionally performed with tests including, ELISA and real-time PCR. These tests are time-consuming, expensive, and require skilled personnel and elaborate equipment to perform (Caliendo et al., J. Clin. Microbiol. 49:2854-2858, 2011; Kao, Expert Rev. Gastroenterol. Hepatol 2:553-562, 2008; Wang et al., J. Biomed. Nanotechnol. 8:786-790, 2012). Hence, there is a need for a rapid and cost-effective detection tool for screening blood-donors and testing patient specimens for HBV infection in endemic as well as resource-limited environments.

This study reports the development of a simple, sensitive, and specific loop-mediated isothermal amplification assay (HBV-LAMP) for rapid and universal detection of all the major HBV genotypes in peripheral blood. LAMP is a DNA amplification method that uses 2 to 3 pairs of sequence-specific primers and a DNA strand-displacement process for amplification under isothermal condition. The amplification results in multiple inverted repeats of amplicons that form a ladder-like banding pattern. This unique and portable detection tool has the potential for use in point-of-care settings for blood-screening and patient follow-up.

Methods

Specimens, standards, and DNA preparation: HBV genotyping reference plasma-panels containing various titers of WHO-International standards (OptiQuant, AcroMetrix/Life Technologies, Grand Island, N.Y.) and the Worldwide HBV-DNA Performance-Panel (WWHD301, SeraCare Life Sciences, Milford, Mass.) were used. A total of 182 donor-plasma specimens were also used for assay development and evaluation. DNA extraction was performed using the QIAamp® DNA Blood-Mini-Kit (Qiagen, Germantown, Md.) according to manufacturer's protocol. DNA was extracted from 200-400 µL of plasma-standards and eluted in 50-150 µL of Qiagen Buffer AE. Nucleic acid from the clinical specimens was concentrated by addition of 0.5 M Ammonium-Acetate and 0.05 mg/mL Glycerol (Ambion/Life Technologies, Grand Island, N.Y.), precipitated with one volume of 100% Isopropanol (Sigma-Aldrich, St. Louis, Mo.), centrifuged, and the DNA pellet re-suspended in 25-35 µL of Buffer AE. Finally, the DNA was measured using NanoDrop-1000 (Thermo-Scientific, DE, USA), aliquoted, and stored at −80° C. until needed for testing.

Heat-treatment of donor plasma specimens as substrate: Substrate for HBV-LAMP was also prepared by heat-treatment of donor plasma without DNA extraction. Briefly, 25 µL of specimens were diluted 2-fold with nuclease-free water. The mixture was briefly vortexed and heated at 95° C. for 5 minutes, then at 100° C. for approximately 5 minutes. The mixture was then centrifuged at 12,000×g for 3 minutes. The supernatant was reserved and 3-10 µL used in isothermal amplification for detection of HBV.

Design of oligonucleotides: Sequences of HBV genotypes (n=197) were retrieved from the GenBank database of the NCBI and from the European Nucleotide Archive of the European Molecular Biology Laboratory (EMBL). The sequences were analyzed using ClustalW2. HBV genotype-A (GenBank Accession Number AB116094) was used for primer development and targeted conserved sequences within the S-gene and the partially overlapping Polymerase regions of the HBV genome (FIG. 1). Primers were manually designed, aided by PrimerExplorer4 and Primer3 web-interfaces, and synthesized by Integrated DNA Technologies (Coralville, Iowa) and EuroFins MWG Operon (Huntsville, Ala.). The primer sequences are shown in Table 1 (Example 1). The primers are stable for at least 3 years at −20 and −80° C.

Accelerated stability studies of reaction buffer: Aliquots of the MAB (Example 1) were stored at room temperature (22-25° C.) under sterile condition for approximately 6 months and then evaluated in LAMP for its stability when used to amplify nucleic acid. Also, accelerated stability studies were performed by heating freshly formulated MAB at 60° C. for 60 minutes, cooled at room temperature, heated again for an additional 30 minutes (3 times daily for 5 days), then used in LAMP reactions for detection of HBV-DNA.

Reaction mixture and conditions: Isothermal amplification of the HBV-DNA was performed in a 25 µL total reaction mixture. Reaction cocktail consisted of 12.5 µL of 2×MAB, 1.2 µM each of HBU-FIP and HBU-RIP, 0.8 µM each of HBU-LF and HBU-LR, 0.4 µM each of HBU-F3 and HBU-R3, and 8 Units of Bst DNA-polymerase (New England Biolabs, Ipswich, Mass.). Three to 10 µL of DNA or heat-treated plasma was applied as template. A no-template (water) control and DNA extracted from HBV-negative plasma were used as negative controls. DNA of known HBV genotypes was used as positive controls. Isothermal-amplification was performed at 60° C. for 60 minutes on a simple digital heat-block. All reagents were prepared in a PCR chamber and experiments were performed in a unidirectional flow-process with precautionary measures observed to avoid cross-contamination.

Analysis of reaction products: Five-microliters of HBV-LAMP products were electrophoretically analyzed on a 2.8% agarose-gel stained with GelRed nucleic acid stain (Phenix-Research, Candler, N.C.), run in 1×TAE-buffer at 100-volts for 50 to 55 minutes, and visualized with a UV-transilluminator at 302 nm. Amplification products were also visualized in the original reaction-tube by adding 0.5 µL of a 10× GelGreen fluorescence dye (Phenix Research) to 10 µL of LAMP reaction products, visualized with a UV-transilluminator at 302 nm.

Analytical sensitivity and specificity of HBV-LAMP assay: Analytical sensitivity was evaluated by testing 10-fold serial dilutions of HBV DNA. The assay detection limit was determined by analysis of 4 to 7 replicates of serially diluted HBV DNA (OptiQuant HBV-DNA Quantification-Panel). The analytical specificity of the HBV LAMP assay was investigated by testing HBV-specific primers against DNA (~30 ng) extracted from Cytomegalovirus-positive and Parvovirus-positive plasma specimens. Specificity of the HBV oligonucleotides was further evaluated by testing DNA (~50 ng) of *Leishmania major, Leishmania tropica*, and *Trypanosoma cruzi*.

Assay diagnostic sensitivity and specificity: The diagnostic sensitivity and specificity of HBV-LAMP assay was investigated by blind testing a total of 182 donor plasma specimens that were pre-selected using the Procleix® Ultrio® assay (Gen-Probe-Corporation, Emeryville, Calif.).

Time-point of assay detection: In order to determine the time-point at which HBV-DNA is amplified by the LAMP assay, time-course amplification studies were performed at 10, 20, 30, 40, and 60 minute time-points using 50 and 100 IU of HBV DNA per reaction. At the end of the indicated time-points, reaction tubes containing HBV DNA were removed from the heat-block and placed on ice to terminate the reaction.

Results

Detection of HBV-DNA: HBV DNA extracted from plasma standards of various HBV genotypes were used in the assay. Electrophoretic analysis of the LAMP products demonstrated successful detection of all 6 major HBV-genotypes (A to F) with a universal set of HBV-LAMP primers (FIG. 2A). The LAMP-reaction resulted in a unique laddering pattern of amplicons common to all genotypes detected (FIG. 2A). UV-visualization of LAMP products with GelGreen dye revealed a greenish-fluorescent glow in the reaction tubes that were positive for amplified HBV-DNA (FIG. 2B). No fluorescence or laddering pattern was observed for the no-template (water) control or the normal human plasma (FIGS. 2A and B).

Figures 3A, 3B:
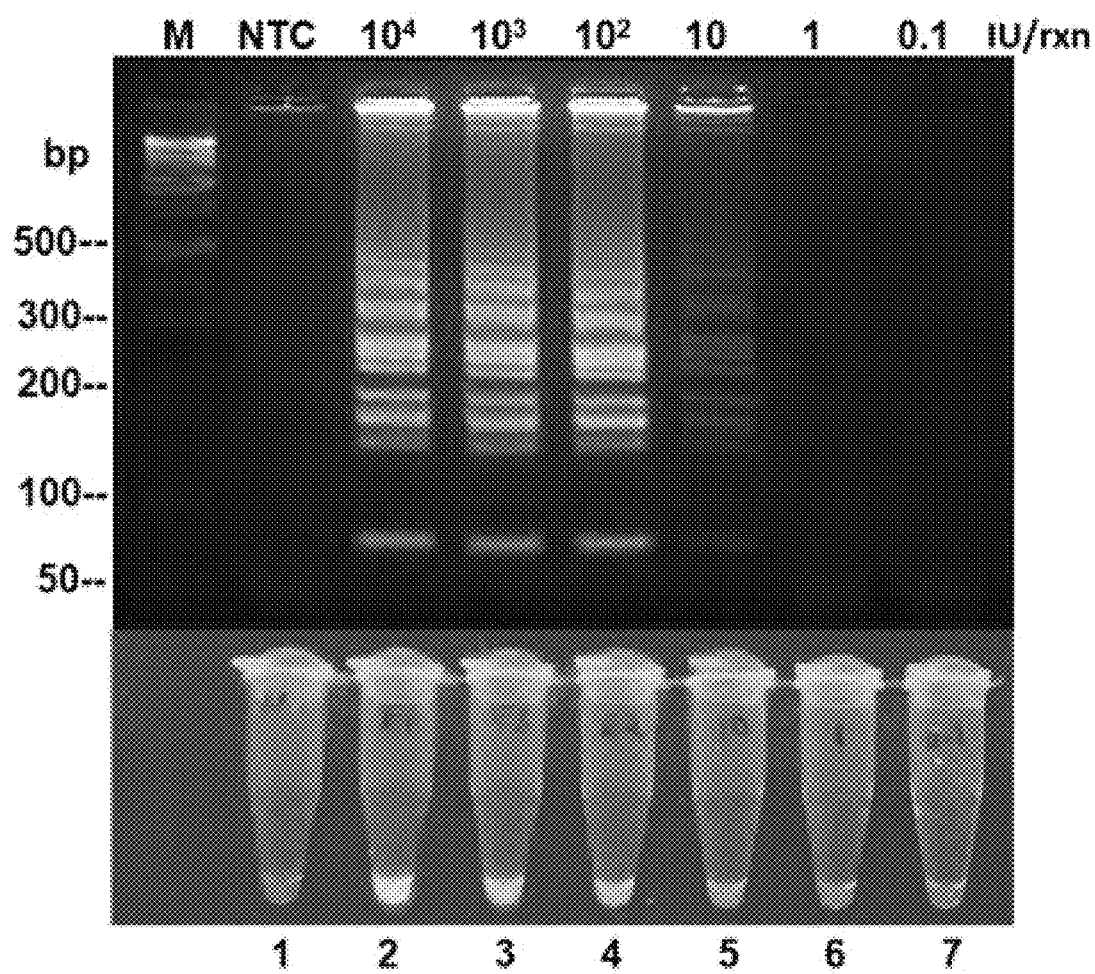
FIGS. 3A-D is a series of panels showing sensitivity and specificity of HBV LAMP assay primers.

Analytical and diagnostic sensitivity of HBV-LAMP assay: Assay sensitivity was evaluated by testing 10-fold serial dilutions of HBV DNA in the LAMP-reaction. The assay detected down to 10 IU per reaction of HBV-DNA (FIG. 3A). Addition of GelGreen™ fluorescent-dye to the reaction-tubes revealed a fluorescent glow with decreasing intensity from $10^4$ to 0.1 IU/reaction (FIG. 3B). Also, donor plasma samples (n=75) were tested to evaluate the diagnostic sensitivity of the assay. Test results revealed that the assay detected 69 of 75 (92%) as HBV-positive (Table 2). The undetected samples (n=6) had DNA levels below the assay detection-limit (~7-10 IU/reaction).

Figure 3C:
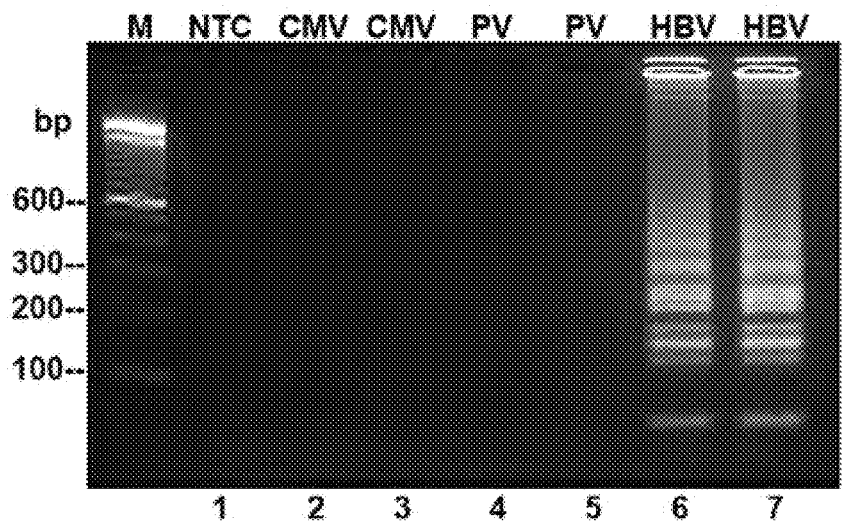
Figure 3D:
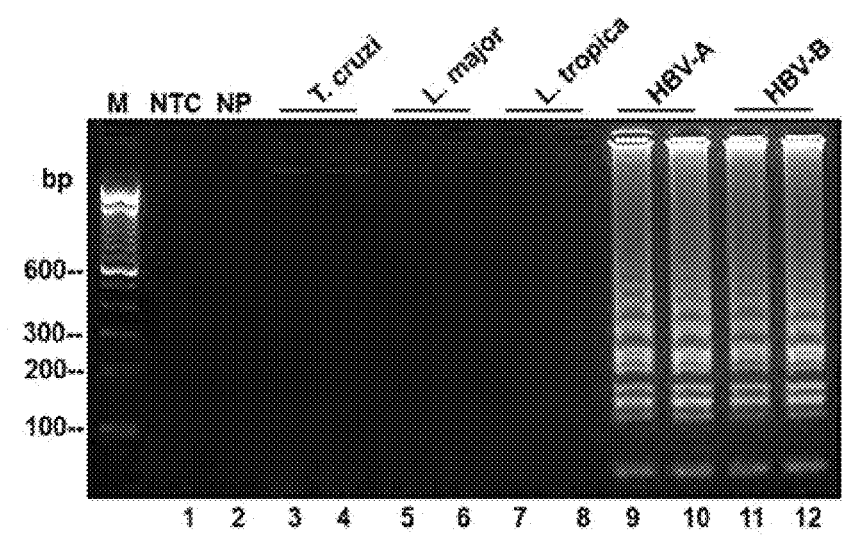

Analytical and diagnostics specificity of HBV-LAMP assay: The analytical specificity of the HBV-LAMP assay was investigated by testing DNA of CMV and PV, respectively. Electrophoretic analysis of test results revealed no detection (FIG. 3C). Also, specificity of the HBV oligonucleotides was evaluated by testing DNA of *L. major, L. tropica*, and *T. cruzi* in LAMP-assay. Results of the test also demonstrated no detection (FIG. 3D). In order to assess the diagnostic specificity of the assay, healthy human plasma specimens (n=107) were tested and all samples tested negative (100%) by the HBV-LAMP assay (Table 2).

TABLE 2

Clinical plasma specimens evaluated by the HBV LAMP assay

| Detection Method | DNA Extraction Plasma volume (µL) | DNA Amplification Reaction volume (µL) | DNA Amplification In put volume (µL) | Sensitivity HBV-positive plasma | Specificity Healthy/ negative human plasma | Total specimens tested |
|---|---|---|---|---|---|---|
| HBV-LAMP | 400 | 25 | 10 | 69/75 (92%) | 107/107 (100%) | 182 |
| Procleix Ultrio¶ | 500 | >500 | 500 | 75/75 (100%) | 107/107 (100%) | 182 |

¶Procleix sensitivity not absolute; based on positive donor-cohort.

Figures 4A, 4B:
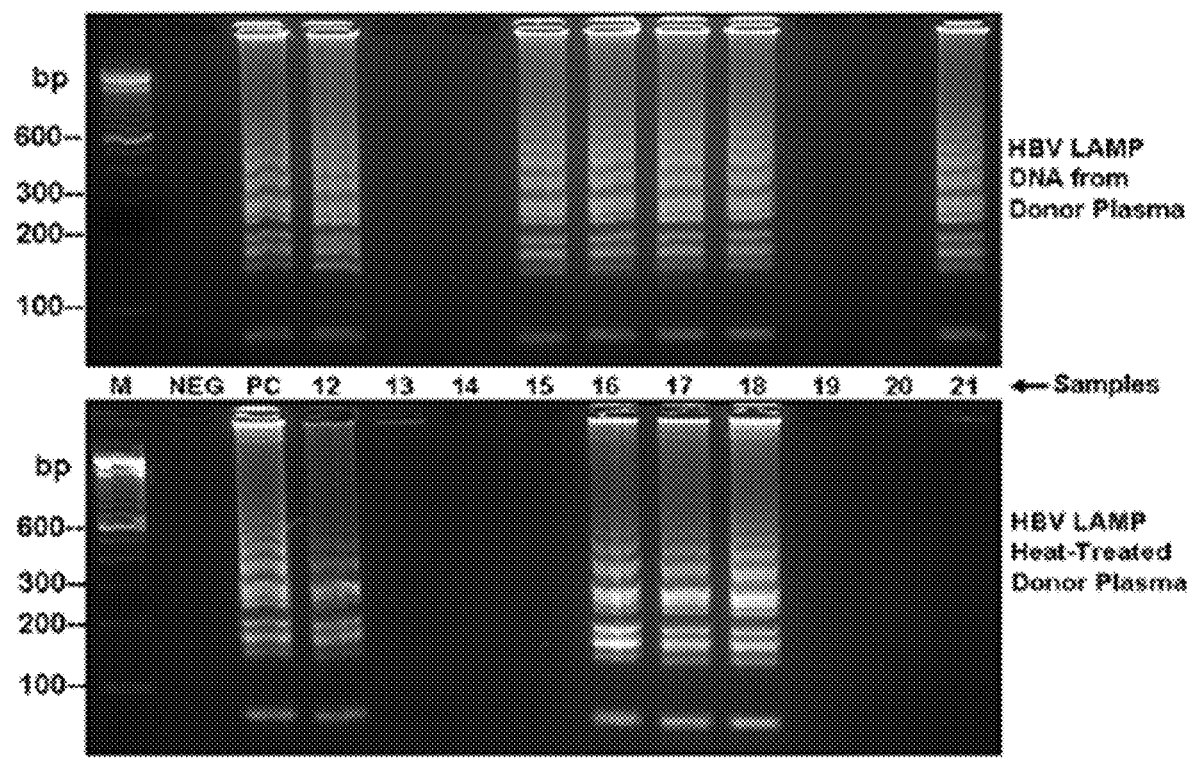
FIGS. 4A and B show detection of HBV DNA in donor plasma specimens.
FIG. 4B is a digital image of gel electrophoresis of HBV LAMP using the same samples as in FIG. 4A that were first heat-treated (without DNA extraction), centrifuged, and then the supernatant was used in the LAMP reaction. Lane M=100 bp DNA ladder; NEG=Negative (plasma) control; PC=positive control HBV genotype-A DNA ($10^3$ IU/reaction).

Evaluation of HBV-LAMP assay: To determine the field and clinical utility of the HBV-LAMP assay, experiments were conducted using donor plasma specimens from which DNA was extracted. Aliquots of the identical plasma samples were also heat-treated (without DNA extraction) and directly tested in the LAMP reaction. The results of agarose-gel electrophoresis demonstrated detection of HBV DNA using both extracted DNA and heat-treated plasma samples (FIGS. 4A and B). The assay detected two additional samples (#15 and 21) when extracted DNA was used, suggesting that the assay is more sensitive under those conditions.

Limit of detection: To determine the limit of detection of the HBV-LAMP assay, 4 to 7 replicates of serially diluted HBV DNA that was extracted from the OptiQuant HBV-DNA quantification plasma panel were assayed and analyzed. Results revealed a 100% detection rate for 25, 50, $10^2$, $10^3$, and $10^4$ IU of HBV DNA molecules per reaction, while 1 and 10 IU of HBV DNA were detected at 25% and 57% rates, respectively (Table 3).

TABLE 3

Probit data on LAMP assay amplification of various concentrations of HBV DNA.

| HBV DNA (IU/reaction) | Replicates Tested in Reaction | Number of Times Detected | Rate of Detection (%) |
|---|---|---|---|
| $10^4$ | 7 | 7 | 100 |
| $10^3$ | 7 | 7 | 100 |
| $10^2$ | 7 | 7 | 100 |
| 50 | 7 | 7 | 100 |
| 25 | 7 | 7 | 100 |
| 10 | 7 | 4 | 57 |
| 1 | 4 | 1 | 25 |
| 0.1 | 4 | 0 | 0 |

Figure 5:
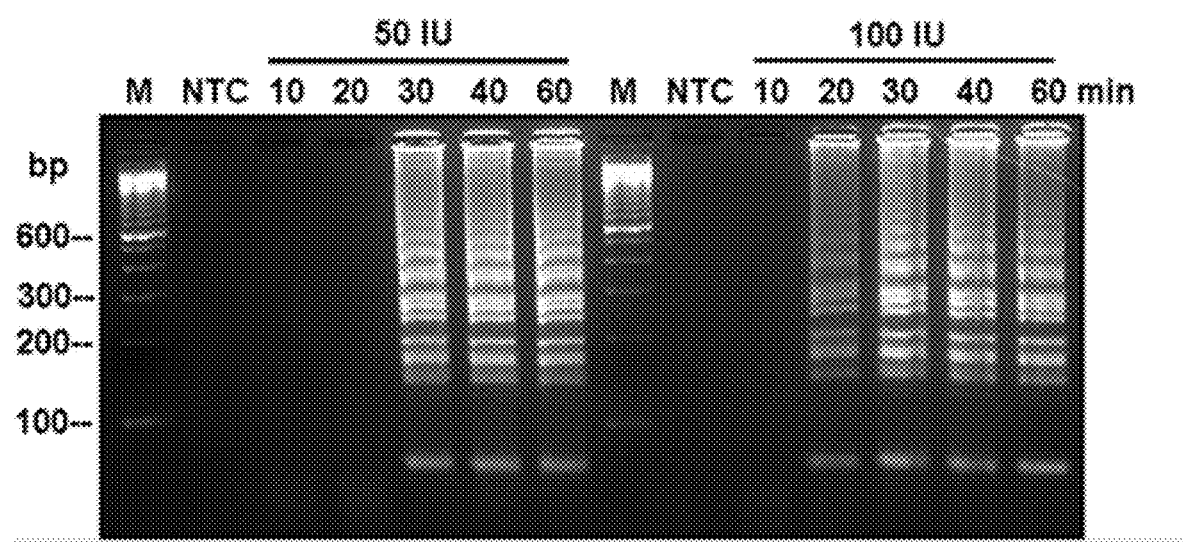
FIG. 5 is a digital image of gel electrophoresis of HBV LAMP reactions with 50 or 100 IU HBV DNA at defined time points. M=100 bp marker; NTC=No Template (water) control.

Time-point of detection: One of the advantages of the LAMP-assay is its rapid detection process. In order to evaluate the earliest time-point at which detection occurs, amplification of HBV DNA was tested at defined time intervals. Results of experiments revealed the assay detection of 50 IU of HBV DNA appeared at the 30-minute time-point, while 100 IU of HBV DNA was detected at the 20-minute time-point (FIG. 5).

Stability of reaction buffer: The stability of the Mannitol-Acetate-Buffer was evaluated as described in the method section. Electrophoretic analysis showed successful amplification of 25 IU/reaction of HBV DNA using fresh buffer regularly stored at −20° C., 10 IU/reaction of HBV-DNA when room-temperature-stored buffer (22-25° C.) was used, and 50 IU/reaction HBV-DNA when accelerated-aged buffer was used (FIG. 6A-C).

Discussion

The prevalence of HBV infection in underprivileged communities and regions of the world has generated heightened concerns in health care circles world-wide. HBV screening and diagnosis in resource-limited environments is often a challenging situation, because of time and cost-limitations, thus leaving infected individuals undiagnosed for several years. This underscores the need for a simple and rapid diagnostic and screening tool that is applicable not only in resource-limited settings, but also in any region of the world with high prevalence of HBV infections. In the developed world, the HBV LAMP assay could be useful to verify that a patient undergoing HBV treatment has achieved full virological suppression.

This example describes development and validation of a sensitive and rapid isothermal amplification assay for pan-detection of HBV-genotypes (A-F) in plasma specimens. The HBV LAMP assay offers several advantages over conventional "gold standard" methods like real-time PCR or ELISA: (i) the assay does not require sophisticated equipment and costly reagents; (ii) it requires less time (<60 minutes) to conduct; (iii) the assay is performed on a simple digital heat-block; and, (iv) does not require high level technical expertise. Thus, in regions with struggling national economies and lack of high-tech diagnostic equipment, these advantages make the HBV LAMP assay well-suited for use in such resource-limited settings for blood-screening and diagnosis of HBV infection.

The sensitivity of the HBV-LAMP assay was evaluated in order to assess its clinical and field applicability, using characterized standards and blinded clinical plasma-specimens. When compared to the FDA-licensed Procleix® Ultrio®-Plus dHBV test, the HBV-LAMP assay detected 69 of 75 (92%) HBV positive donor plasma specimens. The assay sensitivity approaches 100% with the use of fluorophores for detection (data not shown). As shown by the Probit data, the HBV LAMP Assay also revealed a 100% detection rate for 25, 50, $10^2$, $10^3$, and $10^4$ IU of HBV DNA per reaction, while 1 IU and 10 IU of HBV DNA were detected at 25% and 57% rates, respectively. These findings suggest that the LAMP-assay performed efficiently when used in testing and analysis of clinical specimens for HBV-infection.

Sample enrichment and volume play a critical role in detection sensitivity. The HBV-LAMP assay employed a smaller starting-volume for nucleic acid extraction and a smaller input-volume for amplification than the Procleix® Ultra® assay, yet yielded a sensitivity of 92%. Thus, given its plausible performance vis-à-vis the clinical and epidemiological relevance of HBV infection, the HBV LAMP assay is potentially applicable in field environment and in clinical-settings for screening and rapid detection of HBV-infection.

Notably, the HBV LAMP assay also successfully detected HBV DNA in heat-treated plasma, irrespective of the possible presence of potential amplification inhibitory substances that are found in blood-products (Al-Soud et al., *J. Clin. Microbiol.* 38:345-350, 2000; Al-Soud et al., *J. Clin. Microbiol.* 39:485-493, 2001). This method of template preparation (as opposed to nucleic acid extraction) contributed to the rapidity of the assay and simplified the detection process; however, an increase in the volume of starting material from 25 μL to a larger volume (for example, 100 μL) may be necessary to improve the sensitivity of detection when using heat-treated plasma for the reaction.

In consideration of detection specificity and accuracy in clinical diagnostics, primers in this assay were designed that specifically targeted conserved sequences of the S-gene and overlapping polymerase regions which show about 96% sequence identity and homology across the HBV genotypes (Osiowy et al. *J. Clin. Microbiol.* 41:5473-5477, 2003). The LAMP assay detected various HBV-genotypes (A-F), thereby demonstrating its global coverage of HBV detection. When healthy donor plasma samples (n=107) were tested, the HBV-LAMP assay revealed a diagnostic specificity of 100% as no amplification of HBV-DNA was observed in these specimens. This characteristic of the HBV-LAMP assay was also confirmed by its detection of only the target HBV-DNA without cross-reaction with CMV, PV, *T. cruzi*, and the *Leishmania* spp.

Within the context of today's globalization, people have been moving across international borders either for socio-politico-economic reasons or for recreational purposes. This rapid trend of human migration has influenced the spread of viral hepatitis and its changing epidemiology from Afghanistan to Pakistan, from the Indian sub-continent and Asia to Eastern Mediterranean, North Africa and the United States. Hence, the severity and prevalence of HBV emphasizes the need for a rapid and affordable diagnostic-screening tool as reported in this study, which could be used to investigate HBV-prevalence in different regions of the world.

A noteworthy advantage of the LAMP-assay reported in this study is its use of a thermo-stable reaction buffer (Mannitol-Acetate-Buffer) and the Bst DNA-polymerase, two major components that allowed preparation of reaction-mixture at room temperature as well as performance of amplification under isothermal conditions without compromising sensitivity. Bst DNA polymerase has DNA strand-displacement activity, while L-Proline has a destabilizing effect on the DNA double-helix, lowers the Tm of DNA, confers salinity tolerance and aids in DNA polymerase stability (Walker et al., *Nucl. Acids Res.* 20:1691-1696, 1992; Walker, *PCR Meth. Appl.* 3:1-6, 1993; Rajendrakumar et al., *FEBS Lett.* 410:201-205, 1997). In addition, D-Mannitol, a hygroscopic and osmopotent material also promoted buffer stability and robustness under thermo-stressed conditions (Dittmar et al., *Ind. Eng. Chem.* 27:333-335, 1935; Ohrem et al., *Pharm. Dev. Technol.* doi:10.3109/10837450.2013.775154, 2013). As demonstrated by the accelerated stability tests, the MAB surprisingly retained a considerable level of stability and robustness.

The advent of nucleic acid amplification tests in clinical diagnosis and donor blood-screening brought tremendous improvement by ensuring safety of blood-products and prevention of disease transmission. Yet, diagnostic tools such as PCR-based tests have inherent limitations which include the lack of rapidity, laborious performance process, use of cumbersome equipment, and being easily prone to contamination. In contrast, the HBV LAMP assay demonstrates ease of performance, rapidity, sensitivity, and the use of multiple-primers that makes the assay highly specific and less liable to cross-contamination. Considered in aggregate, the HBV LAMP detection assay reported in this study is rapid, simple to use, and specific.

Example 3

RT-LAMP Assay for Detection of Hepatitis C Virus

Introduction

Hepatitis C virus (HCV) is a single-stranded RNA virus of the Flaviviridae family (Moratorio et al., *Virol. J.* 4:79, 2007). Primarily transmitted through transfusion of contaminated blood, infection with HCV may go silent for several years and lead to chronic-active hepatitis and hepatocellular carcinoma (Ghany et al., *Hepatology* 4:1335-1374, 2009; Liang et al., *Ann. Int. Med.* 132:296-305, 2000; NIH Consensus Statement on Management of Hepatitis C; *NIH Consens. Sci. Statements* 19:1-46, 2002). Approximately 170 million people globally are infected with HCV. In the United States alone about 3.7 million people are diagnosed with HCV infection, wherein HCV genotypes 1 and 2 account for a majority of infections (Armstrong et al., *Ann. Int. Med.* 144:704-714, 2006; Zein, *Clin. Microbiol. Rev.* 13:223-235, 2000). There are six major genotypes of HCV with several subtypes found in different regions of the world (Lamballerie et al., *J. Gen. Virol.* 78:45-51, 1997; Simmonds, *Hepatology* 21:570-583, 1995; Simmonds et al., *Hepatology* 10:1321-1324, 1994). Thus, screening for HCV in blood is important in providing information on its prevalence in various populations and communities around the world, while identification of the specific HCV genotype is clinically important for implementing effective antiviral treatment (de Leuw et al., *Liv. Intl.* 31:3-12, 2011; Alestig et al., *BMC Inf Dis.* 11:124, 2011; Etoh et al., *BMC Res. Notes* 4:316, 2011). Therefore, there is a need for a specific, sensitive, simple, and robust diagnostic-screening test that can detect HCV infection in blood-derivatives and simultaneously provide genotypic information.

A plethora of diagnostic tests for detection and genotyping of HCV infection have been designed. These tests are expensive, labor-intensive, and require well-equipped laboratories and highly trained personnel to conduct (Rho et al., *J. Microbiol.* 46:81-87, 2008; Nolte et al., *J. Clin. Microbiol.* 33:1775-1778, 1995; Sabato et al., *J. Clin. Microbiol.* 45:2529-2536, 2007). Additionally, these tests are prone to cross-contamination and are further limited in their ability to detect and simultaneously identify the specific HCV genotype Corless et al., *J. Clin. Microbiol.* 38:1747-1752, 2000; Duarte et al., *PLoS One* 5:e12822, 2010). These limitations render current methods unsuitable for use in clinical settings in the developed-world setting and in resource-limited facilities mainly found in developing countries where sophisticated biomedical diagnostic equipment may be lacking. Here, we report the development and validation of the first rapid and sensitive reverse-transcription loop-mediated isothermal amplification and genotyping assay (RT-LAMP-G) for HCV infection.

The assay is simple, sensitive, and specific, and is performed on the basis of auto cycling strand-displacement DNA synthesis which produces long stem-loop products of multiple inverted repeats. The amplification process is accomplished within 60 minutes, utilizing thermostable enzymes, a robust thermostable reaction-buffer, and three sets of oligonucleotide that target conserved as well as sparsely polymorphic sequences in the 5'-non coding region (NCR) of the HCV genome. Here, we introduce a novel approach to HCV genotyping that has clinical and epidemiological applications in addition to its utility in resource-limited environments and developed world-settings.

Materials and Methods

Design of Oligonucleotides: Full-length sequences of various HCV genotypes (n=148) were obtained from the GenBank database and analyzed using CLUSTALW2. Primers were designed manually and electronically with the aid of PrimerExplorer-4 and Primer-3 web interfaces, using the 5'-NCR of selected HCV-candidate sequences (FIGS. 7A-D). In order to ensure genotype distinction, primers were designed to target sequences with sparse nucleotide diversity or polymorphism within the conserved 5'-NCR (Bukh et al., *Proc. Natl. Acad. Sci. USA* 89:4942-4946, 1992). A universal primer set and one set for each genotype were made (Table 1; Example 1). In order to ensure broader coverage for HCV 2 isolates, the 5'-end of primer sequence HCV2-R3 was designed with a "G" to "C" reverse-complementary nucleotide substitution at position one and a "C" to "T" substitution at position three. The oligonucleotides were synthesized by EuroFins-MWG-Operon (Huntsville, Ala.) and Integrated-DNA-Technologies (Coralville, Iowa).

Isolation of RNA: Total RNA was extracted from HCV reference and genotyping panels of WHO International Standard (OptiQuant-AcroMetrix/Life Technologies, Benicia, Calif. and SeraCare, SeraCare Life Sciences, Milford, Mass., respectively), and from blind clinical donor plasma (n=15). RNA was also isolated from the following materials: LB-piVE culture supernatant of HCV-1b (Silberstein et al., *PLoS Pathogen* 6:e1000910, 2010); HCV-2a strain J6/JFH-1 (supplied by C. M. Rice, Rockefeller University); HCV-3a clinical plasma samples (n=2; supplied Dr. Jack T. Stapleton, University of Iowa); and HCV-4a clinical serum specimens (n=3; provided by Dr. Marc Ghany and colleagues of the NIH Clinical Center, Bethesda-Maryland). Also, RNA was extracted from negative/normal human plasma (n=50). Extraction was performed with the QiaAmp® Viral RNA mini kit protocol (Qiagen, Germantown, Md.) with some modifications that included the following: (1) use of 200 µL of plasma, serum or culture-supernatant; (2) addition of RNAsecure™ (Ambion/Life Technologies, Grand Island, N.Y.) to a 1× final concentration in the lysis process and to the eluted RNA in order to protect the released/extracted nucleic acid from degradation; and (3) performance of all centrifugations at 6000×g for 1 minute. The eluted RNA was aliquoted and stored at −80° C. until needed for testing.

HCV Standards and Controls: Quantified RNA standards of HCV 1a, 1b, and 2a/c, as well as Dengue and West Nile viruses (Armored RNA®, Asuragen, Austin, Tex.) were used. Total RNA extracted from titered plasma panels of WHO International Standards containing HCV 1, 2, 3, and 4 (OptiQuant, AcroMetrix/Life Technologies and SeraCare) were also used. RNAs were serially diluted in nuclease-free water and used in amplification reactions.

HCV Diagnostic Genotyping Assay: Diagnosis and genotyping of HCV was performed by reverse-transcription isothermal amplification in a 25 µL total reaction mixture. The mixture comprised of 12.5 µL of 2×MAB (described in Example 1), 1 µM each of primers FIP and RIP; 0.6 µM each of primers LF and LR; 0.5 µM each of primers F3 and R3; 8 Units of Bst DNA polymerase (New England Biolabs); 5 U of cloned-AMV reverse-transcriptase (Invitrogen/Life Technologies); and 10 U of RNaseOut™ (Invitrogen/Life Technologies). RNA template volume of 1-5 µL was applied to the reaction. A no-template (water) control was included in all amplification runs in order to control for reagent integrity. Positive controls included known genotypes of HCV-RNA standards, while Dengue virus, West Nile virus (Asuragen), and normal human plasma served as negative controls. All reaction reagents were prepared in a PCR work-station (Plas Labs, Lansing, Mich.), with precautionary measures observed to prevent cross-contamination. Reactions were performed at 63.5° C. for 60 minutes on a portable digital heat-block (myBlock™, Benchmark Scientific, Edison, N.J.) and terminated by placing reaction tubes on ice.

Analysis of Amplicons: Reaction products were analyzed by running 5 µL of reaction products on a 2.8% agarose gel made up in 1×TAE (40 mM Tris, 20 mM acetic acid, 1 mM EDTA) and stained with GelRed (Phenix Research, Candler, N.C.). Products were electrophoresed for 50 minutes at 100 volts in 1×TAE buffer and visualized under UV transilluminator at 302 nm. Gels were photographed and documented using the G:Box gel documentation system (Syngene, Frederick, Md.). For rapid acquisition of results, 0.5 µL of a 10× GelGreen dye (Phenix Research) was added to 10 µL of reaction products in 0.2 mL reaction tubes. The tubes were then visualized under UV-transilluminator at 302 nm. Analysis of banding-patterns on the gel as well as visual interpretation of fluorescent color-change in reaction tubes was performed by at least three different laboratory personnel.

Sensitivity and specificity Studies: Sensitivity of the RT-LAMP genotyping assay was evaluated by testing serial dilutions of quantitated HCV RNA or plasma standards. At the end of the reactions, GelGreen fluorescent dye was added to the reaction-tubes in order to evaluate fluorescent-intensity in relations to level of HCV RNA detected.

Primer specificity and cross-reactivity were evaluated by cross-testing of oligonucleotides with HCV genotypes 1, 2, 3, and 4 and with RNA of Dengue and West Nile viruses. Most importantly, primer sets were evaluated for their ability to produce distinctly unique banding patterns for the HCV genotypes targeted for identification.

Time-Course for Detection of HCV RNA: In order to determine the time point at which HCV RNA was amplified, time-course experiments were conducted by testing approximately 15 and 75 IU/reaction of extracted HCV RNA using the universal primers set and defined reaction time intervals. Reaction tubes containing RNA were sequentially taken off the heat-block at designated time points (25, 35, 45, and 60 minutes), while negative control reactions ran for 60 minutes. The resulting products were analyzed by agarose-gel electrophoresis.

Preparation of Plasma as Substrate for Target: Plasma material was heated for viral lysis and applied to the reaction in order to evaluate the ability of the assay to detect HCV RNA using heat-treatment without RNA extraction. Therefore, 25 µL of plasma standards of varying HCV titers (OptiQuant-AcroMetrix/Life Technologies) were thawed on ice, briefly vortexed and then heated at 33.5° C. for 5 minutes on a digital heating block; the tubes were pulse-vortexed again and heated for an additional 5 minutes. Next, 3-5 µL of heat-treated plasma material was directly applied to the reaction-mixture and subjected to the 63.5° C. amplification-reaction for concurrent viral-lysis and detection of HCV RNA.

Assay evaluation with donor specimens: The HCV RT-LAMP genotyping assay was validated by testing donor plasma specimen (n=17) and donor serum specimens (n=3) mentioned above. Also, normal/healthy human plasma specimens (n=50) were used in this study. Total RNA was extracted from the specimens and 3-5 µL was subjected to isothermal amplification as described above. Reaction products were resolved on a 2.8% agarose gel to analyze the resulting banding pattern.

Results

Figures 8A, 8B:
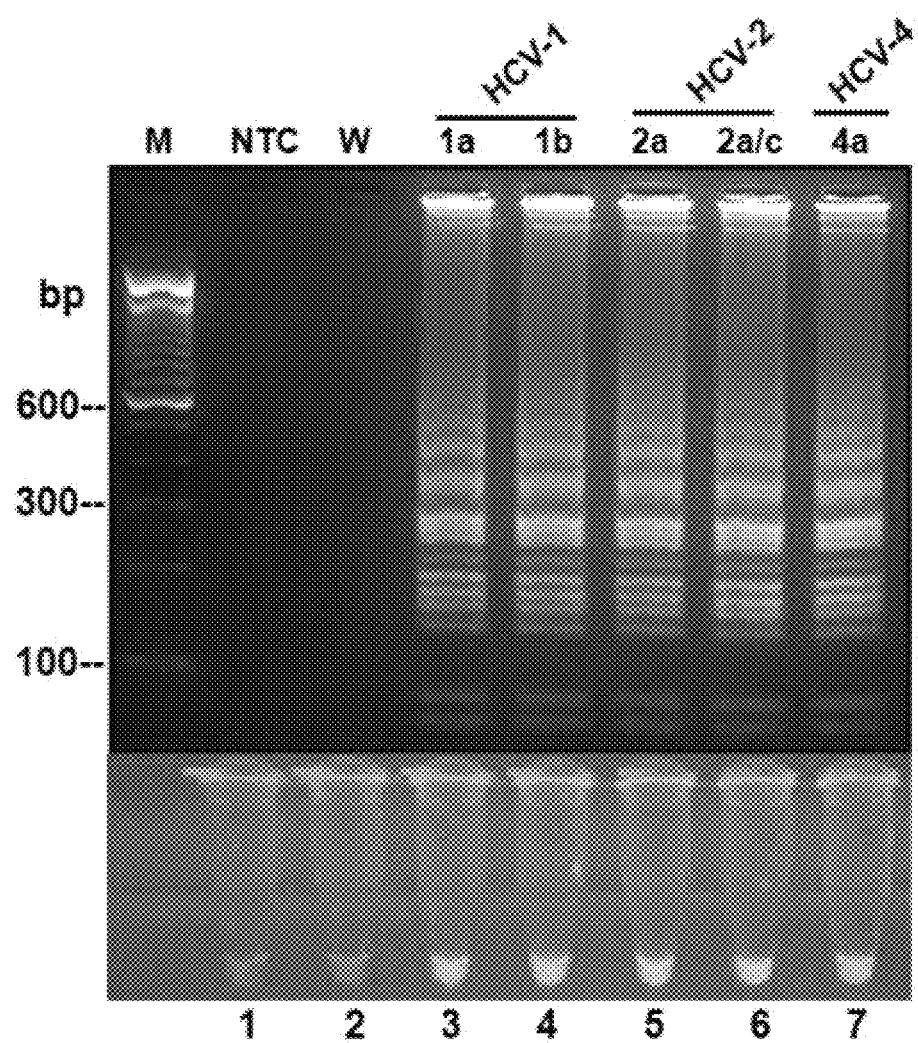
FIGS. 8A and B are digital images showing detection of HCV-1, HCV-2, and HCV-4 using the universal HCVU LAMP primers.
FIG. 8B is a digital image of reactions with addition of 10 µl of 10× GelGreen dye to the final reaction tubes and visualized under UV illumination at 302 nm. Tubes correspond to the lanes in FIG. 8A.

Specificity and Analysis of Products: RT-LAMP assay was used to detect HCV-RNA with universal or genotype-specific HCV primers. The cross-reactivity of the primers and their ability to specifically amplify the 5'-NCR of specific HCV genotypes were evaluated. Plasma standards from patients infected with known genotypes of HCV were used. Electrophoretic analysis demonstrated successful amplification of RNAs of HCV genotypes 1, 2, and 4 by the universal primer set (HCVU; Table 1). The oligonucleotide-set produced a ladder-like banding pattern common to HCV 1, 2, and 4 (FIG. 8A). For rapid acquisition of results, GelGreen intercalating dye was added to the reaction tubes at the end of the amplification and revealed an intense greenish fluorescent color in reaction tubes with amplified products (FIG. 8B).

Figure 9B:
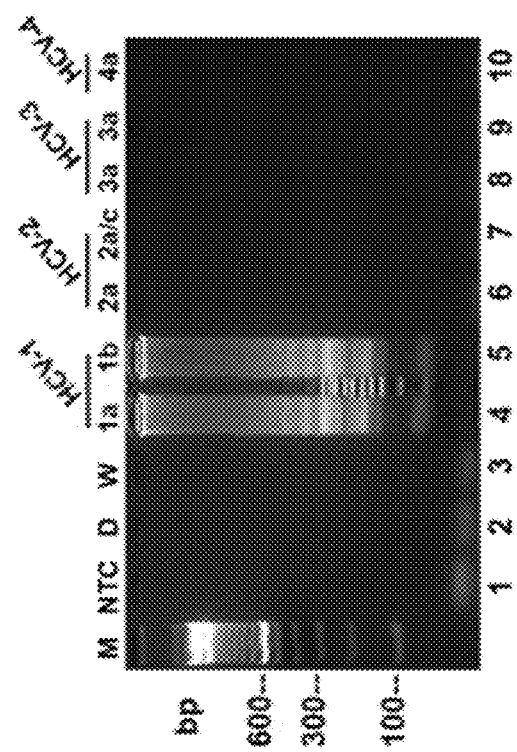
FIG. 9B shows HCV-2 primer set.
Figure 9A:
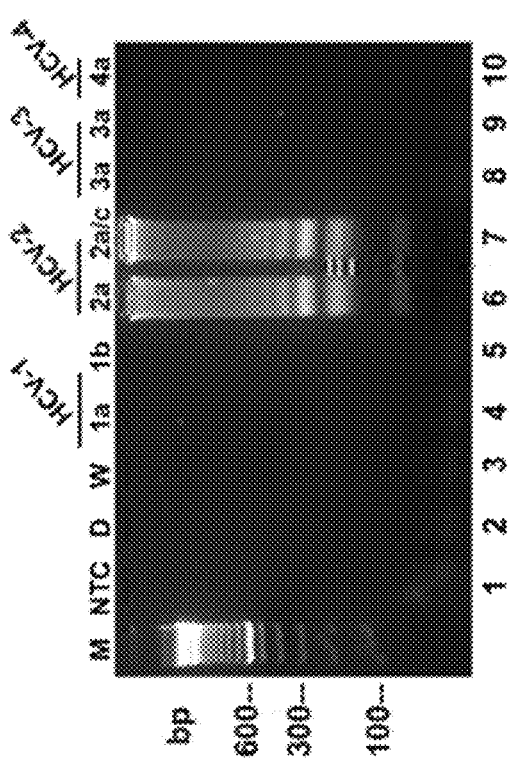
FIG. 9A shows HCV-1 primer set.
Figure 9D:
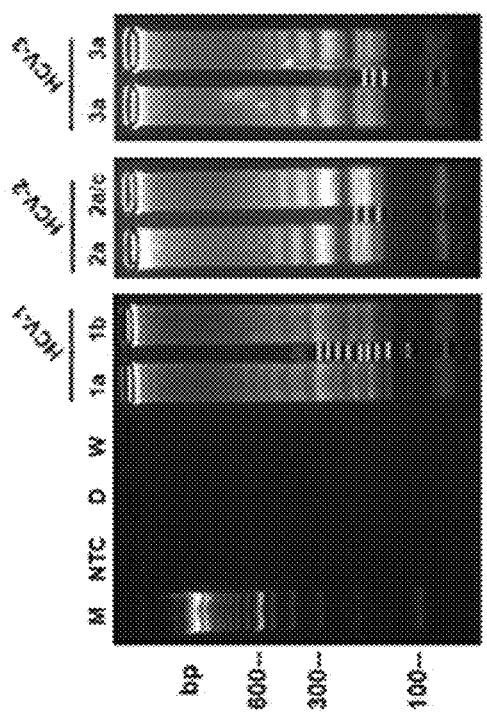
FIG. 9D juxtaposes the positive samples from FIGS. 9A-C to demonstrate the unique banding pattern obtained with each primer set (indicated with the lines between lanes in each panel). Lane M=100 bp marker; Lane 1=No-Template Control (NTC); Lane 2: D=Dengue Virus RNA ($4 \times 10^6$ copies/rxn); Lane 3: W=West Nile Virus ($2.85 \times 10^6$ copies/rxn); Lane 4: HCV-1a ($10^6$ IU/rxn); Lane 5: HCV-1b ($5 \times 10^5$ IU/rxn); Lane 6: HCV-2a ($5 \times 10^4$ IU/rxn); Lane 7: HCV-2a/c ($5 \times 10^4$ IU/rxn); Lanes 8 and 9=HCV-3 (5 ng); and Lane 10: HCV-4a (180 IU/rxn).
Figure 9C:
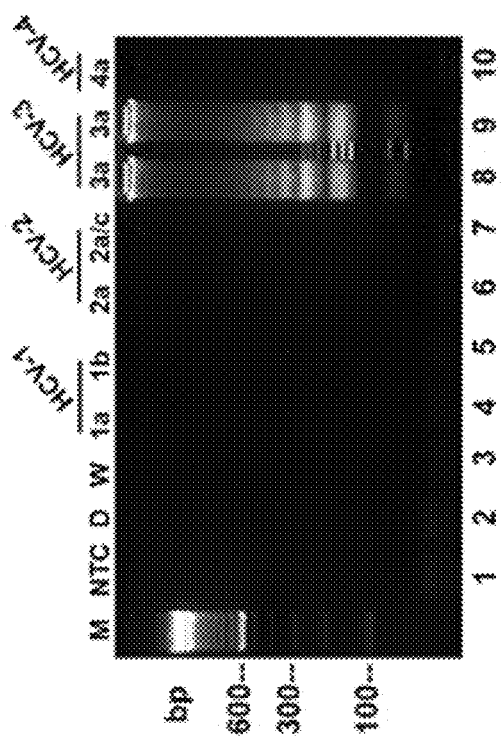
FIG. 9C shows HCV-3 primer set.

Genotype-specific primer sets were designed to detect HCV genotypes 1, 2, and 3 (Table 1, Example 1). The specific primer sets produced a banding pattern of amplicons that were distinct and unique to each genotype (FIG. 9A-D). The primer set targeting HCV genotype 1 detected both genotypes 1a and 1b, but did not detect genotypes 2, 3 or 4 (FIG. 9A). Similarly, the primer sets that targeted HCV-genotypes 2 and 3 specifically detected the appropriate genotype (FIGS. 9B and C). None of the primer sets reacted with either RNAs of Dengue or West Nile viruses (FIG. 9A-D), demonstrating that the primers did not cross-react with other Flaviviridae.

Assay Sensitivity: The assay sensitivity was determined by testing serial dilutions of known concentrations of extracted HCV RNA from plasma standards and heat-treated plasma standards (OptiQuant-AcroMetrix/Life Technologies and SeraCare) as quantitated by the manufacturer.

Results of electrophoretic analysis demonstrated detection of 25 IU/reaction of HCV RNA using heat-treated plasma without RNA extraction (FIG. 10A). When purified RNA from plasma standards was tested, the assay showed detection of 7 IU of HCV-RNA per reaction (FIG. 10B). Addition of GelGreen fluorescent dye to the reaction-tubes revealed a fluorescent-glow with decreasing intensity from 180 to 1.4 IU/rxn of HCV-RNA (FIG. 10C).

Figure 12A:
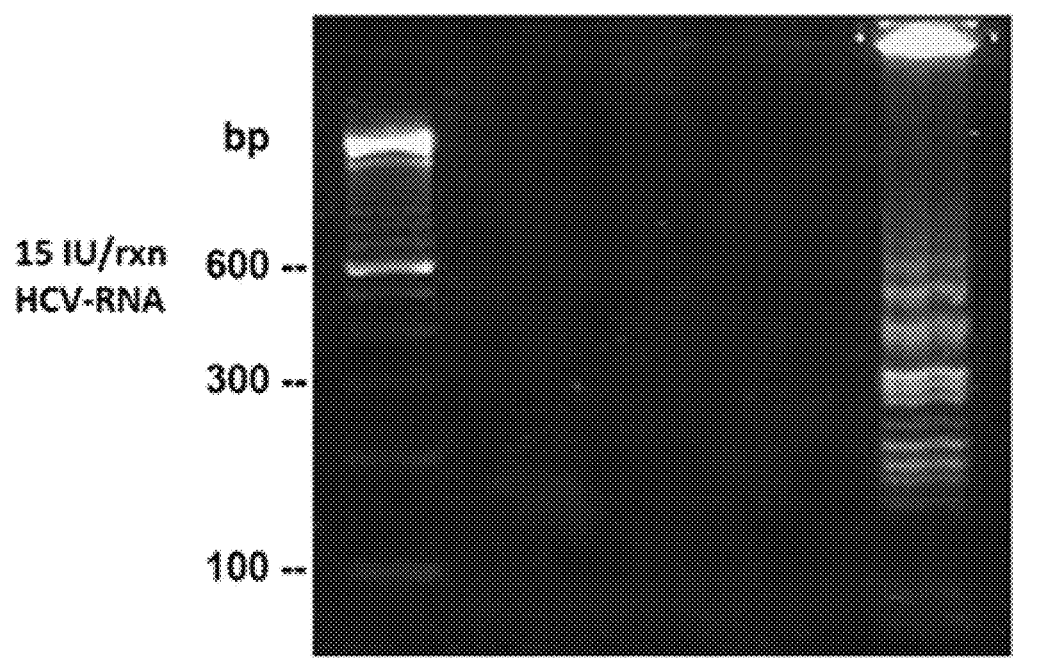
FIGS. 12A and B show the time course of detection of HCV-4a RNA with universal HCV primer set. Reactions contained 15 IU/reaction (FIG. 12A) or 75 IU/reaction (FIG. 12B) of HCV RNA.

Detection of HCV Genotypes in Donor Specimens: In order to determine the clinical applicability of the RT-LAMP genotyping assay, total RNA was extracted from donor plasma specimens (n=17) and serum specimens (n=3) and then tested using the genotype-specific primers (FIGS. 12A and B). Thirteen (13) donor plasma specimens tested positive for HCV-1, two (2) specimens tested positive for HCV-2, while two (2) specimens tested positive for HCV-3 (Table 4). Electrophoretic results are shown for some of the HCV-1 (FIG. 11A) and HCV-2 (FIG. 11B) samples. The three known HCV genotype 4 serum specimens tested positive for HCV as indicated by the presence of banding-pattern generated by the universal primer set (FIG. 11C; Table 4). Hence, all the infected donor plasma and serum specimens (n=20) tested positive for the presence of HCV and with genotype distinction (Table 4), while all the normal/negative human plasma specimens (n=50) tested negative (data not shown).

TABLE 4

Detection and validation of HCV RT-LAMP genotyping assay with donor plasma and serum specimens

| Sample ID | Specimen Type | RT-LAMP Results | HCV Genotype Identified |
|---|---|---|---|
| P10 | Plasma | + | 1 |
| P28 | Plasma | + | 1 |
| P30 | Plasma | + | 2 |
| P31 | Plasma | + | 1 |
| P32 | Plasma | + | 2 |
| P37 | Plasma | + | 1 |
| P50 | Plasma | + | 1 |
| P53 | Plasma | + | 1 |
| P55 | Plasma | + | 1 |
| P65 | Plasma | + | 1 |
| P71 | Plasma | + | 1 |
| FDA-019 | Plasma | + | 1 |
| FDA-034 | Plasma | + | 1 |
| FDA-035 | Plasma | + | 1 |
| FDA-036 | Plasma | + | 1 |
| P154 | *Plasma | + | 3 |
| P390 | *Plasma | + | 3 |
| S1 | ʲSerum | + | 4 |
| S2 | ʲSerum | + | 4 |
| S3 | ʲSerum | + | 4 |

Figure 12B:
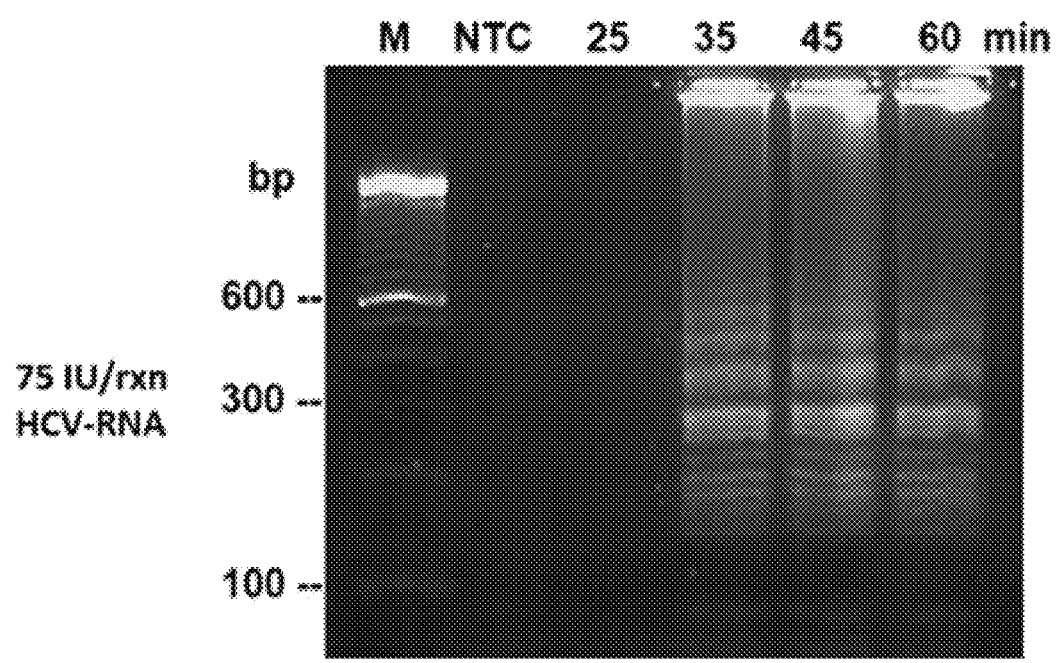

Positive detection (+); *Plasma previously identified to be HCV3-positive; ʲSerum previously known to be HCV4-positive;

Time course for Detection and Rapid Visualization: To establish the time point at which amplification occurs, 15 and 75 IU of RNA were tested per reaction using primers-set HCVU. Results demonstrated amplification of 15 IU of RNA at 60 minutes (FIG. 12A), while amplification of 75 IU was observed at 35 minutes (FIG. 12B).

Discussion

This example describes a specific, simple, sensitive and rapid isothermal amplification assay for genotyping of HCV and rapid detection of infection. This assay demonstrates salient advantages over methods that require intensive labor and exotic equipment. First, the HCV RT-LAMP genotyping assay was performed as a one-step-procedure, thus obviating the need for an extra cDNA-synthesis step; it utilized two thermostable enzymes (Bst DNA polymerase and cloned-AMV reverse-transcriptase) that catalyzed both synthesis and amplification of the HCV-RNA in a single reaction-tube, using a single temperature. Second, the assay employed three pairs of gene-specific primers directed at specific regions on the HCV genome, thus ensuring specificity and amplification efficiency. Third, the assay detected and simultaneously identified the HCV-genotype tested without requirement for extra genotyping procedure. Fourth, test-results were available in approximately 75 minutes, instead of the 3 to 5 hours required for other genotyping and detection-formats in which products are separately genotyped by restriction enzyme analysis, reverse hybridization, or nested RT-PCR.

In regions of the world with high prevalence of HCV infection, surveillance and epidemiological studies are periodically conducted in order to establish distribution patterns. This requires a diagnostic assay that is sensitive and specific. In our study, the HBV RT-LAMP genotyping assay demonstrated a detection sensitivity of 25 IU/reaction of HCV-RNA using heat-treated template (without RNA extraction), while detection of 7 IU/reaction of HCV-RNA was achieved when extracted RNA was used. Addition of GelGreen-intercalating dye to the tubes at the end of the reactions allowed for naked-eye rapid visualization of the assay detection-level of as little as 1.4 IU of HCV-RNA. In addition, the assay detected HCV-RNA in all 20 infected clinical donor specimens, thus revealing a 100% diagnostic sensitivity. The primer specificity of this assay is highly plausible as the amplification yielded detection of only HCV-RNA and the specific HCV-genotypes tested for, but reacted negative to RNAs of phylogenetically related viruses (Dengue and West Nile).

The 5'-NCR of the HCV genome was utilized for primer design due to its highly conserved nature across the HCV genotypes. For genotype-identification, this study exploited the sparse nucleotide diversity and polymorphism that exist within the 5'-NCR among the HCV genotypes. This approach contributed to the high specificity of genotype-identification, thereby clearly and accurately distinguishing between HCV 1, 2, and 3 as indicated by the difference in the banding-patterns for each genotype. This characteristic of the assay was validated by testing clinical samples. When donor plasma samples were tested by the RT-LAMP-Genotyping method, the test detected and accurately differentiated the clinical samples that were positive for HCV-1, 2, and 3. All 50 negative/normal human plasma tested negative, thereby demonstrating a diagnostic specificity of 100%. Furthermore, when donor serum samples were employed as test-substrates, the assay detected the presence of HCV in all three serum-specimens using the universal primer set-HCVU. HCV-3 was not tested with the universal primer set, because of its unavailability at the time testing. Collectively considered, these results demonstrate the capability of the assay to detect HCV, including genotype 4, in plasma and serum. The results have also demonstrated the specificity of the isothermal assay for detection and simultaneous genotyping of HCV, thus rendering the assay potentially applicable in clinical settings where genotype information is important in designing targeted therapeutic management of infected patients.

A major defining characteristic of the HBV RT-LAMP assay is the demonstration of specificity not only by absence of non-specific bands in the amplification products, but by the demonstration of genotype-specific banding patterns of the targeted genomic sequences. This enables an investigator or end-user to distinguish true positive amplification patterns from atypical band-laddering that may occur in a reaction due to non-specific priming (Curtis et al., *J. Med. Virol.* 81:966-972, 2009). A review of the literature revealed studies which utilized the 5'-NCR for primer design and have attempted the use of the RT-LAMP method for HCV detection (Esfahani et al., *Af. J. Microb.* 4:2580-2586, 2010; Wang et al., *FEMS Immunol. Med. Microbiol.* 8:144-147, 2011). Notably, these studies were confined only to detection, while another study was performed as a two-step method. Also, these studies failed to demonstrate distinguishing pattern-formation of amplicons of the HCV genotypes tested (Esfahani et al., *Af. J. Microb.* 4:2580-2586, 2010; Wang et al., *FEMS Immunol. Med. Microbiol.* 8:144-147, 2011). In contrast, our test was performed as: (1) a one-step procedure, (2) a detection and genotyping method, and (3) demonstrated distinctive genotype-unique banding-patterns of HCV 1, 2, and 3.

Rapid, simple, and accurate identification of pathogens are important for timely therapeutic intervention, and for disease control and surveillance. This concern was addressed by simplifying the substrate preparation process. Plasma standards were heat-treated and used as a template in the amplification-reaction, thereby obviating the extra RNA extraction step and saving time. Use of fluorescence dyes for immediate end-point-read-out also added to the rapidity and simplicity of the assay by obviating gel-end-point analysis. Additionally, the assay accurately detected HCV RNA without assay efficiency being compromised by PCR inhibitory substances that are usually found in blood components and tend to inhibit PCR methods (Al-Soud et al., *J. Clin. Microbiol.* 38:345-350, 2000; Al-Soud et al., *J. Clin. Microbiol.* 39:485-493, 2001).

In conclusion, the HCV RT-LAMP genotyping assay described in this example has demonstrated its sensitivity, specificity, robustness, and ability to accurately identify HCV-RNA at the genotypic level. This assay may be used to aid clinicians in designing genotype-targeted therapy and follow-up of patients on antiviral treatments. Due to its simplicity and lack of requirements for elaborate equipment or extensive freezer storage conditions, the RT-LAMP-G assay has also shown its suitability for clinical point-of-care application and epidemiological studies in resource-limited environments, HCV-endemic regions, and in developed world-settings.

Example 4

RT-LAMP Assays for Detection of Human Immunodeficiency Virus, Hepatitis E Virus, Dengue Virus, and West Nile Virus Methods LAMP Assays: Genotyping of HIV, HEV, DENV, and WNV was performed by reverse-transcription isothermal amplification in a 25 µL total reaction mixture. The mixture comprised 12.5 µL of 2×MAB (described in Example 1), 1 µM each of primers FIP and RIP; 0.6 µM each of primers LF and LR; 0.5 µM each of primers F3 and R3; 8 Units of Bst DNA polymerase (New England Biolabs); 5 U of cloned-AMV reverse-transcriptase (Invitrogen/Life Technologies); and 10 U of RNaseOut™ (Invitrogen/Life Technologies). RNA template volume of 1-5 µL (extracted RNA or quantitated human plasma standard) was applied to the reaction. A no-template (water) control was included in all amplification runs in order to control for reagent integrity. All reaction reagents were prepared in a PCR work-station (Plas Labs, Lansing, Mich.), with precautionary measures observed to prevent cross-contamination. Reactions were performed at 60° C. for 60 minutes on a portable digital heat-block (myBlock™, Benchmark Scientific, Edison, N.J.) and terminated by placing reaction tubes on ice.

Reaction products were analyzed by running 5 µL of reaction products on a 2.8% agarose gel made up in 1×TAE (40 mM Tris, 20 mM acetic acid, 1 mM EDTA) and stained with GelRed (Phenix Research, Candler, N.C.). Products were electrophoresed for 50 minutes at 100 volts in 1×TAE buffer and visualized under UV transilluminator at 302 nm. Gels were photographed and documented using the G:Box gel documentation system (Syngene, Frederick, Md.).

Results

Figure 13:
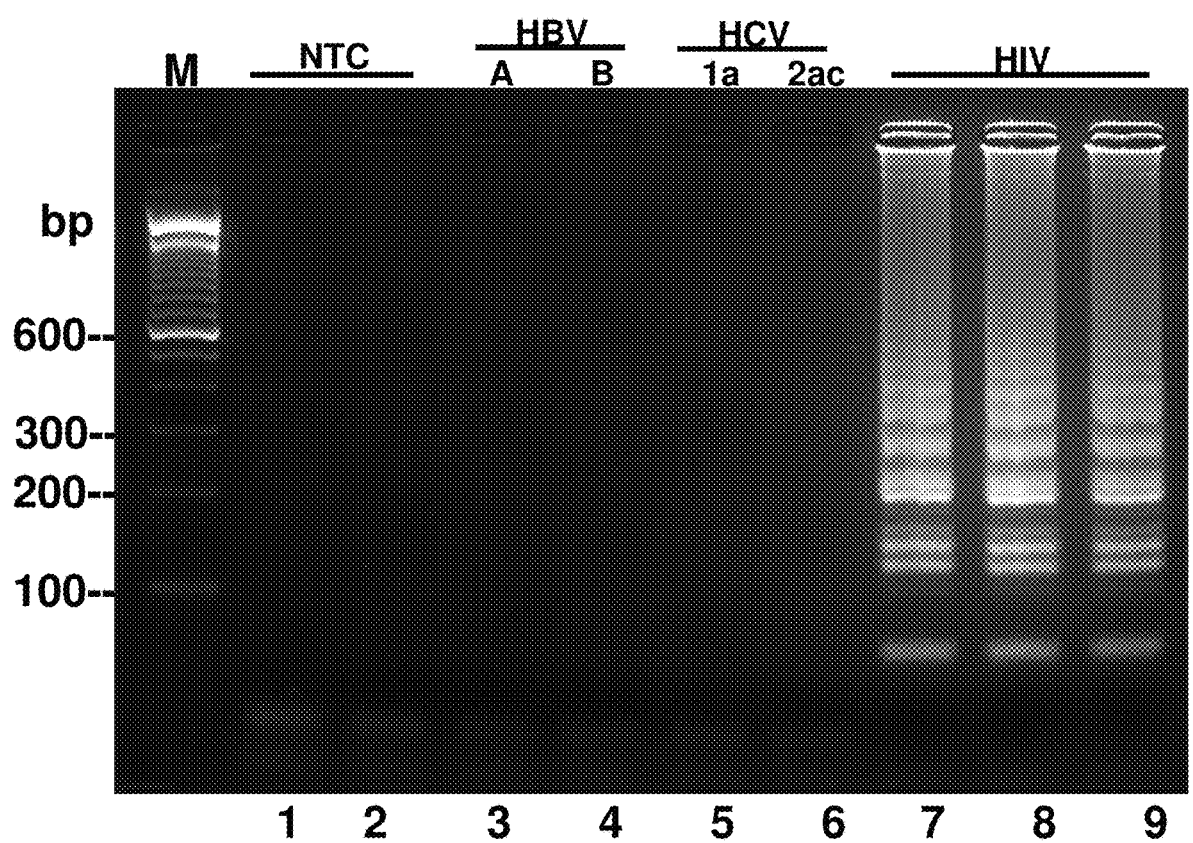
FIG. 13 is a digital image of electrophoresis of LAMP reaction products using HIV-1 primer set. Lane M=100 bp marker; Lanes 1-2=No-Template Control (NTC); Lane 3: HBV genotype A (90 IU/rxn); Lane 4: HBV genotype B (90 IU/rxn); Lane 5: HCV-1a (10 IU/rxn); Lane 6: HCV-2a/c (10 IU/rxn); Lanes 7-9: HIV ($10^3$ IU/rxn).
Figure 14:
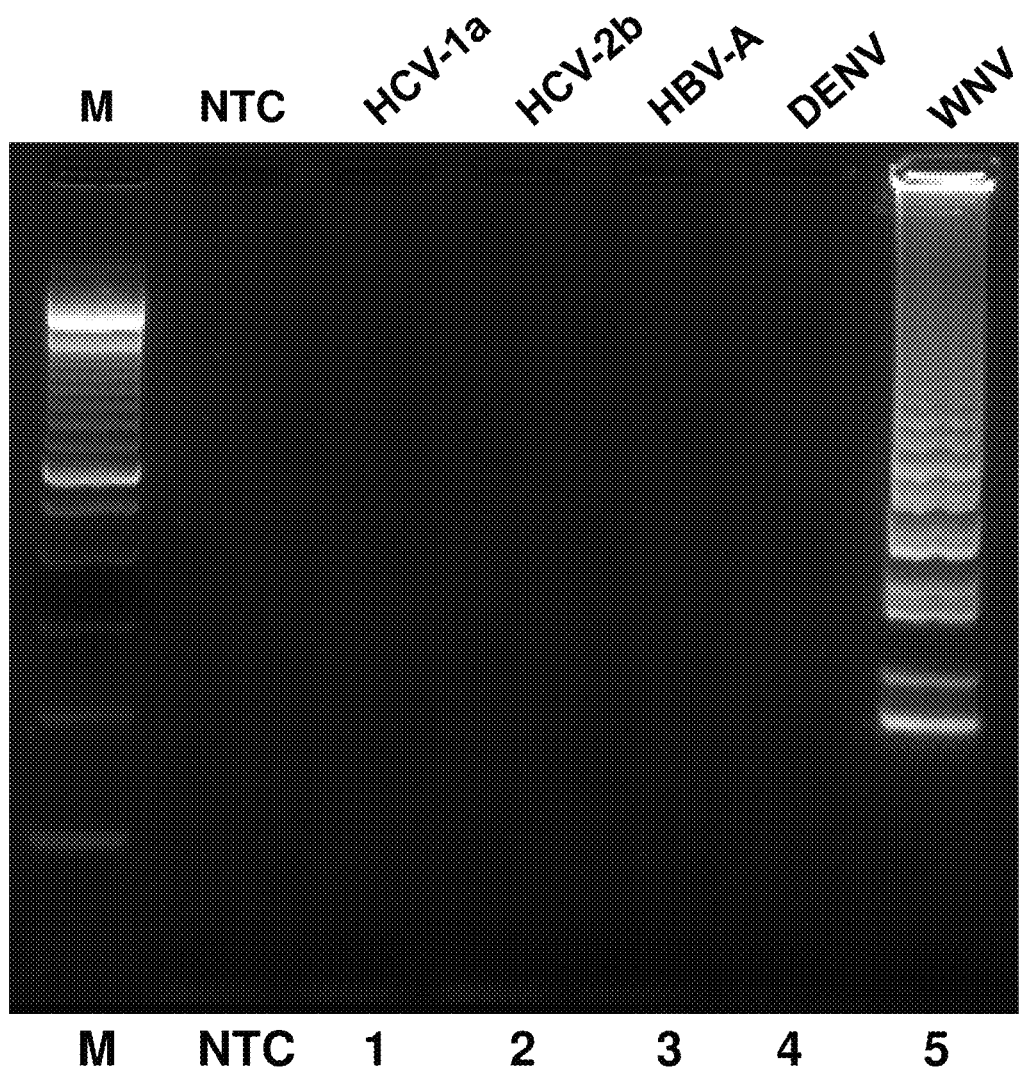
FIG. 14 is a digital image of electrophoresis of LAMP reaction products using WNV primer set. Lane M=100 bp marker; NTC: No-Template Control; Lane 1: HCV-1a ($10^5$ IU/rxn); Lane 2: HCV-2b ($10^5$ IU/rxn); Lane 3: HBV genotype A (180 IU/rxn); Lane 4: DENV ($10^4$ copies/rxn); Lane 5: WNV ($10^4$ copies/rxn).
Figure 15:
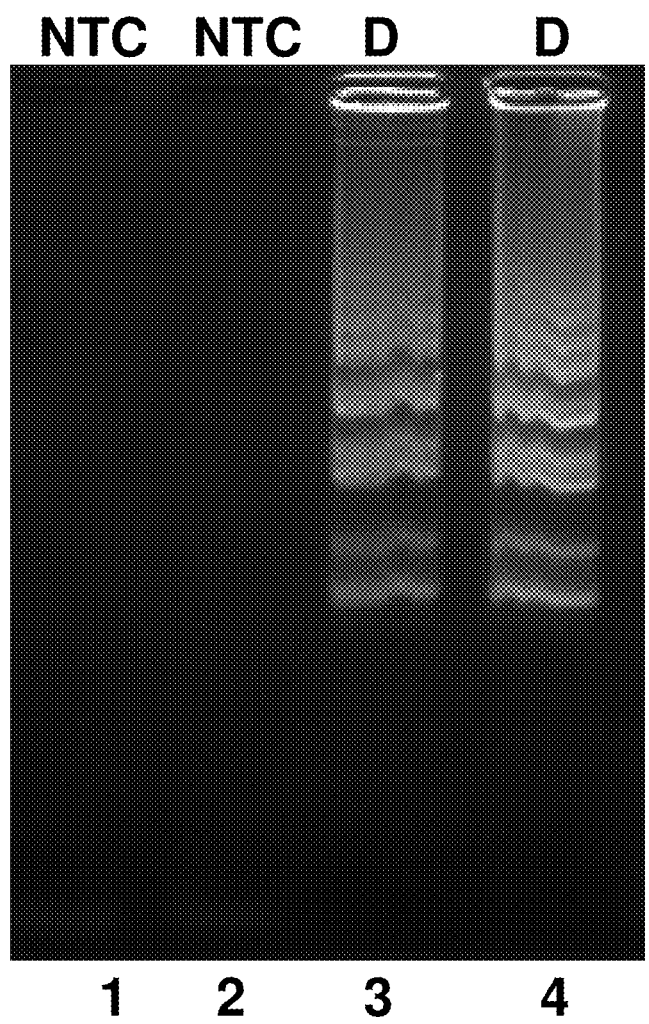
FIG. 15 is a digital image of electrophoresis of LAMP reaction products using DENV D1 primer set. NTC=No-Template Control; D=DENV-1 (104 copies/rxn).
Figure 16A:
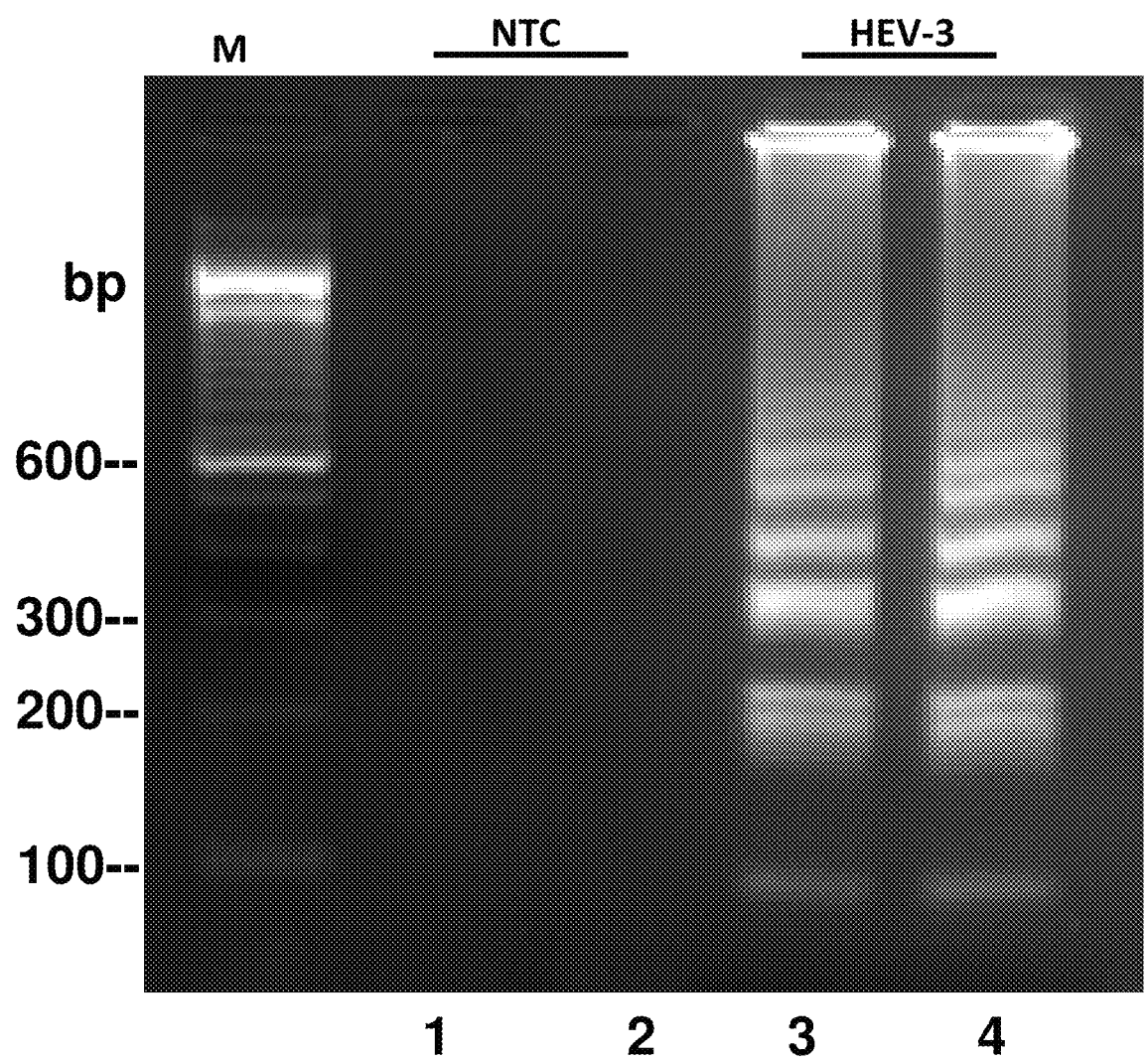
FIGS. 16A and B are digital images of electrophoresis of LAMP reaction products using HEV primer set.
Figure 16B:
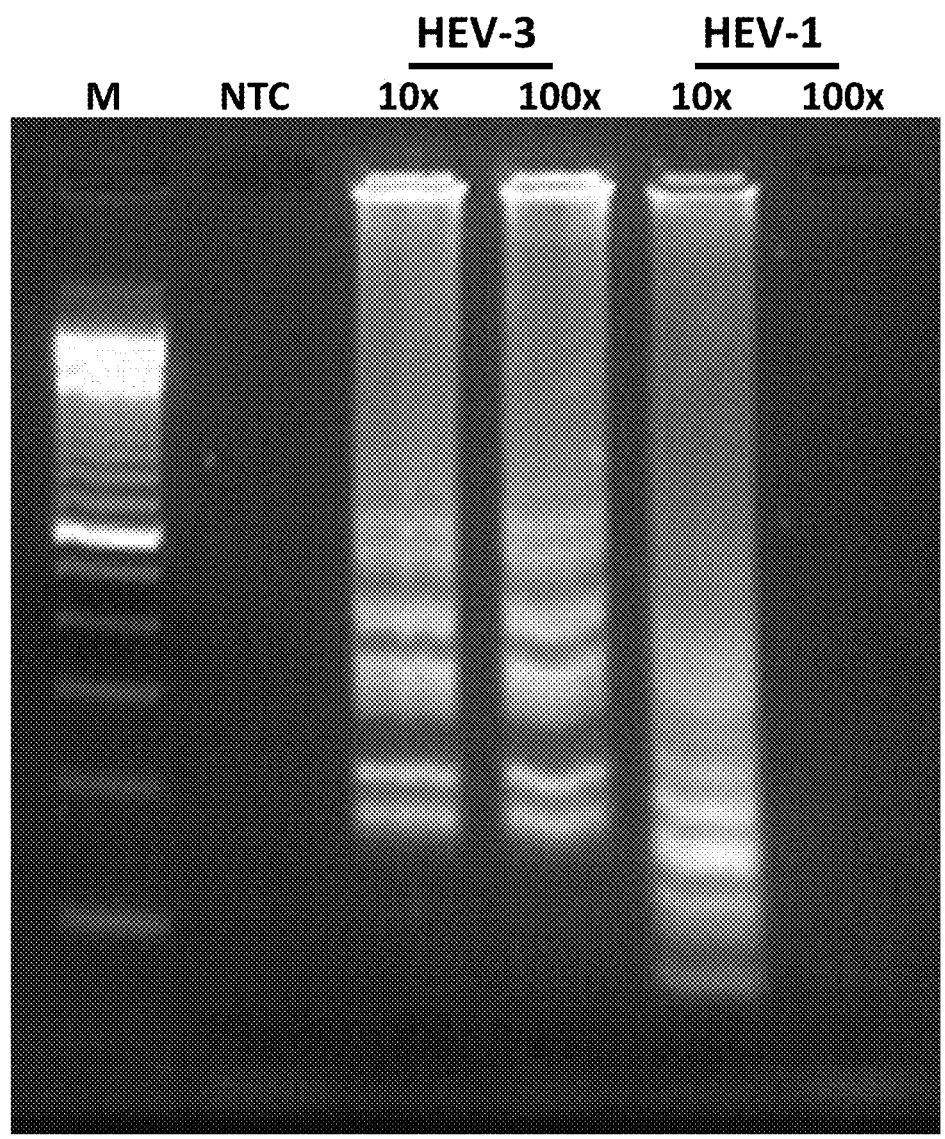
FIG. 16B shows gel electrophoresis of 10-fold (38.5 ng) and 100-fold (3.85 ng) dilutions of HEV-1. M=100 bp marker; NTC=no template control.
Figure 17A:
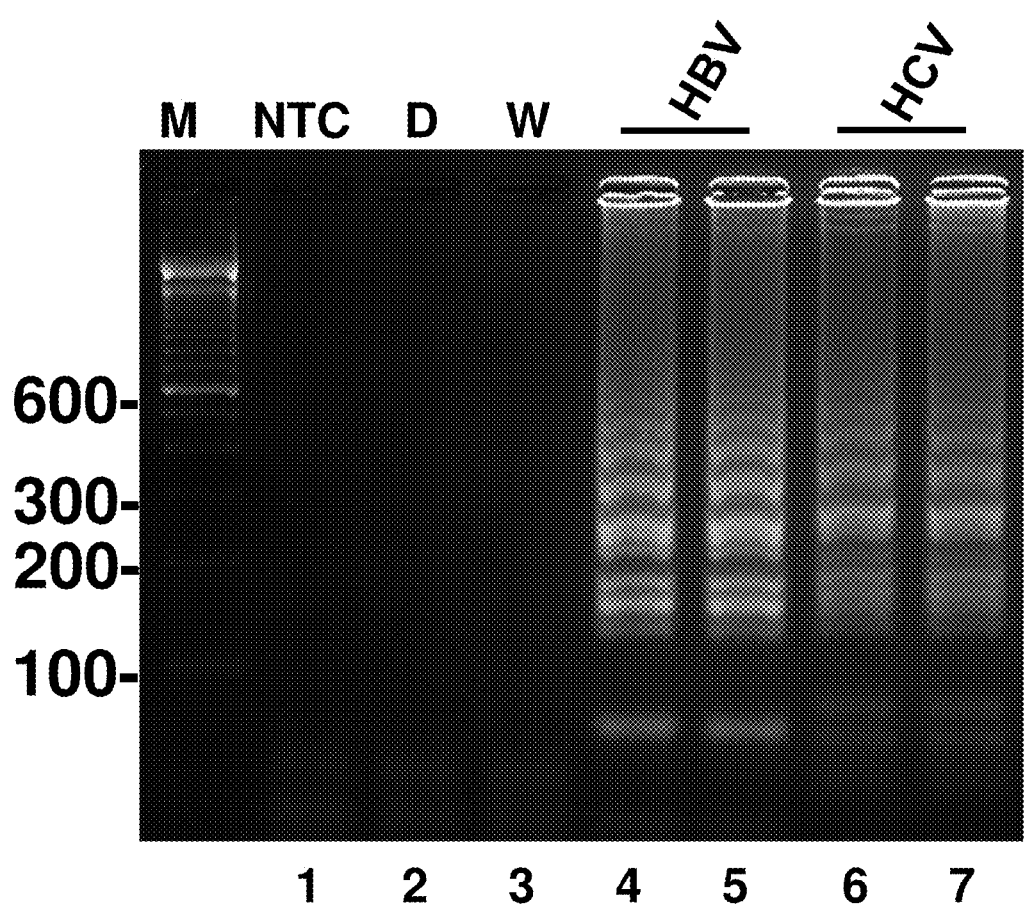
FIGS. 17A-D are digital images showing multiplex LAMP assay reaction products.
Figure 17B:
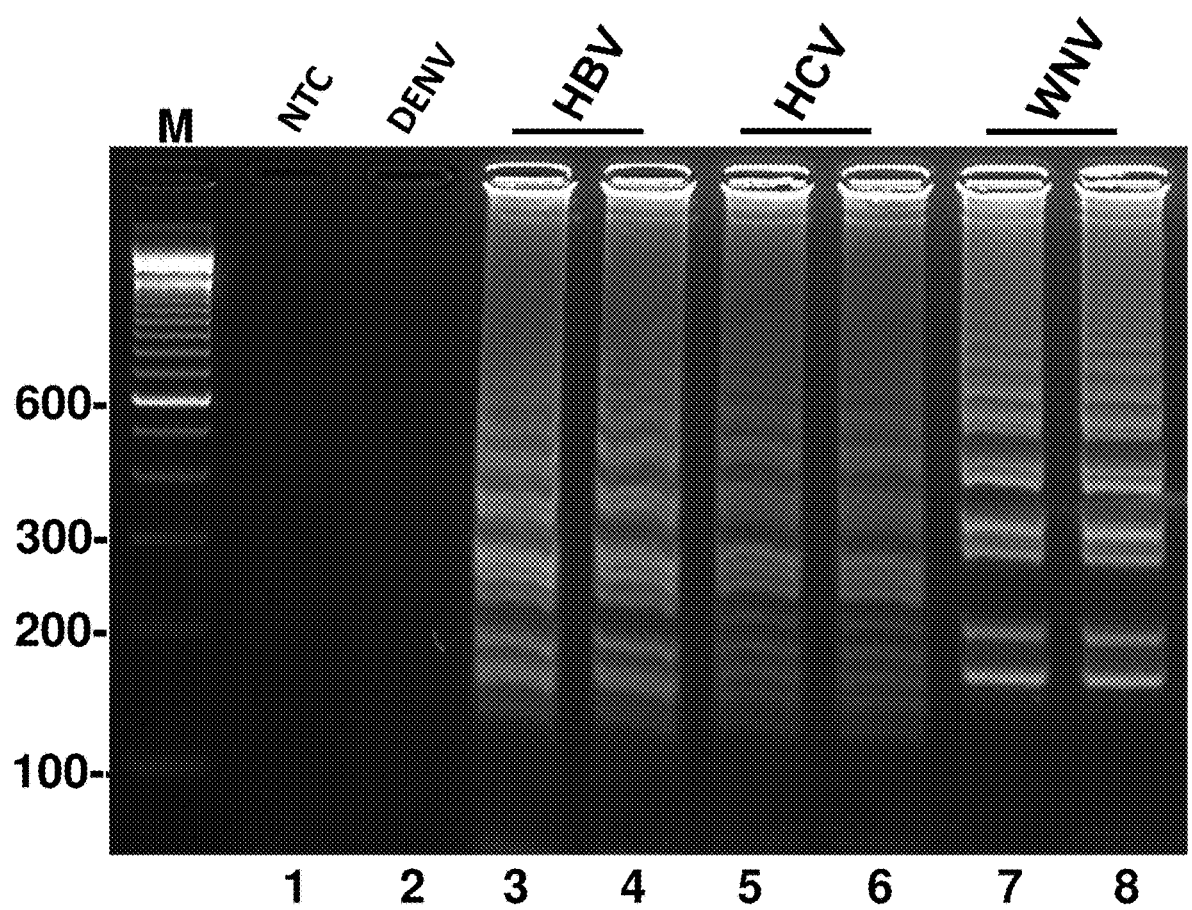
Figure 17C:
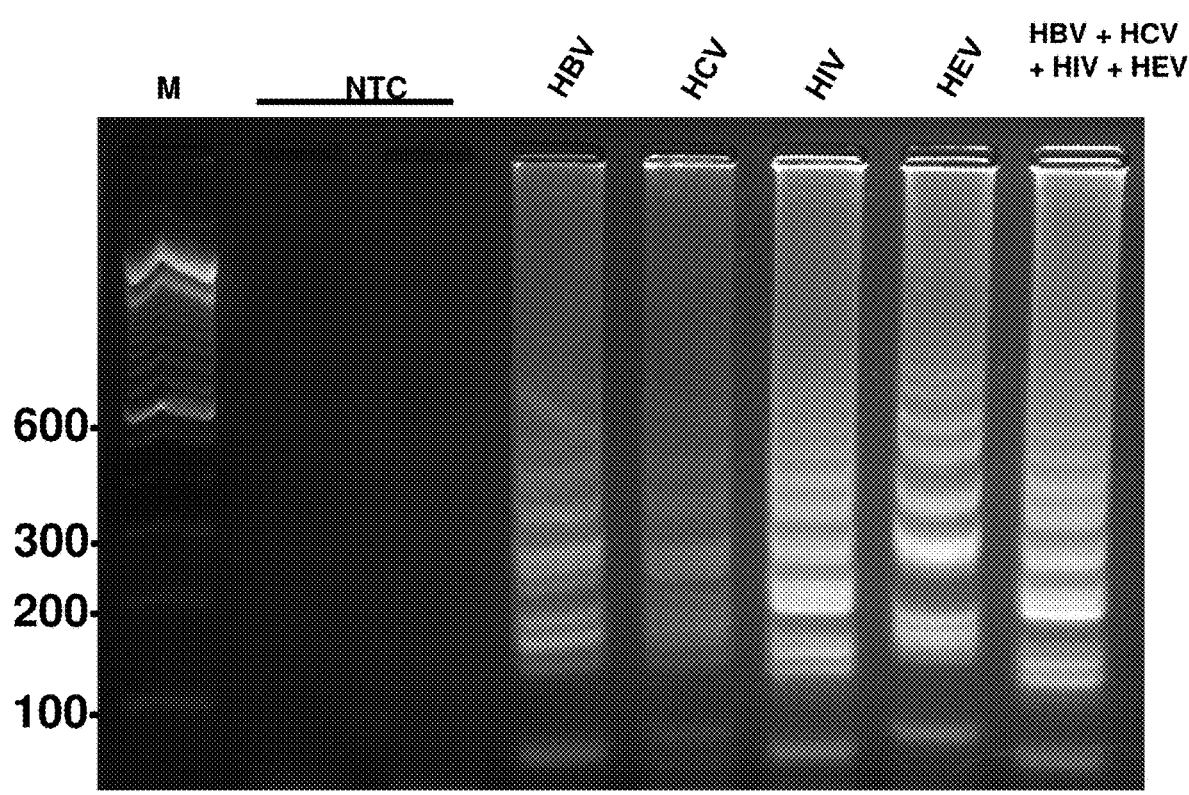
Figure 17D:
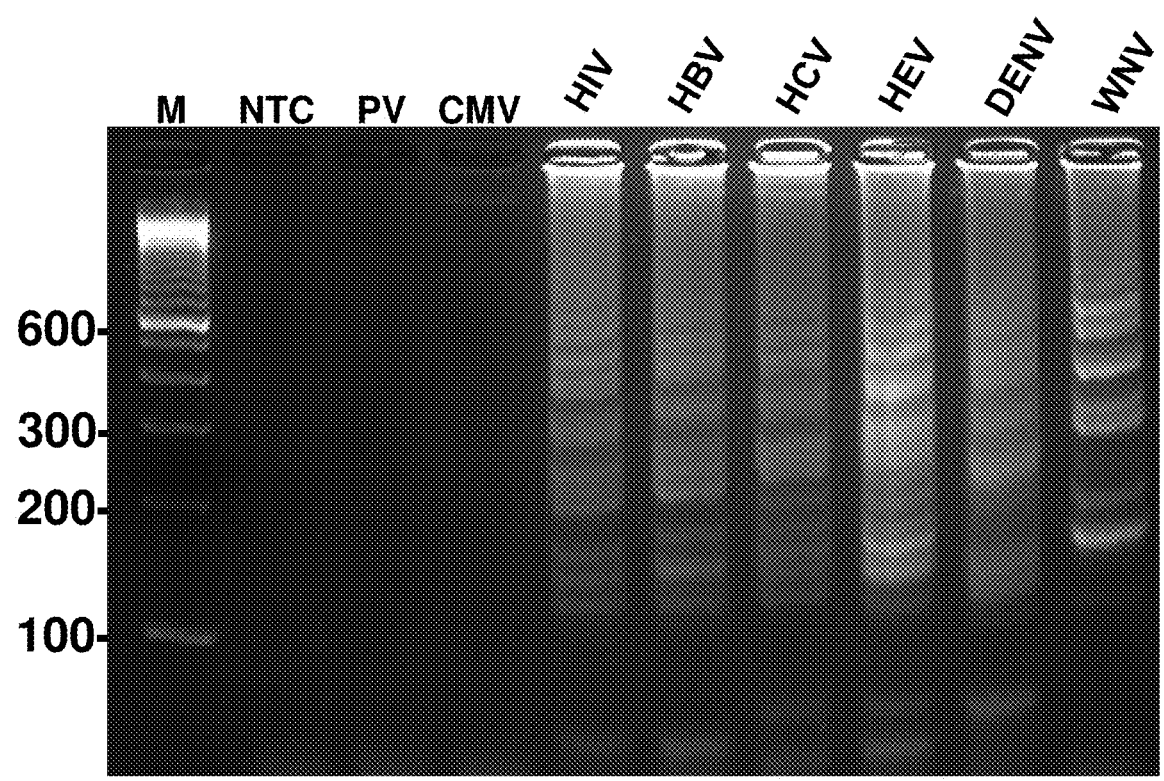

RT-LAMP assays were developed to detect HIV, WNV, DENV, or HEV with specific LAMP primer sets (Table 1). The cross-reactivity of the primers and their ability to specifically amplify the specific virus were evaluated. Electrophoretic analysis demonstrated successful amplification of HIV-1 RNA (using the primer set of SEQ ID NOs: 38, 41, 42, 45, 47, and 48), but not HBV or HCV (FIG. 13). Similarly, the WNV-specific primer set (SEQ ID NOs: 56-61) amplified WNV RNA, but not HCV, HBV, or DENV (FIG. 14). The DENV primer set D1 (SEQ ID NOs: 72-75) successfully amplified DENV RNA (FIG. 15). Finally, the HEV-specific primer set (SEQ ID NOs: 49-54) successfully amplified HEV-3 RNA (FIG. 16A). The HEV primer set could also detect HEV-1 RNA at 10× dilution, but not 100× dilution, while it could detect HEV-3 RNA at both 10× and 100× dilutions (FIG. 16B).

Example 5

Multiplex LAMP Assay for Viral Detection

Introduction

For several decades transfusion and clinical medicine have been bridled with issues of contaminated blood from infected donors. This has led to routine testing of potential blood-donors in the United States and in many developed countries for blood-borne pathogens. The ultimate public health goal has been to ensure safety of blood and blood-products supply as well as ensure early diagnosis for immediate therapeutic invention. Hepatitis B virus (HBV), Hepatitis C virus (HCV), and the emerging Hepatitis E virus (HEV) together infect approximately 700 million people globally and may lead to chronic active hepatitis and hepatocellular carcinoma. On the other hand, infection with the human immunodeficiency virus (HIV) compromises the immune system, while Dengue virus (DENV) and West Nile Virus (WNV) cause hemorrhagic fever and neurodegenerative symptoms, respectively.

Serological and nucleic test-methods including ELISA and quantitative (reverse transcription) polymerase chain reaction or q-(RT)-PCR have been traditionally used to test for these viruses and other pathogens. Performance of ELISA is laborious, employs antibody for detection, is less sensitive, and may miss the window-period of some infections, such as HBV, HCV and HIV. On the other hand, quantitative RT-PCR uses oligo probes that hybridize to the nucleic acid target and allows not only for specific detection, but also for quantitation of target DNA or RNA in real-time.

However, these methods are time-consuming and expensive. Said methods of pathogen detection also require elaborate machines and highly trained personnel to perform. Also, quantitative RT-PCR requires thermocycling for amplification. On the other hand, the quantitative multiplex fluoro-isothermal assay reported in this example is simple and inexpensive. It utilizes three pairs of pathogen-specific oligonucleotides, with a strategically attached reporter/fluorophore-quencher pair that emits fluorescent signal or glow when the fluoro-oligo nucleotide hybridizes to the specific target. This new multiplex isothermal amplification assay can be used for detection and identification pathogens as well as quantitation of pathogen burden in blood.

Methods

DNA and RNA Preparation: DNA and total RNA was extracted from standard reference and genotyping plasma panels of WHO International Standard (OptiQuant-AcroMetrix/Life Technology, Benicia, Calif. and SeraCare, Milford, Mass., respectively). Nucleic acids were also extracted from blind clinical donor plasma using the QiaAmp® Viral RNA mini kit and the QIAamp® DNA Blood Mini Kit modified protocol (Qiagen, Germantown, Md.) as described in Example 2.

Oligonucleotides and Oligofluorophores: Oligonucleotides for detection were designed by analyzing full-length sequences (n=739) of various pathogens, including HBV, HCV, HEV, HIV, WNV, and DENV obtained from the GenBank database using CLUSTALW2. Primers were designed manually with the aid of PrimerExplorer-4 and IDT OligoAnalyzer 3.1 web interfaces. Primer sets consisted of the following: Forward Inner Primer (FIP); Reverse Inner Primer (RIP); Loop Forward Primer (LF); Loop Reverse Primer (LR); Forward Outer Primer (F3), and Reverse Outer Primer (R3). The two sequences of FIP and RIP were spaced with "TTTT" linker, while the Loop Reverse Primers were specifically designed to carry designated probes and quenchers at the 5' and 3' ends, respectively (Example 1). The oligonucleotides and oligofluorophores were synthesized by EuroFins MWG Operon (Huntsville, Ala.) and Integrated DNA Technologies (Coralville, Iowa).

Standards and Controls: Standard quantitated samples of HIV, HCV, HBV as well as Dengue and West Nile viruses were used. DNA and total RNA were extracted from quantitated plasma panels of WHO International Standard (Armored RNA, Asuragen; OptiQuant AcroMetrix/Life Technologies, and SeraCare) serially diluted in nuclease-free water, and used in amplification reactions. HEV was a kind gift of Dr. Sue Emerson of the National Institutes of Health, Bethesda, Md.-USA.

Multiplex Amplification Assay: Detection and identification of the various pathogens was performed by (reverse-transcription)-isothermal amplification in a 25 µL reaction mixture. The mixture comprised of 12.5 µL of 2× (Example 1) and following components: 0.95 µM each of primers FIP and RIP; 0.56 µM each of primers LF and LR; 0.44 µM each of primers F3 and R3. Primer components of the DNA were as follows: 1.0 µM each of primers FIP and RIP; 0.66 µM each of primers LF and LR; 0.33 µM each of primers F3 and R3. Concentrations of oligofluorophores (LRp) ranging from 0.3-0.8 µM of the respective pathogens were added to the single reaction mixture. Also, 12 Units of Bst DNA polymerase (New England Biolabs), 5 U of cloned AMV reverse-transcriptase (Invitrogen/Life Technologies), and 7 U of RnaseOut™ (Invitrogen/Life Technologies) were used to catalyze the reaction. Nucleic acid template volume of 1-5 µL was applied. A no-template (water) control was included in all amplification runs to control for reagent integrity. Known amounts or concentrations of HIV, HCV, HBV, HEV, DENV, and WNV were used either as positive or negative controls depending on experimental design, while normal human plasma served as negative control at all times. Preparation of reaction mixtures was performed in PCR work-stations (Plas Lab, Lansing, Mich.) and precautions observed in order to prevent cross-contamination. Amplification-reactions were conducted at 60° C. for 30 to 60 minutes on a portable digital heat-block (myBlock™, Benchmark Scientific, Edison, N.J.). Reactions were terminated by placing reaction tubes on ice.

Quantitation and Analysis of Products: At the end of the reaction, 1.5-2 µL of product was tested on the NanoDrop 3300 Fluorospectrophotometer in order to read fluorescent emission of amplified products and quantitate the corresponding viral load. Amplicons were analyzed by running 5 µL of reaction products on a 2.8% agarose gel made up in 1×TBE and stained with GelRed (Phenix-Research, NC, USA). Products were run for 50 minutes at 100 volts in 1×TBE buffer and visualized under UV-transilluminator at 302 nm. Gels were photographed using the G:Box gel documentation system (Syngene, Frederick, Md.). Rapid acquisition of results was accomplished by visualizing reaction tubes under UV transilluminator at 302 nm. Analysis of banding-patterns on the gel as well as visual interpretation of fluorescent color-intensity in reaction tubes was performed by at least three laboratory personnel.

Specificity studies: Specificity and cross-reactivity of oligonucleotides and oligofluorophores were evaluated by cross-testing nucleic acids of HIV, HBV, HCV, HEV, DENV, and WNV in multiplexed reactions. Primer-sets were evaluated for their ability to produce distinctly unique banding patterns for the pathogens targeted for identification. The specific-oligofluorophores were analyzed for their ability to produce an intense fluorescence glow when the targeted pathogen was amplified. Assay sensitivity was evaluated by testing serial dilutions of quantitated DNA and RNA of HBV and HCV, respectively.

Assay validation with clinical specimens: Validation of the quantitative multiplex assay was performed by testing donor plasma specimen of the various pathogens. Also, normal/healthy human plasma specimens (n=100) were tested in this study. DNA/total RNA was extracted from the specimens and 3-5 µL subjected to isothermal amplification as described above. Reaction products were analyzed as described in the sub-section "Quantitation and Analysis of Products".

Results

Assay Specificity: Nucleic acid extracted from donor plasma samples and quantitated plasma standards of various pathogens was subjected to multiplex reaction for detection. Pathogen-specific primers and oligofluorophores were used. Cross-reactivity of the primers and oligofluorophores were also investigated for their ability to specifically amplify and detect pathogen of interest. Electrophoretic analysis demonstrated successful amplification of all pathogens tested for by their specific oligonucleotide-set, producing distinctive ladder-like banding pattern unique to the specific pathogen detected (FIGS. 17A-D).

Figure 18A:
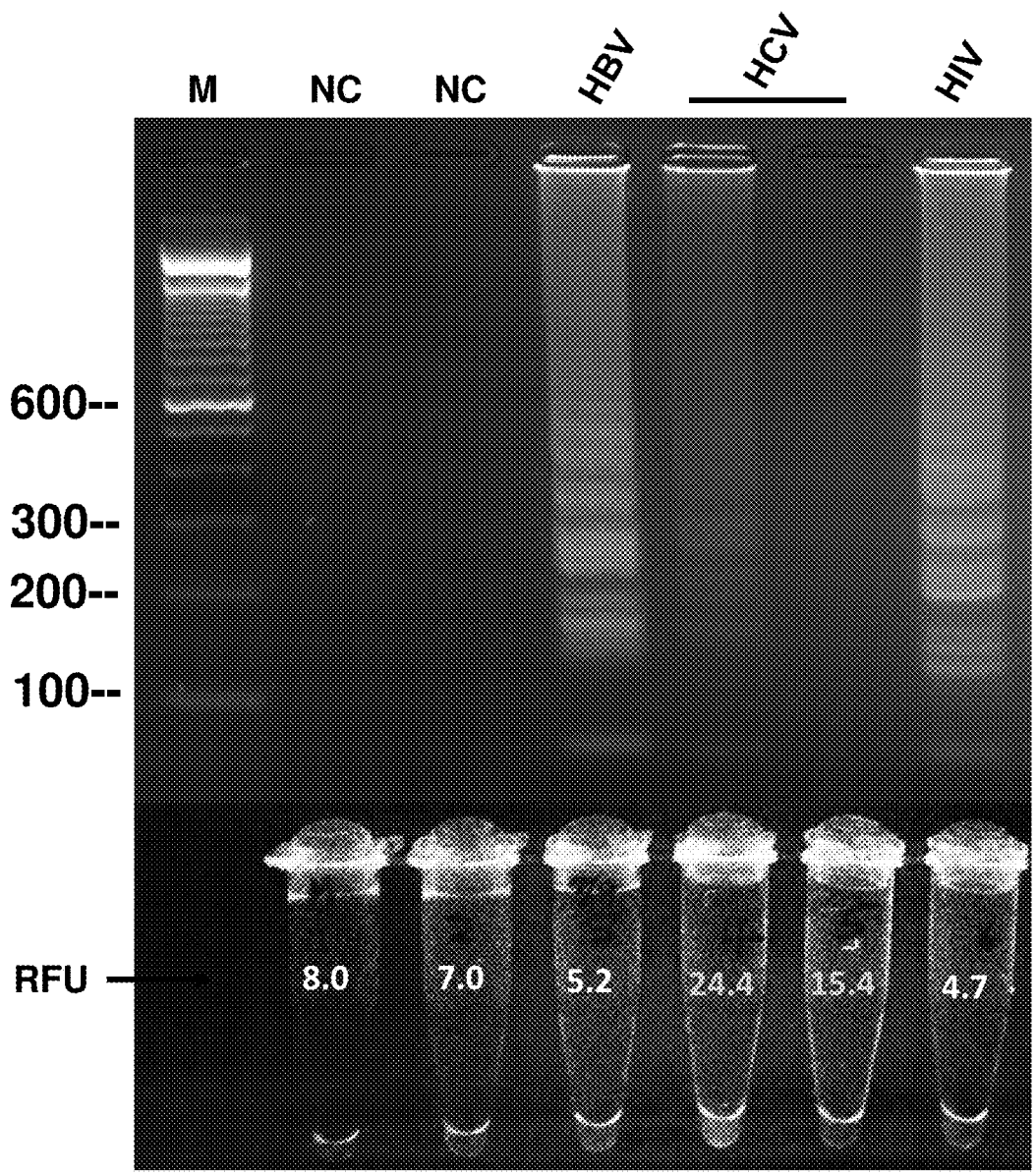
FIGS. 18A-C are digital images showing multiplex LAMP assay reaction products detected by gel electrophoresis or by fluorescence (fluorophore included on the indicated LR primer ("fluoro-oligo")).
Figure 18B:
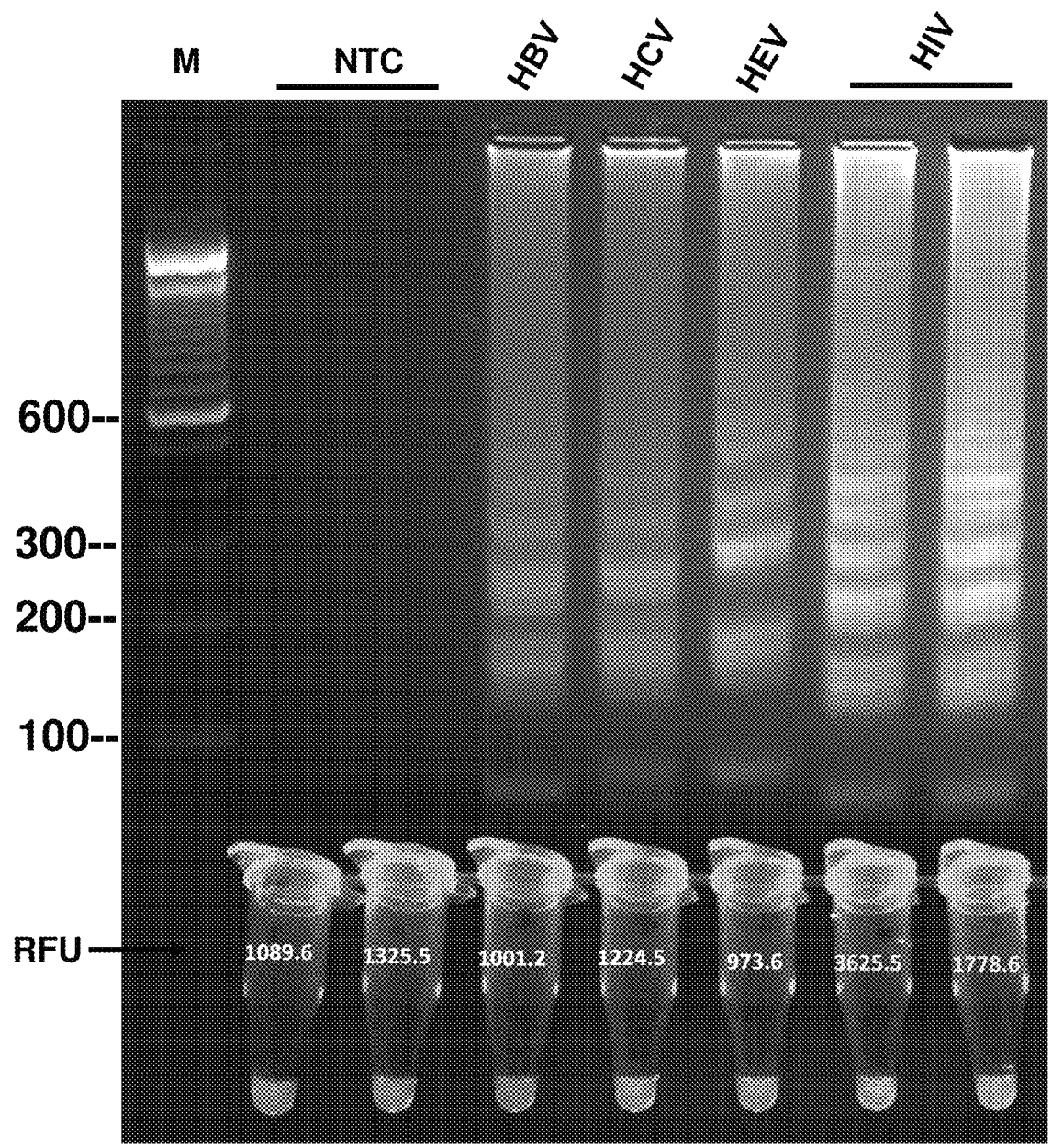
Figure 18C:
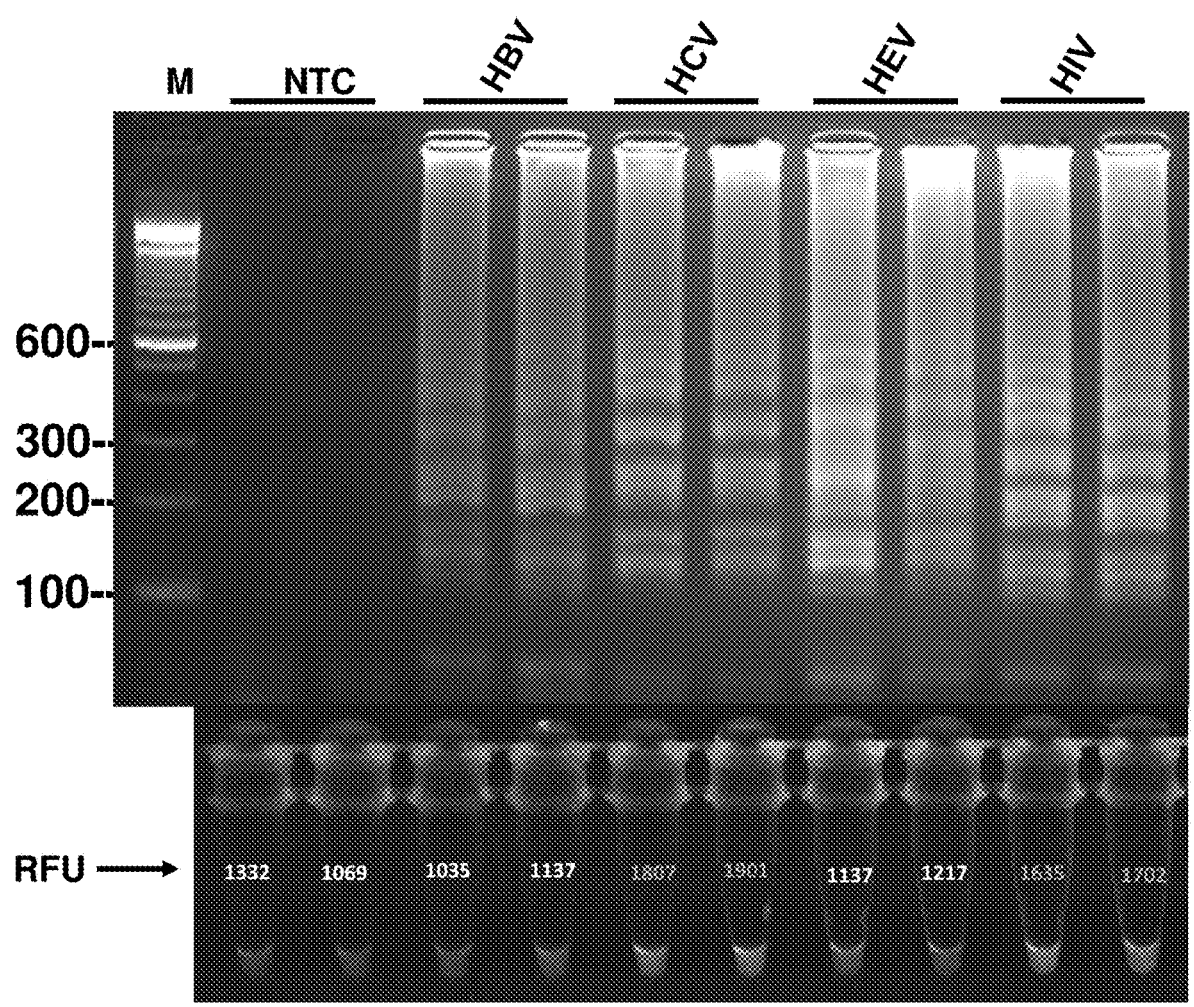

Quantitative Analysis of Products: Pathogen-specific fluorophores were used to for detection of specific agents of infections test in this study. When analyzed with the fluorospectrophotometer, the results produced quantitative numbers that corresponded to the concentration of the pathogen detected (FIGS. 18A-C).

Pathogen detection in clinical specimens: The applicability of the quantitative multiplex test was also evaluated using clinical donor plasma specimens. All donor plasma specimens tested positive by their respective oligofluorophores and primers as indicated by their intense fluorescent glow and quantification value and all normal human plasma specimens (n=100) tested negative (data not shown).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

In view of the above, non-limiting embodiment examples include, but are not limited to, the following:

1. A method of detecting presence of one or more viral nucleic acids comprising one or more of hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, or Dengue virus (DENV) nucleic acid in a sample, comprising:

contacting the sample with one or more sets of loop-mediated isothermal amplification (LAMP) primers specific for one or more of an HBV nucleic acid, an HCV nucleic acid, an HIV nucleic acid, an HEV nucleic acid, a WNV nucleic acid or a DENV nucleic acid under conditions sufficient for amplification of the one or more viral nucleic acids, thereby producing one or more viral nucleic acid amplification products; and detecting the one or more viral nucleic acid amplification products.

2. The method of embodiment 1, wherein the one or more sets of LAMP primers are selected from primers comprising a nucleic acid sequence having at least 90% sequence identity to any one of SEQ ID NOs: 1-75 and 81.

3. The method of embodiment 1 or embodiment 2, wherein the one or more sets of LAMP primers comprise:

(a) a set of LAMP primers specific for an HBV nucleic acid comprising six primers comprising or consisting of the nucleic acid sequences of SEQ ID NOs: 1-6;

(b) a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37;

(c) a set of LAMP primers specific for an HIV nucleic acid comprising six primers comprising or consisting of the nucleic acid sequences of SEQ ID NOs: 38, 41, 42, 45, 47, and 48;

(d) a set of LAMP primers specific for an HEV nucleic acid comprising six primers comprising or consisting of the nucleic acid sequences of SEQ ID NOs: 49-54;

(e) a set of LAMP primers specific for a WNV nucleic acid comprising six primers comprising or consisting of the nucleic acid sequences of SEQ ID NOs: 55 and 57-61 or 56-61; or (f) a set of LAMP primers specific for a DENV nucleic acid comprising four to six primers comprising or consisting of the nucleic acid sequences of SEQ ID NOs: 62-67, 66-71, 68-71, 72-75, or 66, 67, and 72-75.

4. The method of any one of the embodiments 1 to 3, wherein the method comprises contacting the sample with a set of LAMP primers specific for an HBV nucleic acid comprising six primers comprising or consisting of the nucleic acid sequences of SEQ ID NOs: 1-6 and a set of LAMP primers specific for an HCV nucleic acid comprising six primers comprising or consisting of the nucleic acid sequences of SEQ ID NOs: 7-12, 13 and 15-19, or 14-19.

5. The method of any one of the embodiments 1 to 3, wherein the method comprises contacting the sample with a set of LAMP primers specific for an HBV nucleic acid comprising six primers comprising or consisting of the nucleic acid sequences of SEQ ID NOs: 1-6, a set of LAMP primers specific for an HCV nucleic acid comprising six primers comprising or consisting of the nucleic acid sequences of SEQ ID NOs: 7-12, 13 and 15-19, or 14-19, and a set of LAMP primers specific for a WNV nucleic acid comprising six primers comprising or consisting of the nucleic acid sequences of SEQ ID NOs: 55 and 57-61 or 56-61.

6. The method of any one of the embodiments 1 to 3, wherein the method comprises contacting the sample with a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; and a set of LAMP primers specific for an HIV nucleic acid comprising six primers comprising or consisting of the nucleic acid sequences of SEQ ID NOs: 38, 41, 42, 45, 47, and 48.

7. The method of any one of the embodiments 1 to 3, wherein the method comprises contacting the sample with a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; a set of LAMP primers specific for an HIV nucleic acid comprising six primers comprising or consisting of the nucleic acid sequences of SEQ ID NOs: 38, 41, 42, 45, 47, and 48; and a set of LAMP primers specific for an HEV nucleic acid comprising six primers comprising or consisting of the nucleic acid sequences of SEQ ID NOs: 49-54.

8. The method of any one of the embodiments 1 to 3, wherein the method comprises contacting the sample with a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; a set of LAMP primers specific for an HIV nucleic acid comprising six primers comprising or consisting of the nucleic acid sequences of SEQ ID NOs: 38, 41, 42, 45, 47, and 48; a set of LAMP primers specific for an HEV nucleic acid comprising six primers comprising or consisting of the nucleic acid sequences of SEQ ID NOs: 49-54; a set of LAMP primers specific for a WNV nucleic acid comprising six primers comprising or consisting of the nucleic acid sequences of SEQ ID NOs: 55 and 57-61 or 56-61; and a set of LAMP primers specific for a DENV nucleic acid comprising four to six primers comprising or consisting of the nucleic acid sequences of SEQ ID NOs: 62-67, 66-71, 68-71, 72-75, or 66, 67, and 72-75.

9. The method of any one of the embodiments 1 to 8, wherein the sample is contacted with the one or more sets of LAMP primers in a single reaction vessel.

10. A method of detecting presence of hepatitis B virus (HBV) nucleic acid in a sample, comprising:

contacting the sample with a set of loop-mediated isothermal amplification (LAMP) primers specific for an HBV nucleic acid under conditions sufficient for amplification of the HBV nucleic acid, thereby producing an HBV amplification product; and detecting the HBV amplification product, thereby detecting presence of HBV nucleic acid in the sample.

11. The method of embodiment 10, wherein the set of LAMP primers comprises one or more primers comprising a nucleic acid sequence having at least 90% sequence identity to any one of SEQ ID NOs: 1-6.

12. The method of embodiment 11, wherein the set of LAMP primers comprises six primers comprising or consisting of the nucleic acid sequences of SEQ ID NOs: 1-6.

13. A method of detecting presence of hepatitis C virus (HCV) nucleic acid in a sample, comprising:
contacting the sample with at least one set of loop-mediated isothermal amplification (LAMP) primers specific for an HCV nucleic acid under conditions sufficient for amplification of the HCV nucleic acid, thereby producing an HCV amplification product; and
detecting the HCV amplification product, thereby detecting presence of HCV nucleic acid in the sample.

14. The method of embodiment 13, wherein the set of LAMP primers comprises one or more primers comprising a nucleic acid sequence having at least 90% sequence identity to any one of SEQ ID NOs: 7-37.

15. The method of embodiment 14, wherein the set of LAMP primers comprises six primers comprising or consisting of the nucleic acid sequences of SEQ ID NOs: 7-12, 13 and 15-19, or 14-19.

16. The method of embodiment 13, wherein the at least one set of LAMP primers is specific for an HCV genotype 1 (HCV-1) nucleic acid, an HCV genotype 2 (HCV-2) nucleic acid, or an HCV genotype 3 (HCV-3) nucleic acid.

17. The method of embodiment 16, wherein the set of LAMP primers is specific for an HCV-1 nucleic acid and comprises six primers comprising or consisting of SEQ ID NOs: 20-25.

18. The method of embodiment 16, wherein the set of LAMP primers is specific for an HCV-2 nucleic acid and comprises six primers comprising or consisting of SEQ ID NOs: 26-31.

19. The method of embodiment 16, wherein the set of LAMP primers is specific for an HCV-3 nucleic acid and comprises six primers comprising or consisting of SEQ ID NOs: 32-37.

20. A method of detecting presence of human immunodeficiency virus (HIV) nucleic acid in a sample, comprising:
contacting the sample with a set of loop-mediated isothermal amplification (LAMP) primers specific for an HIV nucleic acid under conditions sufficient for amplification of the HIV nucleic acid, thereby producing an HIV amplification product; and
detecting the HIV amplification product, thereby detecting presence of HIV nucleic acid in the sample.

21. The method of embodiment 20, wherein the set of LAMP primers comprises one or more primers comprising a nucleic acid sequence having at least 90% sequence identity to any one of SEQ ID NOs: 38-48 and 81.

22. The method of embodiment 21, wherein the set of LAMP primers comprises six primers comprising or consisting of the nucleic acid sequences of SEQ ID NOs: 38, 41, 42, 45, 47, and 48.

23. A method of detecting presence of hepatitis E virus (HEV) nucleic acid in a sample, comprising:
contacting the sample with a set of loop-mediated isothermal amplification (LAMP) primers specific for an HEV nucleic acid under conditions sufficient for amplification of the HEV nucleic acid, thereby producing an HEV amplification product; and
detecting the HEV amplification product, thereby detecting presence of HEV nucleic acid in the sample.

24. The method of embodiment 23, wherein the set of LAMP primers comprises one or more primers comprising a nucleic acid sequence having at least 90% sequence identity to any one of SEQ ID NOs: 49-54.

25. The method of embodiment 24, wherein the set of LAMP primers comprises six primers comprising or consisting of the nucleic acid sequences of SEQ ID NOs: 49-54.

26. A method of detecting presence of West Nile virus (WNV) nucleic acid in a sample, comprising:
contacting the sample with a set of loop-mediated isothermal amplification (LAMP) primers specific for an WNV nucleic acid under conditions sufficient for amplification of the WNV nucleic acid, thereby producing an WNV amplification product; and
detecting the WNV amplification product, thereby detecting presence of WNV nucleic acid in the sample.

27. The method of embodiment 26, wherein the set of LAMP primers comprises one or more primers comprising a nucleic acid sequence having at least 90% sequence identity to any one of SEQ ID NOs: 55-61.

28. The method of embodiment 27, wherein the set of LAMP primers comprises six primers comprising or consisting of the nucleic acid sequences of SEQ ID NOs: 55 and 57-61 or 56-61.

29. A method of detecting presence of Dengue virus (DENV) nucleic acid in a sample, comprising:
contacting the sample with a set of loop-mediated isothermal amplification (LAMP) primers specific for an DENV nucleic acid under conditions sufficient for amplification of the DENV nucleic acid, thereby producing an DENV amplification product; and
detecting the DENV amplification product, thereby detecting presence of DENV nucleic acid in the sample.

30. The method of embodiment 29, wherein the set of LAMP primers comprises one or more primers comprising a nucleic acid sequence having at least 90% sequence identity to any one of SEQ ID NOs: 62-75.

31. The method of embodiment 30, wherein the set of LAMP primers comprises four to six primers comprising or consisting of the nucleic acid sequences of SEQ ID NOs: 62-67, 66-71, 68-71, 72-75, or 66, 67, and 72-75.

32. The method of any one of the embodiments 1 to 31, wherein at least one primer in the set of LAMP primers comprises a detectable label.

33. The method of embodiment 32, wherein the detectable label comprises a fluorophore.

34. The method of embodiments 32 or 33, wherein the primer further comprises a fluorescence quencher.

35. The method of embodiment 34, wherein the fluorescence quencher comprises a dark quencher.

36. The method of any one of the embodiments 32 to 35, wherein the at least one primer comprising the detectable label comprises any one of SEQ ID NOs: 5, 6, 11, 12, 18, 19, 24, 25, 30, 31, 36, 37, 46-48, 53, 54, 60, 61, 66, or 67.

37. The method of any one of the embodiments 1 to 36, further comprising contacting the sample with a reverse transcriptase under conditions sufficient for reverse transcription of the viral nucleic acid.

38. The method of any one of the embodiments 1 to 37, wherein detecting the viral nucleic acid amplification product comprises turbidity measurement, fluorescence detection, or gel electrophoresis.

39. The method of any one of the embodiments 1 to 38, wherein the sample comprises isolated DNA, isolated RNA, blood, plasma, serum, urine, saliva, tissue biopsy, fine needle aspirate, or a surgical specimen.

40. An isolated nucleic acid primer comprising a nucleic acid sequence at least 90% identical to any one of SEQ ID NOs: 1-75 and 81.

41. The isolated nucleic acid primer of embodiment 40, comprising the nucleic acid sequence of any one of SEQ ID NOs: 1-75 and 81.

42. The isolated nucleic acid primer of embodiment 41, consisting of the nucleic acid sequence of any one of SEQ ID NOs: 1-75 and 81.

43. The isolated nucleic acid primer of any one of the embodiments 40 to 42, further comprising a fluorophore, a fluorescent quencher, or both.

44. The isolated nucleic acid primer of embodiment 43, wherein the nucleic acid sequence of the primer comprises or consists of SEQ ID NOs: 6, 12, 19, 25, 31, 37, 48, 54, 61, or 67.

45. A kit comprising at least one set of LAMP primers in a container.

46. The kit of embodiment 45, wherein the at least one set of LAMP primers comprises:
(a) a set of LAMP primers specific for an HBV nucleic acid comprising six primers comprising or consisting of the nucleic acid sequences of SEQ ID NOs: 1-6;
(b) a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37;
(c) a set of LAMP primers specific for an HIV nucleic acid comprising six primers comprising or consisting of the nucleic acid sequences of SEQ ID NOs: 38, 41, 42, 45, 47, and 48;
(d) a set of LAMP primers specific for an HEV nucleic acid comprising six primers comprising or consisting of the nucleic acid sequences of SEQ ID NOs: 49-54;
(e) a set of LAMP primers specific for a WNV nucleic acid comprising six primers comprising or consisting of the nucleic acid sequences of SEQ ID NOs: 55 and 57-61 or 56-61; or
(f) a set of LAMP primers specific for a DENV nucleic acid comprising four to six primers comprising or consisting of the nucleic acid sequences of SEQ ID NOs: 62-67, 66-71, 68-71, 72-75, or 66, 67, and 72-75.

47. The kit of embodiment 46, wherein the kit comprises two or more sets of LAMP primers in a single container.

48. The kit of embodiment 47, wherein the kit comprises a set of LAMP primers specific for an HBV nucleic acid comprising six primers comprising or consisting of the nucleic acid sequences of SEQ ID NOs: 1-6 and a set of LAMP primers specific for an HCV nucleic acid comprising six primers comprising or consisting of the nucleic acid sequences of SEQ ID NOs: 7-12, 13 and 15-19, or 14-19 in a single container.

49. The kit of embodiment 47, wherein the kit comprises a set of LAMP primers specific for an HBV nucleic acid comprising six primers comprising or consisting of the nucleic acid sequences of SEQ ID NOs: 1-6, a set of LAMP primers specific for an HCV nucleic acid comprising six primers comprising or consisting of the nucleic acid sequences of SEQ ID NOs: 7-12, 13 and 15-19, or 14-19, and a set of LAMP primers specific for a WNV nucleic acid comprising six primers comprising or consisting of the nucleic acid sequences of SEQ ID NOs: 55 and 57-61 or 56-61 in a single container.

50. The kit of embodiment 47, wherein the kit comprises a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; and a set of LAMP primers specific for an HIV nucleic acid comprising six primers comprising or consisting of the nucleic acid sequences of SEQ ID NOs: 38, 41, 42, 45, 47, and 48 in a single container.

51. The kit of embodiment 47, wherein the kit comprises a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; a set of LAMP primers specific for an HIV nucleic acid comprising six primers comprising or consisting of the nucleic acid sequences of SEQ ID NOs: 38, 41, 42, 45, 47, and 48; and a set of LAMP primers specific for an HEV nucleic acid comprising six primers comprising or consisting of the nucleic acid sequences of SEQ ID NOs: 49-54 in a single container.

52. The kit of embodiment 47, wherein the kit comprises a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; a set of LAMP primers specific for an HIV nucleic acid comprising six primers comprising or consisting of the nucleic acid sequences of SEQ ID NOs: 38, 41, 42, 45, 47, and 48; a set of LAMP primers specific for an HEV nucleic acid comprising six primers comprising or consisting of the nucleic acid sequences of SEQ ID NOs: 49-54; a set of LAMP primers specific for a WNV nucleic acid comprising six primers comprising or consisting of the nucleic acid sequences of SEQ ID NOs: 55 and 57-61 or 56-61; and a set of LAMP primers specific for a DENV nucleic acid comprising four to six primers comprising or consisting of the nucleic acid sequences of SEQ ID NOs: 62-67, 66-71, 68-71, 72-75, or 66, 67, and 72-75 in a single container.

53. The kit of any one of the embodiments 40 to 53, further comprising a buffer comprising 2% D-mannitol, 0.2% Triton®-X100, 40 mM Tris-HCl, 20 mM KCl, 20 mM $(NH_4)_2SO_4$, 6 mM $MgSO_4$, 0.5 M L-proline, 10 mM Tris acetate, 1.6 mM magnesium acetate, 15 mM potassium acetate and 2 mM each of dATP, dCTP, dGTP, and dTTP.

54. A nucleic acid amplification buffer comprising 2% D-mannitol, 0.2% Triton®-X100, 40 mM Tris-HCl, 20 mM KCl, 20 mM $(NH_4)_2SO_4$, 6 mM $MgSO_4$, 0.5 M L-proline, 10 mM Tris acetate, 1.6 mM magnesium acetate, 15 mM potassium acetate and 2 mM each of dATP, dCTP, dGTP, and dTTP.

55. The buffer of embodiment 54, wherein the buffer has a pH of about 7.8. In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

What is claimed is:

1. A method of detecting a presence of viral nucleic acids comprising hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, and Dengue virus (DENV) nucleic acid in a sample, comprising:
- contacting the sample with one or more sets of loop-mediated isothermal amplification (LAMP) primers specific for an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids if present in the sample, thereby producing one to a plurality of viral nucleic acid amplification products depending on the number of viral nucleic acids in the sample; and
- detecting any present viral nucleic acid amplification products in the sample;
- wherein the one or more sets of LAMP primers are selected from primers comprising a nucleic acid sequence having at least 90% sequence identity to any one of SEQ ID NOs: 1-75 and 81;
- wherein at least one primer in the set of LAMP primers comprises a detectable label;
- wherein all SEQ ID NO: 1-75 and 81 are present in the method;
- providing a single pathogen specific detector and labelling the single pathogen specific detector at both ends;
- wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;
- wherein both fluorescence and quenching are accomplished in a single-tube one-step reaction for simultaneous detection and identification of multiple pathogens with differentiating ladder-like banding patterns.

2. A method of detecting a presence of viral nucleic acids comprising hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, and Dengue virus (DENV) nucleic acid in a sample, comprising:
- contacting the sample with one or more sets of loop-mediated isothermal amplification (LAMP) primers specific for an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids if present in the sample, thereby producing one to a plurality of viral nucleic acid amplification products depending on the number of viral nucleic acids in the sample; and
- detecting any present viral nucleic acid amplification products in the sample;
- wherein the one or more sets of LAMP primers comprise:
  - (a) a set of LAMP primers specific for an HBV nucleic acid comprising six primers comprising or consisting of the nucleic acid sequences of SEQ ID NOs: 1-6;
  - (b) a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37;
  - (c) a set of LAMP primers specific for an HIV nucleic acid comprising six primers comprising or consisting of the nucleic acid sequences of SEQ ID NOs: 38, 41, 42, 45, 47, and 48;
  - (d) a set of LAMP primers specific for an HEV nucleic acid comprising six primers comprising or consisting of the nucleic acid sequences of SEQ ID NOs: 49-54;
  - (e) a set of LAMP primers specific for a WNV nucleic acid comprising six primers comprising or consisting of the nucleic acid sequences of SEQ ID NOs: 55 and 57-61 or 56-61; and
  - (f) a set of LAMP primers specific for a DENV nucleic acid comprising four to six primers comprising or consisting of the nucleic acid sequences of SEQ ID NOs: 62-67, 66-71, 68-71, 72-75, or 66, 67, and 72-75;
- providing a single pathogen specific detector and labelling the single pathogen specific detector at both ends;
- wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;
- wherein both fluorescence and quenching are accomplished in a single-tube one-step reaction for simultaneous detection and identification of multiple pathogens with differentiating ladder-like banding patterns.

3. A method of detecting presence of viral nucleic acids comprising one or more of hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, or Dengue virus (DENV) nucleic acid in a sample, comprising:
- contacting the sample with one or more sets of loop-mediated isothermal amplification (LAMP) primers specific for one or more of an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids, thereby producing one or more viral nucleic acid amplification products; and detecting any present viral nucleic acid amplification products in the sample;

wherein the method comprises contacting the sample with a set of LAMP primers specific for an HBV nucleic acid comprising six primers comprising or consisting of the nucleic acid sequences of SEQ ID NOs: 1-6 and a set of LAMP primers specific for an HCV nucleic acid comprising six primers comprising or consisting of the nucleic acid sequences of SEQ ID NOs: 7-12, 13 and 15-19, or 14-19;

providing a single pathogen specific detector and labelling the single pathogen specific detector at both ends;

wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns.

4. A method of detecting presence of viral nucleic acids comprising one or more of hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, or Dengue virus (DENV) nucleic acid in a sample, comprising:

contacting the sample with one or more sets of loop-mediated isothermal amplification (LAMP) primers specific for one or more of an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids, thereby producing one or more viral nucleic acid amplification products; and detecting any present viral nucleic acid amplification products in the sample;

wherein the method comprises contacting the sample with a set of LAMP primers specific for an HBV nucleic acid comprising six primers comprising or consisting of the nucleic acid sequences of SEQ ID NOs: 1-6, a set of LAMP primers specific for an HCV nucleic acid comprising six primers comprising or consisting of the nucleic acid sequences of SEQ ID NOs: 7-12, 13 and 15-19, or 14-19, and a set of LAMP primers specific for a WNV nucleic acid comprising six primers comprising or consisting of the nucleic acid sequences of SEQ ID NOs: 55 and 57-61 or 56-61;

providing a single pathogen specific detector and labelling the single pathogen specific detector at both ends;

wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns.

5. A method of detecting presence of viral nucleic acids comprising one or more of hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, or Dengue virus (DENV) nucleic acid in a sample, comprising:

contacting the sample with one or more sets of loop-mediated isothermal amplification (LAMP) primers specific for one or more of an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids, thereby producing one or more viral nucleic acid amplification products; and detecting any present viral nucleic acid amplification products in the sample;

wherein the method comprises contacting the sample with a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; and a set of LAMP primers specific for an HIV nucleic acid comprising six primers comprising or consisting of the nucleic acid sequences of SEQ ID NOs: 38, 41, 42, 45, 47, and 48;

providing a single pathogen specific detector and labelling the single pathogen specific detector at both ends;

wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns.

6. A method of detecting presence of viral nucleic acids comprising one or more of hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, or Dengue virus (DENV) nucleic acid in a sample, comprising:

contacting the sample with one or more sets of loop-mediated isothermal amplification (LAMP) primers specific for one or more of an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids, thereby producing one or more viral nucleic acid amplification products; and detecting any present viral nucleic acid amplification products in the sample;

wherein the method comprises contacting the sample with a set of LAMP primers specific for an HBV nucleic acid comprising six primers comprising or consisting of the nucleic acid sequences of SEQ ID NOs: 1-6; a set of LAMP primers specific for an HCV nucleic acid comprising six primers comprising or consisting of the nucleic acid sequences of SEQ ID NOs: 7-12, 13 and 15-19, 14-19, 20-25, 26-31, or 32-37; a set of LAMP primers specific for an HIV nucleic acid comprising six primers comprising or consisting of the nucleic acid sequences of SEQ ID NOs: 38, 41, 42, 45, 47, and 48; and a set of LAMP primers specific for an HEV nucleic acid comprising six primers comprising or consisting of the nucleic acid sequences of SEQ ID NOs: 49-54;

providing a single pathogen specific detector and labelling the single pathogen specific detector at both ends;

wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns.

7. A method of detecting a presence of viral nucleic acids comprising hepatitis B virus (HBV) nucleic acid, hepatitis C virus (HCV) nucleic acid, human immunodeficiency virus (HIV) nucleic acid, hepatitis E virus (HEV) nucleic acid, West Nile virus (WNV) nucleic acid, and Dengue virus (DENV) nucleic acid in a sample, comprising:

contacting the sample with one or more sets of loop-mediated isothermal amplification (LAMP) primers specific for an HBV nucleic acid, an HCV nucleic acid, an HIV nucleic acid, an HEV nucleic acid, a WNV nucleic acid and a DENV nucleic acid under conditions sufficient for amplification of the one or more viral nucleic acids if present in the sample, thereby producing one to a plurality of viral nucleic acid amplification products depending on the number of viral nucleic acids in the sample; and detecting any present viral nucleic acid amplification products in the sample;

wherein the sample is contacted with the one or more sets of LAMP primers in a single reaction vessel;

wherein at least one primer in the set of LAMP primers comprises a detectable label;

providing a single pathogen specific detector and labelling the single pathogen specific detector at both ends;

wherein the step of providing a single pathogen specific detector and labelling the single pathogen specific detector at both ends comprising the steps of (i) providing a single pathogen-specific Loop Reverse oligonucleotide probe (LRp) per pathogen; (ii) covalently labeling the LRp probe with a fluorophore at a 5'-end and with a quencher at a 3'-end to create a bi-labeled LRp olingonucleotide; and (iii) using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns;

wherein all SEQ ID NO: 1-75 and 81 are present in the method.

8. The method of claim 1 wherein the detectable label comprises a fluorophore.

9. The method of claim 1 wherein the primer further comprises a fluorescence quencher.

10. The method of claim 9 wherein the fluorescence quencher comprises a dark quencher.

11. The method of claim 1 further comprising contacting the sample with a reverse transcriptase under conditions sufficient for reverse transcription of the viral nucleic acid.

12. The method of 2 wherein detecting the viral nucleic acid amplification product comprises turbidity measurement, fluorescence detection, or gel electrophoresis.

13. The method of claim 1 wherein the sample comprises isolated DNA, isolated RNA, blood, plasma, serum, urine, saliva, tissue biopsy, fine needle aspirate, or a surgical specimen.

14. The method of claim 7 wherein the primer further comprises a dark quencher.

15. The method of claim 7 wherein the at least one primer comprising the detectable label comprises any one of SEQ ID NOs: 5, 6, 11, 12, 18, 19, 24, 25, 30, 31, 36, 37, 46-48, 53, 54, 60, 61, 66, or 67.

16. The method of claim 7 further comprising contacting the sample with a reverse transcriptase under conditions sufficient for reverse transcription of the viral nucleic acid.

17. The method of 9 wherein detecting the viral nucleic acid amplification product comprises turbidity measurement, fluorescence detection, or gel electrophoresis.

18. The method of claim 7 wherein the sample comprises isolated DNA, isolated RNA, blood, plasma, serum, urine, saliva, tissue biopsy, fine needle aspirate, or a surgical specimen.

19. A one-step single-tube multiplex-reaction for detection of viruses and pathogens infecting human, plants, and animals using a single pathogen specific detector that is labeled at both ends; comprising:

providing a single pathogen-specific Loop Reverse oligonucleotide probe (LRp) per pathogen;

covalently labeling the LRp probe with a fluorophore at a 5'-end and with a quencher at a 3'-end to create a bi-labeled LRp olingonucleotide;

using the bi-labeled LRp oligonucleotide along with a plurality of other primers as a set per pathogen for a one-step single-tube multiplex-reaction;

wherein both fluorescence and quenching are accomplished in a single-tube one-step reaction for simultaneous detection and identification of multiple pathogens with differentiating ladder-like banding patterns;

wherein all SEQ ID NO: 1-75 and 81 are present in the method.

* * * * *